(12) United States Patent
Itoh et al.

(10) Patent No.: US 7,109,200 B2
(45) Date of Patent: Sep. 19, 2006

(54) CARBAMATE DERIVATIVES, PROCESS FOR PRODUCING THE SAME AND USE THEREOF

(75) Inventors: Fumio Itoh, Tsukuba (JP); Hiroshi Banno, Kawanishi (JP); Masaki Kawamura, Ikeda (JP); Shuji Kitamura, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 46 days.

(21) Appl. No.: 10/416,240

(22) PCT Filed: Nov. 8, 2001

(86) PCT No.: PCT/JP01/09759

§ 371 (c)(1),
(2), (4) Date: May 6, 2003

(87) PCT Pub. No.: WO02/38560

PCT Pub. Date: May 16, 2002

(65) Prior Publication Data

US 2004/0038986 A1 Feb. 26, 2004

(30) Foreign Application Priority Data

Nov. 8, 2000 (JP) .............................. 2000-341067

(51) Int. Cl.
*A61K 31/497* (2006.01)
*C07D 241/01* (2006.01)
*C07D 401/00* (2006.01)

(52) U.S. Cl. ............................ 514/253.01; 514/253.04; 544/357; 544/360

(58) Field of Classification Search ................ 544/360, 544/357; 514/253.01, 253.04, 253.11
See application file for complete search history.

(56) References Cited

U.S. PATENT DOCUMENTS 5,612,353 A * 3/1997 Ewing et al. ................ 514/309

6,403,595 B1 * 6/2002 Tawada et al. ......... 514/255.02
6,680,312 B1 * 1/2004 Tawada et al. ............. 514/183

FOREIGN PATENT DOCUMENTS

| EP | 1048652 A1 * | 11/2000 |
| WO | WO 99/37304 | 7/1999 |
| WO | WO 9937304 A1 * | 7/1999 |
| WO | WO00/03290 * | 6/2000 ................. 514/183 |

* cited by examiner

*Primary Examiner*—Thomas McKenzie
*Assistant Examiner*—Raymond Covington
(74) *Attorney, Agent, or Firm*—Elaine M. Ramesh; Mark Chao

(57) ABSTRACT

Novel carbamate derivatives which are useful as drugs because of inhibiting activated blood coagulation factor X and thus exerting an anticoagulant effect. Compounds represented by the formula:

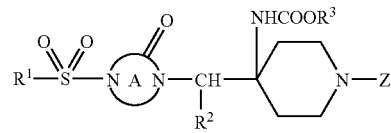

wherein $R^1$ represents a group represented by the formula:

(wherein $Y^1$ represents CH=CH, etc.), which may be substituted, etc.; the ring A represents an oxo-substituted nitrogen-containing heterocyclic ring which may be further substituted; $R^2$ represents a hydrogen atom, optionally substituted $C_{1-4}$ alkyl, etc.; $R^3$ represents optionally substituted $C_{1-4}$ alkyl, etc.; and Z represents an optionally substituted nitrogen containing heterocyclic group, etc., or salts thereof.

25 Claims, No Drawings

CARBAMATE DERIVATIVES, PROCESS FOR PRODUCING THE SAME AND USE THEREOF

This application is the National Phase filing of International Patent Application No. PCT/JP01/09759, filed 8 Nov. 2001.

TECHNICAL FIELD

The present invention relates to a novel carbamate derivative having the anticoagulant activity which inhibits activated blood coagulation factor X (FXa) and is useful as a medicament, a process for preparing the same and use thereof.

BACKGROUND ART

It is important to inhibit the formation of a thrombus in preventing and/or treating cardiac infarction, cerebral thrombosis and the like, and various anti-thombotic agents such as anti-thrombin agents and platelet aggregation inhibitors have been developed. Nevertheless, platelet aggregation inhibitors as well as anti-thrombin agents have hemorrhagic side effects and problems in their safety, since these agents possess a platelet aggregation-inhibiting activity in combination with anti-coagulative effect. On the other hand, FXa inhibitors specifically inhibit a coagulation factor, and thus are considered to be useful as anticoagulant.

So far, compounds having FXa-inhibiting effects are disclosed for example in JP 7-112970 A, JP 5-208946 A, WO-96/16940, WO96/40679, WO 96/10022, WO 98/28269, WO 99/37304, WO 99/127, and the like.

Currently, there is a demand for a compound which has a stronger FXa inhibiting activity than that of the above-mentioned compounds having FXa inhibiting activity by oral administration, and is practically excellent as a medicament.

SUMMARY OF THE INVENTION

The present invention provides a novel carbamate derivative which has the inhibiting activity specific for FXa, is effective by oral administration, and is useful as a medicament for preventing and/or treating diseases attributable to thrombus or infarction.

The present inventors extensively studied and, as a result, first synthesized a compound represented by the formula:

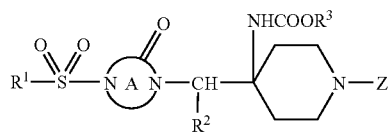

wherein $R^1$ denotes a group represented by the formula:

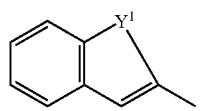

(wherein $Y^1$ denotes O, NH, S, $CH_2CH_2$, CH=CH, N=CH, $OCH_2$, $SCH_2$ or two hydrogen atoms), or a group represented by the formula:

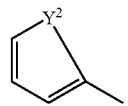

(wherein $Y^2$ denotes O, S, N=CH or CH=CH), each of which may be substituted, ring A denotes a nitrogen-containing heterocyclic ring which is substituted with an oxo group and may be further substituted, $R^2$ denotes a hydrogen atom, an optionally substituted $C_{1-4}$ alkyl group, an optionally esterified carboxyl group or a cyano group, $R^3$ denotes a $C_{1-4}$ alkyl group or a $C_{2-4}$ alkenyl group, each of which may be substituted with a substituent selected from a halogen atom, a hydroxy group, an optionally substituted alkoxy group, an optionally substituted amino group and an optionally esterified carboxyl group, and Z denotes (1) an optionally substituted amino group, (2) an optionally substituted hydrocarbon group, (3) an optionally substituted imidoyl group or (4) an optionally substituted nitrogen-containing heterocyclic group, which has such chemical structural specificity that the compound has a carbamate group at the 4-position of piperidine (hereinafter, referred to as compound (I) in some cases) or a salt thereof, and found that this compound has an unexpectedly excellent FXa inhibiting activity based on the specific chemical structure and can be safely administered orally as a medicament for preventing and/or treating diseases attributable to thrombus or infarction. Based on these findings, the present invention has been completed.

That is, the present invention relates to:
(1) Compound (I) or a salt thereof;
(2) the compound according to the above (1), wherein $R^1$ is an optionally substituted naphthyl group;
(3) the compound according to the above (1), wherein $R^1$ is 6-halogeno-2-naphthyl group;
(4) the compound according to the above(1), wherein $R^1$ is an optionally substituted benzopyranyl group;
(5) the compound according to the above (1), wherein $R^1$ is 7-halogeno-2H-3-benzopyranyl group;
(6) the compound according to the above (1), wherein $R^1$ is an optionally substituted phenyl group;
(7) the compound according to the above (1), wherein $R^1$ is a 4-$C_{2-4}$ alkenyl-phenyl group;
(8) the compound according to the above (1), wherein ring A is a ring represented by;

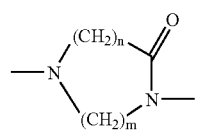

wherein n denotes 1 or 2, and m denotes 2 or 3;
(9) the compound according to the above (1), wherein ring A is an optionally substituted oxohomopiperazine ring;
(10) the compound according to the above (1), wherein ring A is an optionally substituted oxopiperazine ring;
(11) the compound according to the above (1), wherein $R^2$ is a hydrogen atom;

(12) the compound according to the above (1), wherein $R^3$ is a $C_{1-4}$ alkyl group which may be substituted with a substituent selected from a halogen atom, a hydroxy group, an optionally substituted alkoxy group, an optionally substituted amino group and a optionally esterified carboxyl group;

(13) the compound according to the above (1), wherein $R^3$ is methyl, ethyl, or propyl;

(14) the compound according to the above (1), wherein Z is an optionally substituted imidoyl group;

(15) the compound according to the above (1), wherein Z is an optionally substituted $C_{1-4}$ imidoyl group;

(16) the compound according to the above (1), wherein Z is an optionally substituted amidino group;

(17) the compound according to the above (1), wherein Z is an optionally substituted nitrogen-containing heterocyclic group;

(18) the compound according to the above (1), wherein Z is a nitrogen-containing heterocyclic group which may be substituted with a substituent selected from a $C_{1-4}$ alkyl group and an optionally substituted amino group;

(19) the compound according to the above (1), wherein Z is an optionally substituted pyrimidyl group;

(20) the compound according to the above (1), wherein Z is an optionally substituted pyridyl group;

(21) the compound according to the above (1), which is a compound selected form the group consisting of 4-(6-chloronaphthalene-2-sulfonyl)-1-[4-methoxycarbonylamino-1-(4-pyridyl)piperidin-4-ylmethyl]-2-piperazinone, 4-(6-chloronaphthalene-2-sulfonyl)-1-[4-ethoxycarbonylamino-1-(4-pyridyl)piperidin-4-ylmethyl]-2-piperazinone, 4-(7-chloro-2H-benzopyran-3-sulfonyl)-1-[4-methoxycarbonylamino-1-(4-pyridyl)piperidin-4-ylmethyl]-2-piperazinone, 4-(7-chloro-2H-benzopyran-3-sulfonyl)-1-[4-ethoxycarbonylamino-1-(4-pyridyl)piperidin-4-ylmethyl]-2-piperazinone, 1-[4-methoxycarbonylamino-1-(4-pyridyl)piperidin-4-ylmethyl]-4-(4-vinylbenzenesulfonyl)-2-piperazinone, 1-[4-ethoxycarbonylamino-1-(4-pyridyl)piperidin-4-ylmethyl]-4-(4-vinylbenzenesulfonyl)-2-piperazinone, 1-[4-ethoxycarbonylamino-1-(2-methyl-4-pyridyl)piperidin-4-ylmethyl]-4-(4-vinylbenzenesulfonyl)-2-piperazinone, 1-[4-propoxycarbonylamino-1-(4-pyridyl)piperidin-4-ylmethyl]-4-(4-vinylbenzenesulfonyl)-2-piperazinone, 1-[4-ethoxycarbonylamino-1-(4-pyridyl)piperidin-4-ylmethyl]-4-(4-bromobenzenesulfonyl)-2-piperazinone and 1-[4-ethoxycarbonylamino-1-(2-methyl-4-pyridyl)piperidin-4-ylmethyl]-4-(4-bromobenzenesulfonyl)-2-piperazinone or a salt thereof;

(22) a prodrug of compound (I) or a salt thereof;

(23) a pharmaceutical composition, which comprises compound (I) or a salt thereof, or a prodrug thereof;

(24) the composition according to the above (23), which is an anticoagulant;

(25) the composition according to the above (23), which is an activated blood coagulation factor X inhibiting agent;

(26) the composition according to the above (23), which is an agent for preventing and/or treating cardiac infarction, cerebral thrombosis, deep vein thrombosis, pulmonary thrombotic embolus or thrombotic embolus during or after operation;

(27) a process for preparing a compound represented by the formula:

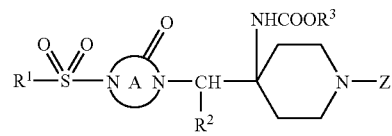

wherein each symbol is as defined hereinafter, or a salt thereof, which comprises (i) reacting a compound represented by the formula:

$R^1SO_2Q$ wherein Q denotes a leaving group, and the other symbol is as defined in the above (1), or a salt thereof, with a compound represented by the formula:

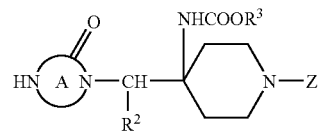

wherein the symbols are as defined in the above (1), or a salt thereof, (ii) reacting a compound represented by the formula:

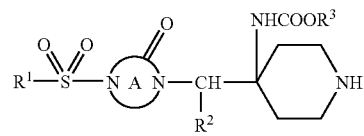

wherein the symbols are as defined in the above (1), or a salt thereof, with a compound represented by the formula:

$L^1$-Z wherein $L^1$ denotes a leaving group, and the other symbol is as defined in the above (1), or a salt thereof, (iii) reacting a compound represented by the formula;

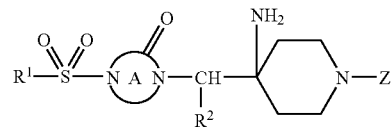

wherein the symbols are as defined in the above (1), or a salt thereof, with a compound represented by the formula:

$L^2$-$COOR^3$ wherein $L^2$ denotes a leaving group, and the other symbol is as defined in the above (1), or a salt thereof;

(28) a method for inhibiting blood coagulation in a mammal, which comprises administering an effective amount of the compound according to the above (1) or a salt thereof, or a prodrug thereof to the mammal;

(29) a method for inhibiting activated blood coagulation factor X in a mammal, which comprises administering an effective amount of the compound according to the above (1) or a salt thereof, or a prodrug thereof to the mammal;

(30) a method for preventing and/or treating cardiac infarction, cerebral thrombosis, deep vein thrombosis, pulmonary thrombotic embolus or thrombotic embolus during or after operation in a mammal, which comprises administering an effective amount of the compound according to the above (1) or a salt thereof, or a prodrug thereof to the mammal;

(31) use of the compound according to the above (1) or a salt thereof, or a prodrug thereof for manufacturing a medicament for inhibiting blood coagulation;

(32) use of the compound according to the above (1) or a salt thereof, or a prodrug thereof for manufacturing a medicament for inhibiting activated blood coagulation factor X;

(33) use of the compound according to the above (1) or a salt thereof, or a prodrug thereof for preparation of a medicament for preventing and/or treating cardiac infarction, cerebral thrombosis, deep vein thrombosis, pulmonary thrombotic embolus or thrombotic embolus during or after operation.

EMBODIMENTS FOR CARRYING OUT THE INVENTION

In the above mentioned formulas, $R^1$ denotes a group represented by the formula:

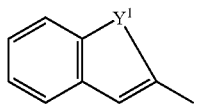

wherein $Y^1$ denotes O, NH, S, $CH_2CH_2$, CH=CH, N=CH, $OCH_2$, $SCH_2$ or two hydrogen atoms, or a group represented by the formula:

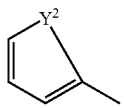

wherein $Y^2$ denotes O, S, N=CH or CH=CH, each of which may be substituted.

Examples of the above group represented by the formula:

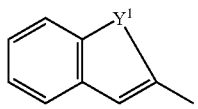

wherein $Y^1$ denotes O, NH, S, $CH_2CH_2$, CH=CH, N=CH, $OCH_2$, $SCH_2$ or two hydrogen atoms and, in case that two kinds of atoms are present in atoms constituting a straight chain part of $Y^1$, any of left and right atoms may be bound to a carbon atom having a bond to $SO_2$ and, for example, when $Y^1$ is N=CH, it may be either N=CH-[carbon atom having a bond to $SO_2$] or CH=N-[carbon atom having a bond to $SO_2$], include β-styryl group, 2-naphthyl group, 3-dihydronaphthyl group, 3-quinolyl group, 3-isoquinolyl group, 2H-3-benzopyranyl group, 2H-3-benzothiopyranyl group, 2-benzothienyl group, 2-benzofuranyl group, 2-indolyl group, and the like.

In addition, when $Y^1$ denotes two hydrogen atoms, the "group represented by the formula:

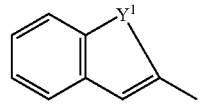

wherein $Y^1$ denotes two hydrogen atoms, which may be substituted" as $R^1$ means an "group represented by the formula:

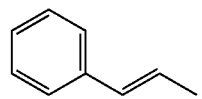

which may be substituted".

Examples of the above group represented by the formula:

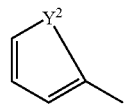

wherein $Y^2$ denotes O, S, N=CH, or CH=CH and, in case that two kinds of atoms are present in atoms constituting a straight chain part of $Y^2$, any of left and right atoms may be bound to a carbon atom having a bond to $SO_2$ and, for example, when $Y^2$ is N=CH, it may be either N=CH-[carbon atom having a bond to $SO_2$] or CH=N-[carbon atom having a bond to $SO_2$], include phenyl group, 2-furyl group, 2-thienyl group, 2-pyridyl group, 3-pyridyl group, and the like.

Examples of the substituent which may be possessed by the group represented by $R^1$ include an optionally substituted alkyl group, an optionally substituted alkenyl group, and optionally substituted alkynyl group, an optionally substituted aryl group, an optionally substituted cycloalkyl group, an optionally substituted cycloalkenyl group, an optionally substituted heterocyclic group, an optionally substituted amino group, an optionally substituted imidoyl group (e.g. a group represented by the formula: —C(U')=N—U [wherein U and U' each denotes a hydrogen atom or a substituent (U preferably denotes a hydrogen atom)] etc.), an optionally substituted amidino group (e.g. a group represented by the formula: —C(NT'T")=N-T [wherein T, T' and T" each denotes a hydrogen atom or a substituent (T preferably denotes a hydrogen atom)] etc.), an optionally substituted hydroxy group (preferably, optionally substituted $C_{1-4}$ alkoxy group such as methoxy, ethoxy, n-propoxy group and the like, each of which may be substituted), an optionally substituted thiol group, an optionally esterified carboxyl group, an optionally substituted carbamoyl group, an optionally substituted thiocarbamoyl group, an optionally substituted sulfamoyl group, a halogen atom (e.g. fluorine, chlorine, bromine, iodine etc, preferably chlorine, bromine, etc), a cyano group, a nitro group, a sulfonic acid-derived acyl group, a carboxylic acid-derived acyl group (preferably, halogen, an optionally substituted $C_{1-4}$ alkyl group, an optionally substituted $C_{2-4}$ alkenyl group, an optionally substituted aryl group, an optionally substituted 5- to 6-membered aromatic heterocyclic group, an optionally substituted $C_{1-4}$ alkoxy group, an optionally substituted amino group, an optionally esterified carboxyl group, a cyano group, an amidino group, etc.), and the like. These optional substituents may occur 1 to 5 (preferably 1 to 3; more preferably 1 to 2) times at any possible positions. In addition, a group represented by $R^1$ may have an oxo group and, for example, when $R^1$ is benzopyranyl, $R^1$ may form benzo-α-pyronyl, benzo-γ-pyronyl, or the like.

Examples of the aryl group in the "optionally substituted aryl group" as the substituent include $C_{6-14}$ aryl groups such as phenyl, naphthyl, anthryl, phenanthryl, acenaphthylenyl, and the like. Examples of the substituent for the aryl group include a lower alkoxy group (e.g. $C_{1-6}$ alkoxy group such as methoxy, ethoxy, propoxy, etc.), a halogen atom (e.g. fluorine, chlorine, bromine, iodine, etc.), a lower alkyl group (e.g. $C_{1-6}$ alkyl group such as methyl, ethyl, propyl, etc.), a lower alkenyl group (e.g. $C_{2-6}$ alkenyl group such as vinyl, allyl, etc.), a lower alkynyl group (e.g. $C_{2-6}$ alkynyl group such as ethynyl, propargyl, etc.), an optionally substituted amino group, an optionally substituted hydroxy group, a cyano group, a $C_{1-4}$ alkylsulfonyl group, a sulfamoyl group, an optionally substituted amidino group, and the like. These optional substituents may occur 1 to 3 times at any possible positions.

Examples of the "optionally substituted amino group", the "optionally substituted hydroxy group" and the "optionally substituted amidino group" as the substituent include the same "optionally substituted amino group", "optionally substituted hydroxy group" and "optionally substituted amidino group" as those of the substituent which may be possessed by a group represented by $R^1$.

Examples of the cycloalkyl group in the "optionally substituted cycloalkyl group" as the substituent include $C_{3-7}$ cycloalkyl groups such as cyclopropyl, cyclobutyl, cyclopentyl, cyclohexyl, cycloheptyl, and the like. Here, examples of the substituent for the cycloalkyl group include the same number of the same substituents as those in the above-mentioned "optionally substituted aryl group".

Examples of the cycloalkenyl group in the "optionally substituted cycloalkenyl group" as the substituent include $C_{3-6}$ cycloalkenyl groups such as cyclopropenyl, cyclobutenyl, cyclopentenyl, cyclohexenyl, and the like. Here, examples of the substituent for the optionally substituted cycloalkenyl group include the same number of the same substituents as those in the above-mentioned "optionally substituted aryl group".

Examples of the alkyl group in the "optionally substituted alkyl group" as the substituent include $C_{1-6}$ alkyl groups such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, and the like (preferably, $C_{1-4}$ alkyl groups such as methyl, ethyl, n-propyl, n-butyl, etc.). Here, examples of the substituent for the alkyl group include the same number of the same substituents as those in the above-mentioned "optionally substituted aryl group".

Examples of the alkenyl group in the "optionally substituted alkenyl group" as the substituent include $C_{2-6}$ alkenyl groups such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, and the like (preferably, $C_{2-4}$ alkenyl groups such as vinyl, allyl, propenyl, 1-butenyl, etc.; more preferably, vinyl). Here, examples of the substituent for the alkenyl group include the same number of the same substituents as those in the above-mentioned "optionally substituted aryl group".

Examples of the alkynyl group in the "optionally substituted alkynyl group" as the substituent include $C_{2-6}$ alkynyl groups such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, and the like (preferably, $C_{2-4}$ alkynyl groups). Here, examples of the substituent for the alkynyl group include the same number of the same substituents as those in the above-mentioned "optionally substituted aryl".

Examples of the heterocyclic group in the "optionally substituted heterocyclic group" as the substituent include an aromatic heterocyclic group, a saturated or unsaturated non-aromatic heterocyclic group (aliphatic heterocyclic group), and the like, which contains at least one (preferably 1 to 4, more preferably 1 to 2) of 1 to 3 kinds (preferably 1 to 2 kinds) of hetero atoms selected from an oxygen atom, a sulfur atom and a nitrogen atom as an atom (ring atom) constituting a ring system.

Examples of the "aromatic heterocyclic group" include a 5- to 6-membered aromatic monocyclic heterocyclic group such as aromatic monocyclic heterocyclic group (e.g. furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc.; preferably pyridyl, thienyl, furyl, etc.) and 8- to 16-membered (preferably 8- to 12-membered) aromatic fused heterocyclic group such as aromatic fused heterocyclic group (e.g. benzofuranyl, isobenzofuranyl, benzo[b]thienyl, indolyl, isoindolyl, 1H-indazolyl, benzindazolyl, benzoxazolyl, 1,2-benzoisoxazoly, benzothiazolyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, γ-carbolinyl, acridinyl, phenoxazinyl, phenothiazinyl, phenazinyl, phenoxathynyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.) (preferably a heterocyclic ring in which the above-mentioned one to two (preferably one) 5- to 6-membered aromatic monocyclic heterocyclic group(s) is (are) fused with one to two (preferably one) benzene ring(s) or a heterocyclic ring in which the above-mentioned two to three (preferably two) same or different 5- to 6-membeed aromatic monocyclic heterocyclic groups are fused).

Examples of the "non-aromatic heterocyclic group" include 3- to 8-membered (preferably 5- to 6-membered) saturated or unsaturated (preferably saturated) non-aromatic heterocyclic group (aliphatic heterocyclic group) such as oxiranyl, azetidinyl, oxetanyl, thietanyl, pyrrolidinyl, tetrahydrofuryl, thioranyl, piperidyl, tetrahydropyranyl, morpholinyl, thiomorpholinyl, piperazinyl, and the like, and non-aromatic heterocyclic group in which a part or all of double bonds of the above-mentioned aromatic monocyclic heterocyclic group or aromatic fused heterocyclic group are saturated, such as 1,2,3,4-tetrahydroquinolyl, 1,2,3,4-tetrahydroisoquinolyl, and the like.

Examples of the substituent which may be possessed by the "optionally substituted heterocyclic group" as the substituent include a lower alkyl group (e.g. $C_{1-6}$ alkyl groups such as methyl, ethyl, propyl, etc.), a lower alkenyl group ($C_{2-6}$ alkenyl groups such as vinyl, allyl, etc.), a lower alkynyl group (e.g. $C_{2-6}$ alkynyl groups such as ethynyl, propargyl, etc.), an acyl group (e.g. $C_{1-6}$ alkanoyl (e.g. formyl, acetyl, propionyl, pivaloyl, etc.), $C_{1-6}$ alkylsulfonyl (e.g. methanesulfonyl, ethanesulfonyl etc.), benzoyl, benzenesulfonyl, etc.), an optionally substituted amino group, an optionally substituted hydroxy group, a halogen atom (e.g. fluorine, chlorine, bromine, iodine, etc., preferably chlorine, bromine, etc.), an optionally substituted imidolyl group, an optionally substituted amidino group, and the like.

Examples of the "optionally substituted amino group", the "optionally substituted hydroxy group", the "optionally substituted imidoyl group" and the "optionally substituted amidino group" which may be possesses by the "optionally substituted heterocyclic group" as the substituent include the same "optionally substituted hydroxy group", "optionally substituted imidoyl group" and "optionally substituted amidino group" as those of the substituent which may be possesses by a group represented by $R^1$.

Examples of the substituent in the "optionally substituted amino group", the "optionally substituted imidoyl group", the "optionally substituted amidino group", the "optionally substituted hydroxy group" and the "optionally substituted thiol group" as the substituent which may be possesses by a group represented by $R^1$ include a lower alkyl group (e.g. $C_{1-6}$ alkyl groups such as methyl, ethyl, propyl, isopropyl, butyl, isobutyl, t-butyl, pentyl, hexyl, etc.), an acyl group (e.g. $C_{1-6}$ alkanoyl (e.g. formyl, acetyl, propionyl, pivaloyl, etc.), $C_{1-6}$ alkylsulfonyl (e.g. methanesulfonyl, ethanesulfonyl, etc.), benzoyl, benzenesulfonyl, etc.), carbamoyl, mono-$C_{1-6}$ alkylcarbamoyl, di-$C_{1-6}$ alkylcarbamoyl, optionally halogenated $C_{1-6}$ alkoxycarbonyl (e.g. methoxycarbonyl, ethoxycarbonyl, trifluoromethoxycarbonyl, 2,2,2-trifluoroethoxycarbonyl, trichloromethoxycarbonyl, 2,2,2-trichloroethoxycarbonyl, etc.), etc.), a heterocyclic group (the same "heterocyclic group" as that of the substituent which may be possessed by a group represented by $R^1$, preferably pyridyl, more preferably 4-pyirdyl), and the like. The "amino group" in the "optionally substituted amino group" as the substituent may be substituted with an optionally substituted imidoyl group (e.g. $C_{1-6}$ alkylimidoyl, $C_{1-6}$ alkanoylimidoyl (e.g. formylimidoyl, etc.), amidino, etc.), or an amino group optionally substituted with 1 to 2 $C_{1-6}$ alkyl(s), etc. Alternatively, two substituents may be taken together with the nitrogen atom to form a cyclic amino group, and examples of such the cyclic amino group include 3- to 8-membered (preferably 5- to 6-membered) cyclic amino such as 1-azetidinyl, 1-pyrrolidinyl, piperidino, thiomorpholino, morpholino, 1-piperazinyl and 1-piperazinyl optionally having at the 4-position a lower alkyl group (e.g. $C_{1-6}$ alkyl groups such as methyl, ethyl, propyl, isopropyl, butyl, t-butyl, pentyl, hexyl, etc.), an aralkyl group (e.g. $C_{7-10}$ aralkyl groups such as benzyl, phenethyl, etc.), an aryl group (e.g. $C_{6-10}$ aryl groups such as phenyl, 1-naphthyl, 2-naphthyl, etc.), and the like, 1-pyrrolyl, 1-imidazolyl, and the like.

As the "optionally substituted amino group" as the substituent, preferred are amino, methylamino, dimethylamino, acetylamino, methanesulfoneamino, ureido, etc.

Examples of the "optionally substituted carbamoyl group" include N-monosubstituted carbamoyl group and N,N-disubstituted carbamoyl group, in addition to unsubstituted carbamoyl.

The "N-monosubstituted carbamoyl group" means a carbamoyl group having one substituent on the nitrogen atom, and examples of the substituent include a lower alkyl group (e.g. $C_{1-6}$ alkyl groups such as methyl, ethyl, propyl, isopropyl, butyl, isobutyl, t-pentyl, hexyl, etc.), a lower alkenyl group (e.g. $C_{2-6}$ alkenyl groups such as vinyl, allyl, isopropenyl, propenyl, butenyl, pentenyl, hexenyl, etc.), a cycloalkyl group (e.g. $C_{3-6}$ cycloalkyl groups such as cyclopropyl, cyclobutyl, cyclopentyl, cyclohexyl, etc.), an aryl group (e.g. $C_{6-10}$ aryl groups such as phenyl, 1-naphthyl, 2-naphthyl, etc.), an aralkyl group (e.g. $C_{7-10}$ aralkyl groups such as benzyl, phenethyl, etc., preferably a phenyl-$C_{1-4}$ alkyl group, etc.), an arylalkenyl group (e.g. $C_{8-10}$ arylalkenyl groups such as cinnamyl, etc., preferably a phenyl-$C_{2-4}$ alkenyl group, etc.), a heterocyclic group (e.g. the same "heterocyclic group" as that of the substituent which may be possesses by a group represented by $R^1$), and the like. The lower alkyl group, the lower alkenyl group, the cycloalkyl group, the aryl group, the aralkyl group, the arylalkenyl group and the heterocyclic group may have substituent(s), and examples of the substituent include a hydroxy group, an optionally substituted amino group [the amino group may have 1 or 2 substituent(s) such as a lower alkyl group (e.g. $C_{1-6}$ alkyl groups such as methyl, ethyl, propyl, isopropyl, butyl, isobutyl, t-butyl, pentyl, hexyl, etc.), an acyl group (e.g. $C_{1-6}$ alkanoyl (e.g. formyl, acetyl, propionyl, pivaloyl, etc.), $C_{1-6}$ alkylsulfonyl (e.g. methanesulfonyl, ethanesulfonyl, etc.), benzoyl, benzenesulfonyl, etc.), a carboxyl group, a $C_{1-6}$-alkoxy-carbonyl group, etc.], a halogen atom (e.g. fluorine, chlorine, bromine, iodine, etc.), a nitro group, a cyano group, a lower alkyl group optionally substituted with 1 to 5 halogen atom(s) (e.g. fluorine, chlorine, bromine, iodine, etc.), a lower alkoxy group optionally substituted with 1 to 5 halogen atom(s) (e.g. fluorine, chlorine, bromine, iodine, etc.), and the like. Examples of the lower alkyl group include $C_{1-6}$ alkyl groups such as methyl, ethyl, n-propyl, isopropyl, n-butyl, isobutyl, sec-butyl, tert-butyl, pentyl, hexyl, and the like and, in particular, methyl, ethyl, and the like are preferable. Examples of the lower alkoxy group include $C_{1-6}$ alkoxy groups such as methoxy, ethoxy, n-propoxy, isopropoxy, n-butoxy, isobutoxy, sec-butoxy, tert-butoxy, and the like and, in particular, methoxy, ethoxy, and the like are preferable. In addition, these substituents may be the same or different and the number of the substituent(s) is preferably 1, 2 or 3 (preferably 1 or 2).

The "N,N-disubstituted carbamoyl group" means a carbamoyl group which has two substituents on the nitrogen atom, and examples of one of the substituents include the same substituents as those in the above-mentioned "N-monosubstituted carbamoyl group", and examples of the other substituent include a lower alkyl group (e.g. $C_{1-6}$ alkyl groups such as methyl, ethyl, propyl, isopropyl, butyl, t-butyl, pentyl, hexyl, etc.), a $C_{3-6}$ cycloalkyl group (e.g. cyclopropyl, cyclobutyl, cyclopentyl, cyclohexyl, etc.), a $C_{7-10}$ aralkyl group (e.g. benzyl, phenethyl, etc., preferably a phenyl-$C_{1-4}$ alkyl group etc.), and the like. Alternatively, two substituents may be taken together with the nitrogen atom to form a cyclic amino group, and examples of the cyclic aminocarbamoyl group in such the case include 3- to 8-membered (preferably 5- to 6-membered) cyclic aminocarbamoyl such as 1-azetidinylcarbonyl, 1-pyrrolidinylcarbonyl, piperidinocarbonyl, morpholinocarbonyl, 1-piperazinylcarbonyl and 1-piperazinylcarbonyl optionally having at the 4-position a lower alkyl group (e.g. $C_{1-6}$ alkyl groups such as methyl, ethyl, propyl, isopropyl, butyl, t-butyl, pentyl, hexyl, etc.), an aralkyl group (e.g. $C_{7-10}$ aralkyl groups such as benzyl, phenethyl, etc.), an aryl group (e.g. $C_{6-10}$ aryl groups such as phenyl, 1-naphthyl, 2-naphtyl, etc.).

Examples of the substituent for the "optionally substituted thiocarbamoyl group" and the "optionally substituted sulfamoyl group" include the same substituents as those for the above-mentioned "optionally substituted carbamoyl group".

Examples of the optionally esterified carboxyl group include a lower alkoxycarbonyl group, an aryloxycarbonyl group, an aralkyloxycarbonyl group, and the like, in addition to a free carboxyl group.

Examples of the "lower alkoxycarbonyl group" include $C_{1-6}$ alkoxy-carbonyl groups such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, and the like and, inter alia, $C_{1-3}$ alkoxy-carbonyl groups such as methoxycarbonyl, ethoxycarbonyl, propoxycarbonyl, and the like are preferable.

As the "aryloxycarbonyl group", preferred are, for example, $C_{7-12}$ aryloxy-carbonyl groups such as phenoxycarbonyl, 1-naphthoxycarbonyl, 2-naphthoxycarbonyl, and the like.

As the "aralkyloxycarbonyl group", preferred are, for example, $C_{7-10}$ aralkyloxy-carbonyl groups such as benzyloxycarbonyl, phenethyloxycarbonyl, and the like (preferably, $C_{6-10}$ aryl-$C_{1-4}$ alkoxy-carbonyl, etc.)

The "aryloxycarbonyl group", and the "aralkyloxycarbonyl group" may have substituent(s), and, as the substituent, the same number of the same substituents as those of the aryl group and aralkyl group described as the substituent for the above-mentioned N-monosubstituted carbamoyl group can be used.

Examples of the "sulfonic acid-derived acyl group" as the substituent include sufonyl bound to one substituent on the nitrogen atom of the above-mentioned "N-monosubstituted carbamoyl group", preferably acyls such as $C_{1-6}$ alkylsulfonyl such as methanesulfonyl, ethanesulfonyl, and the like.

Examples of the "carboxylic acid-derived acyl group" as the substituent include carbonyl bound to a hydrogen atom or one substituent on the nitrogen atom of the above-mentioned "N-monosubstituted carbamoyl group", preferably acyls such as $C_{1-6}$ alkanoyl such as formyl, acetyl, propionyl, pivaloyl, and the like, and benzoyl, and the like.

As $R^1$, preferred are an optionally substituted naphthyl group, an optionally substituted phenyl group, an optionally substituted benzopyranyl group, and the like and, inter alia, an aryl group optionally substituted with a halogen atom or $C_{2-4}$ alkenyl (preferably $C_{6-14}$ aryl such as phenyl, 1-naphthyl, 2-naphthyl, etc.), a benzopyranyl group optionally substituted with a halogen atom and, inter alia, 6-halogeno-2-naphthyl group, 4-vinylpheyl group and 7-halogeno-2H-3-benzopyranyl group are preferable.

In the above formulas, ring A denotes a nitrogen-containing heterocyclic ring which is substituted with an oxo group and may be further substituted, that is, a nitrogen-containing heterocyclic ring which may have an optional substituent at any possible position in addition to one oxo group expressly shown as the substituent. The position replaced with the oxo group may be any possible position, and it is preferable that the oxo group replaces on the carbon atom adjacent to the nitrogen atom to which a group represented by the formula —CH($R^2$)— is bound.

Examples of the "nitrogen-containing heterocyclic ring" in the "nitrogen-containing heterocyclic ring which is substituted with an oxo group and may be further substituted" represented by ring A include a ring in which the oxo group is bound to a replaceable position of a 6- to 8-membered nitrogen-containing heterocyclic ring containing at least two nitrogen atoms in addition to carbon atoms, and optionally further containing 1 to 3 hetero atom(s) selected from an oxygen atom, a sulfur atom and the like as an atom constituting the ring system (ring atom) (preferably 6- to 8-membered nitrogen-containing heterocyclic ring composed of carbon atoms and at least two nitrogen atoms), and the like.

It is essential that the "6- to 8-membered nitrogen-containing heterocyclic ring" has the oxo group, and examples thereof, when the oxo group is omitted and the heterocyclic ring is exemplified as a divalent group, include a divalent 6-membered nitrogen-containing heterocyclic group containing 2 to 4 nitrogen atoms such as piperazinediyl (piperazine-1,4-diyl, etc.), tetrahydropyrazinediyl, triazacyclohexanediyl, tetraazacyclohexanediyl, tetrahydrotriazinediyl and the like, a divalent 7-membered nitrogen-containing heterocyclic group containing 2 to 4 nitrogen atoms such as homopiperazinediyl (homopiperazine-1,4-diyl, etc), 2,3-dehydrohomopiperazinediyl and the like, and a divalent 8-membered nitrogen-containing heterocyclic group containing 2 to 4 nitrogen atoms such as 1,4-diazacyclooctanediyl (1,4-diazacyclooctane-1,4-diyl, etc), 1,5-diazacyclooctanediyl (1,5-diazacyclooctane-1,5-diyl, etc.), and the like.

These "divalent nitrogen-containing heterocyclic groups" have the oxo group at a possible replaceable position and, inter alia, it is preferable that it is a "divalent 6- to 8-membered nitrogen-containing cyclic amido group" having the oxo group on the carbon atom adjacent to the nitrogen atom to which a group represented by the formula —CH($R^2$)— is bound. Examples of the "divalent 6- to 8-membered nitrogen-containing cyclic amido group" include 2-oxopiperazin-1,4-diyl, 2-oxo-1,2,3,4-tetrahydropyrazin-1,4-diyl, 2-oxohomopiperazin-1,4-diyl, 5-oxohomopiperazin-1,4-diyl, 2-oxo-1,4-diazacyclooctan-1,4-diyl, 5-oxo-1,4-diazacyclooctan-1,4-diyl, 2-oxo-1,5-diazacyclooctan-1,5-diyl, 5-oxo-2,3-dehydrohomopiperazin-1,4-diyl, 3-oxo-1,2,4-triazacyclohexan-1,4-diyl, 3-oxo-1,2,3,4-tetrahydro-1,2,4-triaziyn-1,4-diyl, 6-oxo-1,2,4-triazacyclohexan-1,4-diyl, 3-oxo-1,2,4,5-tetraazacyclohexan-1,4-diyl, and the like.

Examples of the substituent for the "nitrogen-containing heterocyclic ring" in the "nitrogen-containing heterocyclic ring which is substituted with an oxo group and may be further substituted" represented by ring A include, in addition to one oxo group, an optionally substituted hydroxy group, an optionally substituted mercapto group, a halogen atom (e.g. fluorine, chlorine, bromine, iodine, etc.), a nitro group, a cyano group, an oxo group, an optionally substituted amino group, an optionally substituted lower alkyl group, an optionally substituted lower alkylidene group, an optionally substituted lower aralkylidene group, a lower alkoxy group optionally substituted with 1 to 5 halogen atom(s) (e.g. fluorine, chlorine, bromine, iodine, etc.), an optionally esterified carboxyl group, an optionally substituted carbamoyl group, an optionally substituted thiocarbamoyl group, an optionally substituted sulfamoyl group, and the like, and these optional substituents may occur 1 to 3 (preferably 1 to 2) times at any possible position(s).

Here, examples of the substituent for the "optionally substituted amino group" include 1 to 2 optionally substituted alkyl group(s), optionally substituted carbamoyl group(s), optionally substituted thiocarbamoyl group(s), optionally substituted sulfamoyl group(s), optionally esterified carboxyl group(s), sulfonic acid-derived acyl group(s), carboxylic acid-derived acyl group(s) and the like.

Examples of the "optionally substituted alkyl group", the "optionally substituted carbamoyl group", the "optionally substituted thiocarbamoyl group", the "optionally substituted sulfamoyl group", the "optionally esterified carboxyl group", the "sulfonic acid-derived acyl group" and the "carboxylic acid-derived acyl group" include the same "optionally substituted alkyl group", "optionally substituted carbamoyl group", "optionally substituted thiocarbamoyl group", "optionally substituted sufamoyl group", "optionally esterified carboxyl group", "sulfonic acid-derived acyl group" and "carboxylic acid-derived acyl group" as those of the substituent for a group represented by $R^1$, and preferred examples of the "optionally substituted amino group" include amino optionally having 1 to 2 substituent(s) selected from (1) lower ($C_{1-6}$) alkyl groups such as methyl, ethyl, n-propyl, isopropyl, n-butyl, isobutyl, sec-butyl, tert-butyl and the like, (2) a mono- or di-lower ($C_{1-6}$) alkylcarbamoyl group, (3) a $C_{1-6}$ alkylsulfonyl such as methanesulfonyl, ethanesufonyl, and the like, (4) a $C_{1-6}$ alkanoyl such as formyl, acetyl, propionyl, pivaloyl and the like and (5) benzoyl, and the like.

Examples of the lower alkyl group in the "optionally substituted lower alkyl group" include a $C_{1-6}$ alkyl group such as methyl, ethyl, n-propyl, isopropyl, n-butyl, isobutyl, sec-butyl, tert-butyl, and the like and, in particular, methyl, ethyl, and the like are preferable. Examples of the substituent therefor include a halogen atom (e.g. fluorine, chlorine, bromine, iodine etc.), an amino group, a carboxyl group, a hydroxy group, $C_{6-10}$ aryl, $C_{6-10}$ aryloxy, $C_{6-10}$ aryl-$C_{1-4}$ alkoxy, and the like, and these optional substituents may occur 1 to 5 (preferably 1 or 2) times at any possible replaceable position(s).

Examples of the "optionally substituted lower alkylidene group" include $C_{1-6}$ alkylidene such as methylidene, ethylidene, and the like, examples of the substituent therefor include a halogen atom (e.g. fluorine, chlorine, bromine, iodine etc.), an amino group, a carboxyl group, a hydroxy group, and the like, and these optional substituents may occur 1 to 5 (preferably 1 or 2) times at any possible position(s).

Examples of the "optionally substituted lower aralkylidene group" include $C_{6-10}$ aryl-$C_{1-4}$ alkylidene such as benzylidene, and the like, examples of the substituent therefor include a halogen atom (e.g. fluorine, chlorine, bromine, iodine, etc.), an amino group, a carboxyl group, a hydroxy group and the like, and these optional substituents may occur 1 to 5 (preferably 1 or 2) times at any possible position(s).

Examples of the lower alkoxy group in the "lower alkoxy group optionally substituted with a halogen atom" include $C_{1-6}$ alkoxy groups such as methoxy, ethoxy, n-propoxy, isopropoxy, n-butoxy, isobutoxy, sec-butoxy, tert-butoxy, and the like and, in particular, methoxy, ethoxy, and the like are preferable.

Examples of the "optionally esterified carboxyl group" include the same optionally esterified carboxyl groups as those of the substituent for the above-mentioned group represented by $R^1$.

Examples of the "optionally substituted carbamoyl group", the "optionally substituted thiocarbamoyl group" and the "optionally substituted sulfamoyl group" include the same optionally substituted carbamoyl group, optionally substituted thiocarbamoyl group and optionally substituted sulfamoyl group as those of the substituent for the above-mentioned group represented by $R^1$.

In the "optionally substituted hydroxy group" and the "optionally substituted mercapto group" as the substituent which may be possessed by the "nitrogen-containing heterocyclic ring which is substituted with an oxo group and may be further substituted" represented by ring A, examples of the substituent which may be possessed by the "hydroxy group" and the "mercapto group" include an optionally substituted lower alkyl group, an optionally esterified carboxyl group, an optionally substituted carbamoyl group, an optionally substituted thiocarbamoyl group, an optionally substituted sulfamoyl group, a sulfonic acid-derived acyl group, a carboxylic acid-derived acyl group, and the like. Examples of the lower alkyl group include a $C_{1-6}$ alkyl group such as methyl, ethyl, n-propyl, isopropyl, n-butyl, isobutyl, sec-butyl, tert-butyl, pentyl, hexyl, and the like, and examples of the substituent which may be possessed by the lower alkyl group include a halogen group (e.g. fluorine, chlorine, bromine, iodine, etc.), an optionally substituted aryl group [for example, phenyl or naphthyl each optionally substituted with a halogen atom (e.g. fluorine, chlorine, bromine, iodine, etc.), a lower alkyl group (e.g. $C_{1-6}$ alkyl groups such as methyl, ethyl, n-propyl, isopropyl, n-butyl, isobutyl, sec-butyl, tert-butyl, pentyl, hexyl, etc.), a lower alkoxy group (e.g. $C_{1-6}$ alkoxy groups such as methoxy, ethoxy, n-propoxy, isopropoxy, n-butoxy, isobutoxy, sec-butoxy, tert-butoxy, etc.), and the like], an optionally substituted hydroxy group (e.g. the same optionally substituted hydroxy group as that of the substituent for the above-mentioned group represented by $R^1$), an optionally substituted thiol group (e.g. the same optionally substituted thiol group as that of the substituent for the above-mentioned group represented by $R^1$), an optionally substituted amino group (e.g. the same optionally substituted amino group as that of the substituent for the above-mentioned group represented by $R^1$), an optionally esterified carboxyl group (e.g. the same optionally esterified carboxyl group as that of the substituent for the above-mentioned group represented by $R^1$), and the like. Further, in the "optionally substituted mercapto group", the sulfur atom may be oxidized and, for example, may have a structure represented by $S(O)_k$ [k denotes an integer of 0 to 2].

In the "optionally substituted hydroxy group" and the "optionally substituted mercapto group" as the substituent which may be possessed by the "nitrogen-containing heterocyclic ring which is substituted with an oxo group and may be further substituted" represented by ring A, examples of the "optionally esterified carboxyl group", the "optionally substituted carbamoyl group", the "optionally substituted thiocarbamoyl group", the "optionally substituted sulfamoyl group", the "sulfonic acid-derived acyl group" and the "carboxylic acid-derived acyl group" as the substituent which may be possessed by the "hydroxy group" and the "mercapto group" include the same "optionally esterified carboxyl group", "optionally substituted carbamoyl group", "optionally substituted thiocarbamoyl group", "optionally substituted sulfamoyl group", "sulfonic acid-derived acyl group" and "carboxylic acid-derived acyl group" as those of the substituent for the above-mentioned group represented by $R^1$.

As ring A, for example, a ring represented by the formula:

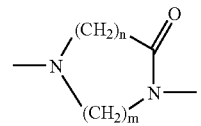

wherein n denotes 1 or 2, and m denotes 2 or 3, and the like are preferable.

In the above-mentioned formula, as m, 2 is preferable and, as n, 1 is preferable.

In addition, as ring A, an optionally substituted oxopiperazine ring or an optionally substituted oxohomopiperazine ring is preferable and, inter alia, an optionally substituted oxopiperazine ring is preferable. In addition, when expressed as a divalent group, inter alia, 2-oxopiperazin-1,4-diyl can be preferably used.

In the above-mentioned formula, $R^2$ denotes a hydrogen atom, an optionally substituted $C_{1-4}$ alkyl group, an optionally esterified carboxyl group, or a cyano group.

Examples of the "$C_{1-4}$ alkyl group" in the "optionally substituted $C_{1-4}$ alkyl group" represented by $R^2$ include methyl, ethyl, n-propyl, isopropyl, n-butyl, isobutyl, sec-butyl, tert-butyl, and the like, and examples of the substituent which may be possessed by the "$C_{1-4}$ alkyl group" include the same substituents as those for the "optionally substituted lower alkyl group" as the substituent for the above-mentioned "divalent nitrogen-containing heterocyclic group which may be further substituted" represented by ring A.

Examples of the "optionally esterified carboxyl group" represented by $R^2$ include the same "optionally esterified carboxyl groups" as the substituent for the above-mentioned group represented by $R^1$.

As $R^2$, a hydrogen atom is preferably used.

In the above-mentioned formula, $R^3$ denotes a $C_{1-4}$ alkyl group or a $C_{2-4}$ alkenyl group, each of which may be substituted with a substituent selected from a halogen atom, a hydroxy group, an optionally substituted alkoxy group, an optionally substituted amino group and an optionally esterified carboxyl group.

Examples of the "$C_{1-4}$ alkyl group" in the "optionally substituted $C_{1-4}$ alkyl group" represented $R^3$ include methyl, ethyl, n-propyl, isopropyl, cyclopropyl, n-butyl, isobutyl, sec-butyl, tert-butyl, cyclobutyl, and the like.

Examples of the "$C_{2-4}$ alkenyl group" (preferably $C_{3-4}$ alkenyl") in the "optionally substituted $C_{2-4}$ alkenyl group" represented by $R^3$ include allyl, 2-butenyl, 3-butenyl, and the like.

Examples of the "optionally substituted alkoxy group" as the substituent for the "optionally substituted $C_{1-4}$ alkyl group" and the "optionally substituted $C_{2-4}$ alkenyl group" represented by $R^3$ include a $C_{1-6}$ alkoxy group (e.g. methoxy, ethoxy, n-propoxy, isopropoxy, n-butoxy, isobutoxy, sec-butoxy, tert-butoxy, etc.) optionally substituted with a substituent selected from (1) a hydroxy group, (2) an optionally substituted amino group [the amino group may have 1 or 2 substituent(s) such as a lower alkyl group (e.g. $C_{1-6}$ alkyl group such as methyl, ethyl, propyl, isopropyl, butyl, isobutyl, t-butyl, pentyl, hexyl, etc.), an acyl group (e.g. $C_{1-6}$ alkanoyl (e.g. formyl, acetyl, propionyl, pivaloyl, etc.), $C_{1-6}$ alkylsulfonyl (e.g. methanesulfonyl, ethanesulfonyl, etc.), benzoyl, benzenesulfonyl, etc.), a carboxyl group, a $C_{1-6}$-alkoxy-carbonyl group, and the like] (3) a halogen atom (e.g. fluorine, chlorine, bromine, iodine, etc.) (4) a nitro group, (5) a cyano group, (6) a lower ($C_{1-6}$) alkyl group optionally substituted with 1 to 5 halogen atom(s) (e.g. fluorine, chlorine, bromine, iodine, etc.), (7) a lower ($C_{1-6}$) alkoxy group optionally substituted with 1 to 5 halogen atom(s) (e.g. fluorine, chlorine, bromine, iodine, etc.), and the like.

Examples of the "optionally substituted amino group" as the substituent for the "optionally substituted $C_{1-4}$ alkyl group" and the "optionally substituted $C_{2-4}$ alkenyl group" represented by $R^3$ include the same "optionally substituted amino groups" as those of the substituent which may be possessed by a group represented by $R^1$.

Examples of the "optionally esterified carboxy group" as the substituent for the "optionally substituted $C_{1-4}$ alkyl group" and the "optionally substituted $C_{2-4}$ alkenyl group" represented by $R^3$ include the same "optionally esterified carboxyl groups" as those of the substituent for the above-mentioned group represented by $R^1$.

As $R^3$, a $C_{1-4}$ alkyl group (preferably, a $C_{1-3}$ alkyl group), etc., is preferable and, inter alia, methyl or ethyl is preferably used.

In the above-mentioned formulas, Z denotes (1) an optionally substituted amino group, (2) an optionally substituted hydrocarbon group, (3) an optionally substituted imidoyl group or (4) an optionally substituted nitrogen-containing heterocyclic group.

Examples of the substituent in the "optionally substituted amino group" represented by Z include an "optionally substituted hydrocarbon group" and an "optionally substituted heterocyclic group", while two substituents may be taken together with the nitrogen atom to form a cyclic amino group. Examples of the cyclic amino is group in such the case include a 3- to 8-membered (preferably 5- to 6-membered) cyclic amino such as 1-azetidinyl, 1-pyrrolidinyl, piperidino, morpholino, 1-piperazinyl, 1-piperazinyl optionally having at the 4-position a lower alkyl group (e.g. $C_{1-6}$ alkyl group such as methyl, ethyl, propyl, isopropyl, butyl, t-butyl, pentyl, hexyl, etc.), an aralkyl group (e.g. $C_{7-10}$ aralkyl group such as benzyl, phenethyl, etc.), an aryl group (e.g. $C_{6-10}$ aryl group such as phenyl, 1-naphthyl, 2-naphthyl, etc.), and the like, and such the cyclic amino group may have the same number of the same substituents as those of the "optionally substituted hydrocarbon group" as the substituent in the above-mentioned "optionally substituted amino group" represented by Z.

Examples of the "optionally substituted hydrocarbon group" as the substituent in the "optionally substituted amino group" represented by Z include an aliphatic chain-like hydrocarbon group, an alicyclic hydrocarbon group and an aryl group and, inter alia, an aryl group is preferable.

Examples of the "aliphatic chain-like hydrocarbon group" as an example of the hydrocarbon group include a straight or branched aliphatic hydrocarbon group such as an alkyl group, an alkenyl group, an alkynyl group, and the like.

Here examples of the alkyl group include a $C_{1-10}$ alkyl group (preferably $C_{1-6}$ alkyl, etc.) such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethypropyl, 2-ethylbutyl, n-heptyl, 1-methyheptyl, 1-ethylhexyl, n-octyl, 1-methylheptyl, nonyl, and the like.

Examples of the alkenyl group include a $C_{2-6}$ alkenyl group such as vinyl, allyl, isopropenyl, 2-methyallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, and the like.

Examples of the alkynyl group include a $C_{2-6}$ alkynyl group such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, and the like.

Examples of the "alicyclic hydrocarbon group" as an example of the hydrocarbon group include a saturated or unsaturated alicyclic hydrocarbon group such as a cycloalkyl group, a cycloalkenyl group, a cycloalkadienyl group, and the like.

Here, examples of the "cycloalkyl group" include $C_{3-9}$ cycloalkyl such as cyclopropyl, cyclobutyl, cyclopentyl, cyclohexyl, cycloheptyl, cyclooctyl, cyclononyl, and the like.

Examples of the "cycloalkenyl group" include a $C_{3-6}$ cycloalkenyl group such as 2-cyclopenten-1-yl, 3-cyclopenten-1-yl, 2-cyclohexen-1-yl, 3-cyclohexen-1-yl, 1-cyclobuten-1-yl, 1-cyclopenten-1-yl, and the like.

Examples of the "cycloalkadienyl group" include a $C_{4-6}$ cycloalkadienyl group such as 2,4-cyclopentadien-1-yl, 2,4-cyclohexadien-1-yl, 2,5-cyclohexadien-1-yl, and the like.

Examples of the "aryl group" as an example of the hydrocarbon group include monocyclic or fused polycyclic aromatic hydrocarbon groups, for example, $C_{6-14}$ aryl groups such as phenyl, naphthyl, anthryl, phenanthryl, acenaphthylenyl, and the like and, inter alia, phenyl, 1-naphthyl, 2-naphthyl, and the like are particularly preferable.

Examples of the "optionally substituted heterocyclic group" as the substituent in the "optionally substituted amino group" represented by Z include an aromatic heterocyclic group, a saturated or unsaturated aromatic heterocyclic group (aliphatic heterocyclic group), and the like containing at least 1 (preferably 1 to 4, more preferable 1 or 2) of 1 to 3 kinds (preferably 1 to 2 kinds) of hetero atoms selected from an oxygen atom, a sulfur atom, and a nitrogen atom as an atom constituting a ring system (ring atom).

Examples of the "aromatic heterocyclic group" include a 5- to 6-membered aromatic monocyclic heterocyclic group such as an aromatic monocyclic heterocyclic group (e.g. furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc.) and 8- to 16-membered (preferably 8- to 12-membered) aromatic fused heterocyclic groups such as an aromatic fused heterocyclic group (e.g. benzofuranyl, isobenzofuranyl, benzo[b]thienyl, indolyl, isoindolyl, 1H-indazolyl, benzindazolyl, benzoxazolyl, 1,2-benzoisoxazoly, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthylidinyl, pyrinyl, pteridinyl, carbazolyl, α-carbolinyl, β-carbolinyl, γ-carbolinyl, acridinyl, phenoxazinyl, phenothiazinyl, phenazinyl, phenoxathynyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.) (preferably a heterocyclic ring in which one to two (preferably one) the above-mentioned 5- to 6-membered aromatic monocyclic heterocyclic group(s) is (are) fused with one to two (preferably one) benzene ring(s) or a heterocyclic ring in which two to three (preferably two) the above-mentioned same or different 5- to 6-membered aromatic monocyclic heterocyclic groups are fused, more preferably, a heterocyclic ring in which the above-mentioned 5- to 6-membered aromatic monocyclic heterocyclic group is fused with a benzene ring, particularly preferably, benzofuranyl, benzopyranyl, etc.), and the like.

Examples of the "non-aromatic heterocyclic group" include a 3- to 8-membered (preferably 5- to 6-membered) saturated or unsaturated (preferably saturated) non-aromatic heterocyclic group (aliphatic heterocyclic group) such as oxiranyl, azetidinyl, oxetanyl, thietanyl, pyrrolidinyl, tetrahydrofuryl, thioranyl, piperidyl, tetrahydropyranyl, morpholinyl, thiomorpholinyl, piperazinyl, and the like, and a non-aromatic heterocyclic group in which a part or all of double bonds of the above-mentioned aromatic monocyclic heterocyclic group or aromatic fused heterocyclic group are saturated, such as 1,2,3,4-tetrahydroquinolyl, 1,2,3,4-tetrahydroisoquinolyl, and the like.

Examples of the substituent for the "optionally substituted hydrocarbon group" and the "optionally substituted heterocyclic group" as the substituent in the "optionally substituted amino group" represented by Z include the same substituents as those which may be possessed by a group represented by $R^1$.

In addition, when the "optionally substituted hydrocarbon group" as the substituent in the "amino group substituted with an optionally substituted hydrocarbon group" represented by Z contains an "optionally substituted imino group" at the α-position, the "optionally substituted amino group" represented by Z forms an amino group substituted with an "optionally substituted imidoyl group" represented by Z described hereinafter, and for example, a group represented by the formula —N(R")—C(R')=N—R [wherein R" denotes a hydrogen atom or an optionally substituted hydrocarbon group, R denotes a hydrogen atom, an optionally substituted hydroxy group, an optionally substituted hydrocarbon group or a carboxylic acid-derived acyl group, and R' denotes a hydrogen atom, an optionally substituted hydrocarbon group, a carboxylic acid-derived acyl group, an optionally substituted amino group, an optionally substituted mercapto group or an optionally substituted hydroxy group], or the like is also included in the "optionally substituted amino group" represented by Z. In addition, when R' denotes a mercapto group or a hydroxy group and R denotes a hydrogen atom in the "optionally substituted imidoyl group", the "optionally substituted imidoyl group" may denote a group represented by the formula —C(=O)—NH$_2$ or —C(=S)—NH$_2$.

Examples of the "optionally substituted hydrocarbon group" represented by R, R' and R" in the above-mentioned formulas include the same "optionally substituted hydrocarbon groups" as those of the substituent in the above-mentioned "optionally substituted amino group" represented by Z; examples of the "carboxylic acid-derived acyl group" represented by R and R' include the same "carboxylic acid-derived acyl groups" as those of the substituent which may be possessed by the above-mentioned group represented by R'; examples of the "optionally substituted hydroxy group" represented by R' include the same "optionally substituted hydroxy group" as that of the substituent which may be possessed by the above-mentioned group represented by $R^1$; examples of the "optionally substituted amino group" represented by R' include the same "optionally substituted amino groups" as those of the substituent which may be possessed by the above-mentioned group represented by $R^1$, or an amino group optionally having 1 to 2 "optionally substituted hydrocarbon group(s)" as a substituent in the above-mentioned "optionally substituted amino group" represented by Z; and the like.

In the compound represented by the formula (I), the compound wherein R is a carboxylic acid-derived acyl group is useful as a prodrug of the compound wherein R is a hydrogen atom.

Examples of the "carboxylic acid-derived acyl group" represented by R include the same "carboxylic acid-derived acyl groups" as that of the substituent which may be possessed by the above-mentioned group represented by $R^1$, and the "carboxylic acid-derived acyl group" represented by R may be an optionally esterified carboxyl group such as a group represented by the formula —COOR'" [wherein R'" denotes an optionally substituted hydrocarbon group], and the like.

Examples of the "optionally substituted hydrocarbon group" represented by R'" include the same "optionally substituted hydrocarbon groups" as those of the substituent in the above-mentioned "optionally substituted amino group" represented by Z.

Preferable examples of the "hydrocarbon group" in the "optionally substituted hydrocarbon group" represented by R'" include $C_{1-6}$ alkyl, $C_{2-6}$ alkenyl, $C_{3-6}$ cycloalkyl, $C_{6-10}$ aryl, $C_{6-10}$ aryl-$C_{1-4}$ alkyl, and the like. Examples of the substituent which may be possessed by the "hydrocarbon group" include the same number of the same substituents as those which may be possessed by the above-mentioned group represented by $R^1$.

Examples of the group represented by the formula —COOR'" include, inter alia, a $C_{1-6}$ alkoxy-carbonyl group (e.g. methoxycarbonyl, ethoxycarbonyl, isopropoxycarbonyl, etc.), a $C_{1-6}$ alkanoyloxy-$C_{1-6}$ alkoxy-carbonyl group (e.g. pivaloyloxymethoxycarbonyl, 1-(acetoxy)ethoxycarbonyl, acetoxy-tert-butoxycarbonyl, etc.), a $C_{1-6}$ alkoxycarbonyloxy-$C_{1-6}$ alkoxy-carbonyl group (e.g. ethoxycarbonyloxymethoxycarbonyl, etc.), a 5-$C_{1-4}$ alkyl-2-oxodioxolen-4-yl-$C_{1-6}$ alkoxy-carbonyl group (e.g. 5-methyl-2-oxo-dioxolen-4-ylmethoxycarbonyl, etc.), and the like.

As the "optionally substituted amino group" represented by Z, more specifically, for example, there can be used an amino group, a mono- or di-lower ($C_{1-6}$) alkyl amino group (e.g. methylamino, ethylamino, benzylmethylamino, dimethylamino, diethylamino, diisobutylamino, diisopropylamino, N-ethyl-t-butylamino, benzylmethylamino, etc.) which may be further substituted with a $C_{6-10}$ aryl group (preferably phenyl), or the like, a group represented by the formula —N(R")—C(R')=N—R [wherein R" denotes a hydrogen atom or an optionally substituted hydrocarbon group (preferably, a hydrogen atom or a lower ($C_{1-6}$) alkyl group; more preferably, a hydrogen atom), R denotes a hydrogen atom, an optionally substituted hydroxy group, an optionally substituted hydrocarbon group or a carboxylic acid-derived acyl group (preferably, a hydrogen atom or a carboxylic acid-derived acyl group), and R' denotes a hydrogen atom, an optionally substituted hydrocarbon group, an optionally substituted amino group, an optionally substituted mercapto group or an optionally substituted hydroxy group (preferably, a hydrogen atom, a lower ($C_{1-6}$) alkyl group, an amino group or a mono- or di-lower ($C_{1-6}$) alkyl amino group)] (e.g. a guanidino group, a formimidoylamino group, an acetoimidoylamino group etc.), a 5- to 6-membered cyclic amino group (e.g. a piperidino group, etc.), and the like.

As the "optionally substituted hydrocarbon group" represented by Z, the optionally substituted hydrocarbon group as the substituent in the above-mentioned "optionally substituted amino group" represented by Z can be applied as such. Among them, bulky alkyl groups such as isopropyl, cyclopropyl, 2-butyl, tert-butyl, 3-pentyl, and the like are preferable.

Examples of the "optionally substituted imidoyl group" represented by Z include a group represented by the formula —C(R')=N—R [wherein the symbols are as defined above], and the like.

Here, when R' denotes the optionally substituted amino group (preferably amino, methylamino, ethylamino, propylamino, dimethylamino, diethylamino, hydrazino, piperidino, piperazino, morpholino, thiomorpholino, etc.), the "optionally substituted imidoyl group" represented by Z forms an optionally substituted amidino group. Specific examples of such the optionally substituted amidino group include an amidino group which may be substituted with 1 to 2 lower ($C_{1-6}$) alkyl group(s), lower ($C_{1-6}$) alkanoyl group(s), benzoyl group(s), or the like (e.g. amidino, N-methylamidino, N-ethylamidino, N-propylamidino, N,N'-dimethylamidino, N,N'-diethylamidino, N-methyl-N'-diethylamidino, N-formylamidino, N-acetylamidino, etc.).

In the above-mentioned formulas, preferable examples of R include hydrogen, a lower alkyl group (e.g. a $C_{1-6}$ alkyl group such as methyl, ethyl, propyl, isopropyl, butyl, isobutyl, etc.), an acyl group (e.g. a $C_{1-6}$ alkanoyl group such as formyl, acetyl, propionyl, pivaloyl, etc.; benzoyl; $C_{1-8}$ alkoxy-carbonyl such as methoxycarbonyl, ethoxycarbonyl, propoxycarbonyl, isopropoxycarbonyl, butoxycarbonyl, isobutoxycarbonyl, etc.; $C_{7-10}$ aralkyloxy-carbonyl such as benzyloxycarbonyl, phenethyloxycarbonyl, etc.), a hydroxy group, and the like, and preferable examples of R' include hydrogen, a lower alkyl group ($C_{1-6}$ alkyl groups such as methyl, ethyl, propyl, isopropyl, butyl, isobutyl, etc.), an optionally substituted amino group (e.g. an amino group which may be substituted with 1 to 2 the same or different lower alkyl group(s) (e.g. a $C_{1-6}$ alkyl group such as methyl, ethyl, propyl, isopropyl, butyl, isobutyl, etc.) or acyl group(s) (e.g. $C_{1-6}$ alkanoyl (e.g. formyl, acetyl, propionyl, pivaloyl, etc.), $C_{1-6}$ alkanesulfonyl (e.g. methanesulfonyl, ethanesulfonyl, etc.), benzoyl, benzenesulfonyl, etc.), a hydrazino group, a 5- to 6-membered cyclic amino group (e.g. piperidino, thiomorpholino, morpholino, piperazino, etc.), etc.), a hydroxy group, a lower alkoxy group (e.g. a $C_{1-6}$ alkoxy group such as methoxy, ethoxy, propoxy, isopropoxy, butoxy, isobutoxy, etc.).

In the above-mentioned formulas, as R, hydrogen is preferable.

In the above-mentioned formulas, as R', hydrogen, a lower alkyl group or an optionally substituted amino group is preferable and, inter alia, a lower alkyl group or an optionally substituted amino group is preferable and, inter alia, an optionally substituted amino group (preferably, amino optionally substituted with $C_{1-4}$ alkyl) is preferable.

Examples of the "nitrogen-containing heterocyclic group" in the "optionally substituted nitrogen-containing heterocyclic group" represented by Z include an aromatic nitrogen-containing heterocyclic group and a saturated or unsaturated non-aromatic nitrogen-containing heterocyclic group (aliphatic heterocyclic groups) containing, as an atom constituting a ring system (ring atom), at least 1 (preferable 1 to 4, more preferable 1 to 3) nitrogen atom in addition to carbon atoms and, optionally, 1 to 3 hetero atoms selected from an oxygen and a sulfur atom, and the like.

Examples of the "aromatic nitrogen-containing heterocyclic group" include an aromatic monocyclic nitrogen-containing heterocyclic group such as pyrrolyl, oxazolyl, isoxazolyl, thiazolyl, isothiazolyl, imidazolyl (1H-imidazol-1-yl, 1H-imidazol-4-yl, etc.), pyrazolyl, 1,2,3-oxathiazolyl, 1,2,4-oxathiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl (1,2,4-triazolyl-1-yl, 1,2,4-triazolyl-4-yl, etc.), tetrazolyl, pyridyl (2-, 3- or 4-pyridyl), pyridazinyl, pyrimidinyl, pyrazinyl, triazinyl, and the like, and N-oxide thereof, a 8- to 16-membered (preferably 8- to 12-membered) aromatic fused nitrogen-containing heterocyclic group such as indolyl, isoindolyl, 1H-indazolyl, benzindazolyl, benzoxazolyl, 1,2-benzoisoxazoly, benzothiazolyl, benzopyranyl, 1,2-benzoisothiazolyl, 1H-benzotriazolyl, quinolyl, isoquinolyl, cinnolinyl, quinazolinyl, quinoxalinyl, futarazinyl, naphthylidinyl, purinyl, pteridinyl, carbazolyl, α-carbolyl, β-carbolyl, γ-carbolyl, acridinyl, phenoxazinyl, phenothiazinyl, phenazinyl, phenathrydinyl, phenathrolinyl, indolidinyl, pyrrolo(1,2-b)pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, and the like, and N-oxide thereof (preferably a heterocyclic ring in which one to two (preferably one) the above-mentioned 5- to 6-membered aromatic monocyclic nitrogen-containing heterocyclic group(s) is (are) fused with one to two (preferably one) benzene ring(s), or a heterocyclic ring in which two to three (preferably two) the same or different above-mentioned 5- to 6-membered aromatic monocyclic nitrogen-containing heterocyclic groups are fused, more preferably a heterocyclic ring in which the above-mentioned 5- to 6-membered aromatic monocyclic nitrogen-containing heterocyclic group is fused with a benzene ring, etc.) and, inter alia, a 5- to 6-membered aromatic monocyclic nitrogen-containing heterocyclic group is preferable and, inter alia, imidazolyl and pyridyl are preferable.

Examples of the "non-aromatic nitrogen-containing heterocyclic group" include, in addition to the partially reduced "aromatic nitrogen-containing heterocyclic group" described above (e.g. imidazolinyl, tetrahydropyrimidinyl, etc.), azetidinyl, pyrrolidinyl, piperidyl (2-, 3- or 4-piperidyl), morpholinyl, thiomorpholinyl, piperazinyl (1-piperazinyl etc.), homopiperazinyl, and the like and, inter alia, a 5- to 6-membered non-aromatic monocyclic nitrogen-containing heterocyclic group is preferable.

As the substituent for the "nitrogen-containing heterocyclic group" represented by Z, there can be used the same substituents as those for the "optionally substituted hydrocarbon group" as the substituent in the above-mentioned "optionally substituted amino group" represented by Z. In addition, the nitrogen atom constituting the nitrogen-containing heterocyclic group may be oxidized.

As Z, preferred are an optionally substituted nitrogen-containing heterocyclic group (preferably an optionally substituted aromatic nitrogen-containing heterocyclic group; more preferably, a 6-membered aromatic nitrogen-containing heterocyclic group such as an optionally substituted pyridyl group or an optionally substituted pyrimidinyl group; particularly preferable an optionally substituted pyridyl group), and the like and, inter alia, a nitrogen-containing heterocyclic group optionally substituted with a substituent selected from an optionally substituted $C_{1-4}$ alkyl group and an optionally substituted amino group, etc., is preferable.

In addition, as Z, an optionally substituted imidoyl group (preferably an optionally substituted $C_{1-4}$ imidoyl group), and an optionally substituted amidino group can also be preferably used.

As compound (I), 4-(6-chloronaphthalen-2-sulfonyl)-1-[4-methoxycarbonylamino-1-(4-pyridyl)piperidin-4-ylmethyl]-2-piperazinone, 4-(6-chloronaphthalen-2-sulfonyl)-1-[4-ethoxycarbonylamino-1-(4-pyridyl)piperidin-4-ylmethyl]-2-piperazinone, 4-(7-chloro-2H-benzopyran-3-sulfonyl)-1-[4-methoxycarbonylamino-1-(4-pyridyl)piperidin-4-ylmethyl]-2-piperazinone, 4-(7-chloro-2H-benzopyran-3-sulfonyl)-1-[4-ethoxycarbonylamino-1-(4-pyridyl)piperidin-4-ylmethyl]-2-piperazinone, 1-[4-methoxycarbonylamino-1-(4-pyridyl)piperidin-4-ylmethyl]-4-(4-vinylbenzenesulfonyl)-2-piperazinone, 1-[4-ethoxycarbonylamino-1-(4-pyridyl)piperidin-4-ylmethyl]-4-(4-vinylbenzenesulfonyl)-2-piperazinone, 1-[4-ethoxycarbonylamino-1-(1-methyl-4-pyridyl)piperidin-4-ylmethyl]-4-(4-vinylbenzenesulfonyl)-2-piperazinone, 1-[4-propoxycarbonylamino-1-(4-pyridyl)piperidin-4-ylmethyl]-4-(4-vinylbenzenesulfonyl)-2-piperazinone, 1-[4-ethoxycarbonylamino-1-(4-pyridyl)piperidin-4-ylmethyl]-4-(4-bromopenzenesulfonyl)-2-piperazinone, 1-[4-ethoxycarbonylamino-1-(2-methyl-4-pyridyl)piperidin-4-ylmethyl]-4-(4-bromobenzenesulfonyl)-2-piperazinone or a salt thereof is particularly preferably used.

A prodrug for compound (I) means a compound which is converted into compound (I) by a reaction with an enzyme or a gastric acid under in vivo physiological conditions, i.e. a compound which undergoes an enzymatic oxidation, reduction or hydrolysis to form compound (I) and a compound which is hydrolyzed by a gastric acid to form compound (I). A prodrug for compound (I) may for example be a compound resulting from acylation, alkylation or phosphorylation of amino group of compound (I) (for example, a compound resulting from eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, tert-butylation of an amino group of compound (I), etc.), a compound resulting from acylation, alkylation, phosphorylation and boration of hydroxyl group of compound (I) (for example, a compound resulting from acetylation, palmitoylation, propanoylation, pivaloylation, succinylation, fumarylation, alanylation, dimethylaminomethylcarbonylation of hydroxyl group of compound (I), etc.), or a compound resulting from esterification or amidation of carboxyl group of compound (I) (for example, a compound resulting from ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification, methylamidation of carboxyl group of compound (I), etc.), and the like. Any of these compounds can be produced from compound (I) by a method known per se.

A prodrug for compound (I) may also be a compound which is changed into compound (I) under physiological conditions described in "IYAKUHIN NO KAIHATSU (Pharmaceutical development)", Vol.7, Molecular design, p163–198, HIROKAWA SHOTEN, 1990.

A salt of compound (I) may for example be a pharmaceutically acceptable salt such as an acid addition salt with acetic acid, lactic acid, succinic acid, maleic acid, tartaric acid, citric acid, gluconic acid, ascorbic acid, benzoic acid, methanesulfonic acid, p-toluenesulfonic acid, cinnamic acid, fumaric acid, phosphonic acid, hydrochloric acid, nitric acid, hydrobromic acid, hydroiodic acid, sulfamic acid, sulfuric acid, and the like, a metal salt with sodium, potassium, magnesium, calcium, and the like, an organic salt with trimethylamine, triethylamine, pyridine, picolin, N-methylpyrrolidine, N-methylpiperidine, N-methylmorpholine, and the like.

Compound (I) or a salt thereof can be produced, for example, by the following methods A to C. Each of compounds described in the following reaction schemes may form a salt in so far as it does not interfere with the reaction and, as such a salt, there are the same salts as those of compound (I).

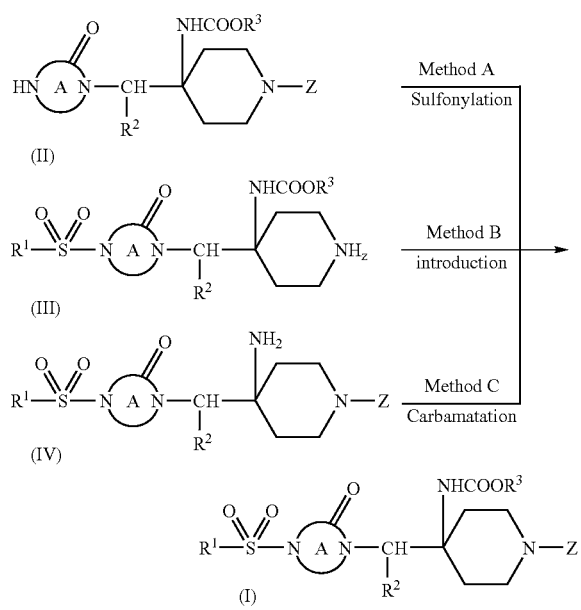

Method A

Compound (I) can be prepared by reacting a compound represented by the formula $R^1SO_2Q$ [wherein Q denotes a leaving group, and the other symbol is as defined above], or a salt thereof, with Compound (II) represented by the formula (II):

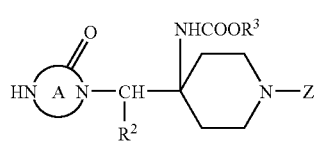

(II)

wherein the symbols are as defined above, or a salt thereof.

In the above formula, Q denotes a leaving group. Examples of the leaving group represented by Q include a halogen atom (e.g. fluorine, chlorine, bromine, iodine, etc.), and a group which form a reactive derivative of sulfonic acid (e.g. sulfonic anhydride, active sulfonic amide (e.g. 1,2,4-triazolide, imidazolide, etc.), quaternary aminesulfonyl (e.g. N-methylpyrrolidinium salt, etc.), bissulfonylimide (e.g. N-phenylbissulfonylimide etc.) etc.), and the like.

This method is carried out by reacting compound (II) or a salt thereof with a reactive derivative of sulfonic acid, and examples of a salt of compound (II) include an acid addition salt with an acid which form an acid addition salt with compound(I) as described above.

This sulfonating reaction is generally carried out in a solvent, and a solvent which dose not interfere with the reaction is appropriately selected. Examples of such solvent include alcohols such as methanol, ethanol, propanol, isopropanol, butanol, tert-butanol, and the like, ethers such as dioxane, tetrahydrofuran, diethyl ether, tert-butyl methyl ether, diisopropyl ether, ethylene glycol-dimethyl ether, and the like, esters such as ethyl formate, ethyl acetate, n-butyl acetate, and the like, halogenated hydrocarbons such as dichloromethane, chloroform, carbon tetrachloride, trichloroethylene, 1,2-dichloroethane, and the like, hydrocarbons such as n-hexane, benzene, toluene, and the like, amides such as formamide, N, N-dimethylformamide, N,N-dimethylacetamide, and the like, ketones such as acetone, methyl ethyl ketone, methyl isobutyl ketone, and the like, nitrites such as acetonitrile, propionitrile, and the like, as well as dimethyl sulfoxide, sulfolane, hexamethylphosphoramide, water and the like. They can be used alone or as a mixed solvent.

This reaction may be carried out in the presence of a base if necessary and, as such the base, there can be used inorganic bases such as lithium hydroxide, potassium hydroxide, sodium hydroxide, sodium carbonate, potassium carbonate, sodium bicarbonate, and the like, and tertiary amines such as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine, N-methylmorpholine, and the like.

In the reaction, about 1 to about 5 moles, preferably about 1 to about 3 moles of a reactive derivative of sulfonic acid is used per 1 mole of compound (II).

The reaction temperature is about −80° C. to about 100° C., preferably about −50° C. to about 80° C.

The reaction time varies depending on a kind of compound (II) or a reactive derivative of sulfonic acid, a kind of a solvent, a reaction temperature, and the like, but is usually about 1 minute to about 72 hours, preferably about 15 minutes to about 24 hours.

Method B

Compound (I) or a salt thereof can be prepared by reacting compound (III) represented by the formula (III):

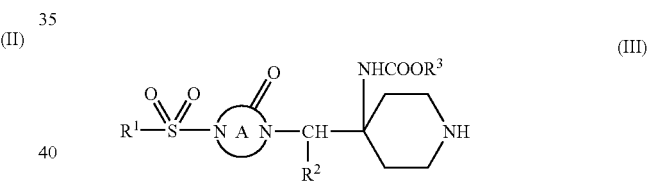

(III)

wherein the symbols are as defined above, or a salt thereof, with a compound represented by the formula $L^1$-Z [wherein the symbols are as defined above] or a salt thereof.

In the above-mentioned formula, the leaving group represented by $L^1$, when Z is an optionally substituted alkyl group or a nitrogen-containing heterocyclic ring, denotes a halogen atom, a group represented by the formula $R^7$—$SO_2$—O— (wherein $R^7$ denotes a lower alkyl group optionally substituted with a halogen atom or a phenyl group optionally having a substituent), or an atomic group being capable of cross coupling, for example, a group bound through boron, tin, magnesium, or the like; when Z is an optionally substituted amino group, $L^1$ denotes a group represented by $R^6$—$SO_2$—O— (wherein $R^6$ denotes a lower alkyl group optionally substituted with a halogen atom, a phenyl group optionally having a substituent, a hydroxy group, and the like) or $R^7$—P(O)—O— (wherein $R^7$ denotes a lower alkyl group optionally substituted with a halogen atom or a phenyl group optionally having a substituent); when Z is an optionally substituted amidino group or imidoyl group, $L^1$ denotes, for example, an optionally substituted lower alkoxy group (e.g. a $C_{1-6}$ alkoxy group optionally substituted with a halogen atom, etc.), an optionally substituted lower alkylthio group (e.g. a $C_{1-6}$ alkylthio group optionally substituted with a halogen atom, etc.), an optionally substituted lower alkylthionium group (e.g. a $C_{1-6}$ alkylthionium group optionally substituted with a halogen atom, etc.), or a pyrazolyl group optionally having a substituent, etc.

In the above-mentioned formula, examples of the lower alkyl group represented by $R^6$ and $R^7$ include a $C_{1-6}$ alkyl group such as methyl, ethyl, propyl, isopropyl, butyl, isobutyl, sec-butyl, tert-butyl, pentyl, isopentyl, neopentyl, hexyl, etc., and, inter alia, methyl, ethyl, propyl, isopropyl, butyl, etc., are preferably. Examples of the halogen atom include fluorine, chlorine, bromine, iodine, and the like, and these halogen atoms may occur 1 to 9 times, preferably 1 to 5 times at any possible position(s).

In the above-mentioned formula, examples of the substituent for the phenyl group optionally having a substituent represented by $R^6$ and $R^7$ include a lower alkyl group (e.g. a $C_{1-6}$ alkyl group such as methyl, ethyl, propyl, butyl, etc.), a lower alkoxy group (e.g. a $C_{1-6}$ alkoxy group such as methoxy, ethoxy, propoxy, butoxy, etc.), a halogen atom (e.g. fluorine, chlorine, bromine, iodine, etc.), a nitro group, a cyano group, a carboxyl group, etc.

This reaction is usually carried out in the presence of a base. As such base, preferably, there can be used, for example, inorganic bases such as an alkali metal hydride, e.g., sodium hydride, potassium hydride, etc., an alkali metal hydroxide, e.g., lithium hydroxide, sodium hydroxide, potassium hydroxide, etc., an alkaline earth metal hydroxide, e.g., magnesium hydroxide, calcium hydroxide, etc., an alkali metal carbonate, e.g., sodium carbonate, potassium carbonate, etc., an alkali metal bicarbonate, e.g., sodium bicarbonate, potassium bicarbonate, etc.; alkali metal salts of an organic acid such as an alkali metal acetate, e.g., sodium acetate, potassium acetate, etc.; an alkali metal alkoxides such as sodium methylate, potassium tert-butoxide, etc.; organic bases such as trimethylamine, triethylamine, diisopropylethylamine, pyridine, picoline, N-methylpyrrolidine, N-methylmorpholine, 1,5-diazabicyclo[4.3.0]non-5-en, 1,4-diazabicyclo[2.2.2]octane, 1,8-diazabicyclo[5.4.0]-7-undecene, etc.; lithium salts such as methyl lithium, n-butyrolithium, sec-butyrolithium, tert-butyrolithium, etc.; lithium amides such as lithium diisopropylamide, etc.; and the like.

This reaction is generally carried out in a solvent. As such solvent, the solvents described for Method A are used as such.

In the reaction, about 0.8 to 10 moles, preferably about 0.9 to 5 moles of the compound $L^1$-Z, and about 1 to about 100 moles, preferably about 1 to about 20 moles of the base are used per 1 mole of compound (III).

The reaction temperature is about −10° C. to about 250° C., preferably about −5° C. to about 200° C.

The reaction time varies depending on a kind of compound (III), the compound $L^1$-Z, the base or the solvent, the reaction temperature, and the like, but is usually about 1 minute to about 200 hours, preferably about 5 minutes to about 100 hours.

This reaction can be accelerated by using a metal catalyst if necessary. As such metal catalyst, for example, there can be used a palladium compound [e.g. palladium acetate, tetrakis(triphenylphosphine)palladium, bis(triphenylphosphine)palladium chloride, dichlorobis(triethylphosphine) palladium, tris(dibenzylideneacetone)dipalladium-2,2'-bis(diphenylphosphino)-1,1'-binaphthyl, etc.], a nickel compound [e.g. tetrakis(triphenylphosphine)nickel, bis(triethylphosphine)nickel chloride, bis(triphenylphosphine) nickel chloride, etc.], a rhodium compound [e.g. tri(triphenylphosphine)rhodium chloride, etc.], and the like, inter alia, a palladium compound is preferable. The amount of these catalysts to be used is about 10 to 0.000001 mole, preferably about 1 to 0.001 mole per 1 mole of compound (III).

Further, this reaction may be carried out in a sealed tube.

Method C

Compound (I) or a salt thereof can be prepared by reacting compound (IV) represented by the formula (IV):

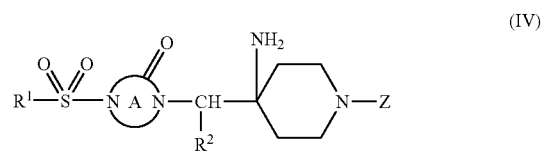

wherein the symbols are as defined above, or a salt thereof with a compound represented by a formula $L^2$-COOR$^3$ wherein the symbols are as defined above, or a salt thereof.

In the above-mentioned formula, the leaving group represented by $L^2$ denotes a halogen atom, a phenoxy group optionally having a substituent, an optionally substituted lower ($C_{1-6}$) alkoxy group, a cyano group, an imidazolyl group having a substituent or an imidazolium group.

This reaction is usually carried out in the presence of a base. As such base, bases described for Method B are used as such.

This reaction is generally carried out in a solvent. As such solvent, solvents described for Method A are used as such.

In the reaction, about 0.8 to 10 moles, preferably about 0.9 to 5 moles of the compound $L^2$-COOR$^3$, and about 1 to about 100 moles, preferably about 1 to about 20 moles of the base are used per 1 mole of compound (IV).

The reaction temperature is about −10° C. to about 250° C., preferably about −5° C. to about 200° C.

The reaction time varies depending on a kind of compound (IV), the compound $L^2$-COOR$^3$, the base or the solvent, the reaction temperature and the like, and is usually about 1 minute to about 200 hours preferably about 5 minutes to about 100 hours.

Starting compounds (II), (II) and (IV) which are used in the above-mentioned preparing Methods A to C can be prepared, for example, by a known per se method or a similar method as shown below.

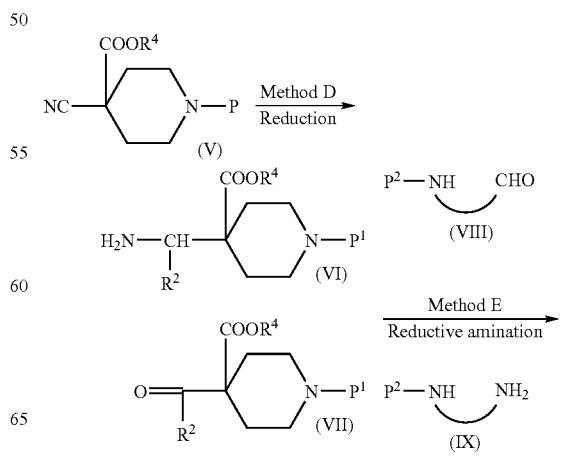

-continued

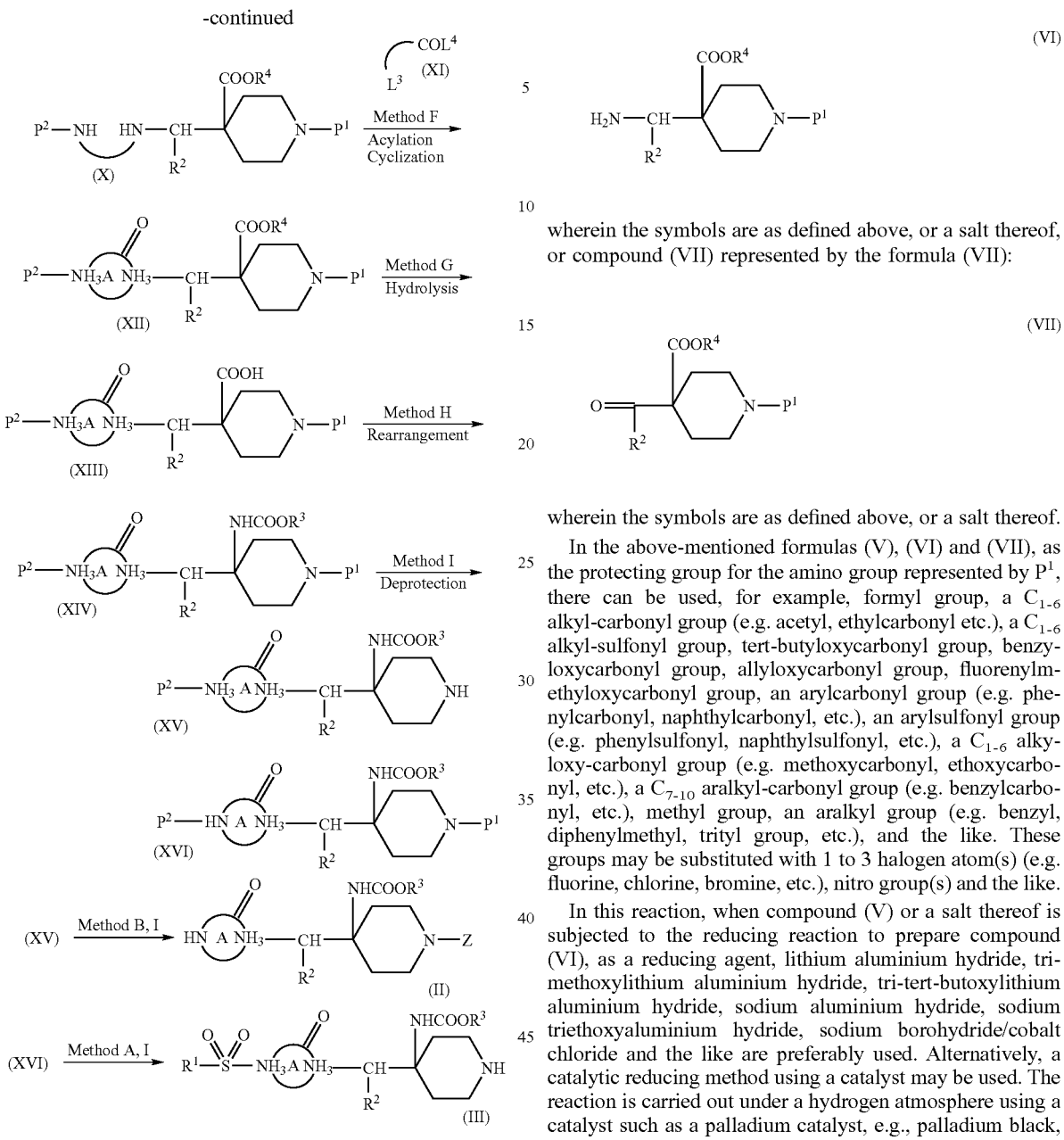

Method D

Compound (V) represented by the formula (V):

wherein $P^1$ denotes a protecting group for the amino group, and $R^4$ denotes an optionally substituted lower ($C_{1-6}$) alkyl group, or a salt thereof, is subjected to a reducing reaction to prepare compound (VI) represented by the formula (VI):

wherein the symbols are as defined above, or a salt thereof, or compound (VII) represented by the formula (VII):

wherein the symbols are as defined above, or a salt thereof.

In the above-mentioned formulas (V), (VI) and (VII), as the protecting group for the amino group represented by $P^1$, there can be used, for example, formyl group, a $C_{1-6}$ alkyl-carbonyl group (e.g. acetyl, ethylcarbonyl etc.), a $C_{1-6}$ alkyl-sulfonyl group, tert-butyloxycarbonyl group, benzyloxycarbonyl group, allyloxycarbonyl group, fluorenylmethyloxycarbonyl group, an arylcarbonyl group (e.g. phenylcarbonyl, naphthylcarbonyl, etc.), an arylsulfonyl group (e.g. phenylsulfonyl, naphthylsulfonyl, etc.), a $C_{1-6}$ alkyloxy-carbonyl group (e.g. methoxycarbonyl, ethoxycarbonyl, etc.), a $C_{7-10}$ aralkyl-carbonyl group (e.g. benzylcarbonyl, etc.), methyl group, an aralkyl group (e.g. benzyl, diphenylmethyl, trityl group, etc.), and the like. These groups may be substituted with 1 to 3 halogen atom(s) (e.g. fluorine, chlorine, bromine, etc.), nitro group(s) and the like.

In this reaction, when compound (V) or a salt thereof is subjected to the reducing reaction to prepare compound (VI), as a reducing agent, lithium aluminium hydride, trimethoxylithium aluminium hydride, tri-tert-butoxylithium aluminium hydride, sodium aluminium hydride, sodium triethoxyaluminium hydride, sodium borohydride/cobalt chloride and the like are preferably used. Alternatively, a catalytic reducing method using a catalyst may be used. The reaction is carried out under a hydrogen atmosphere using a catalyst such as a palladium catalyst, e.g., palladium black, palladium carbon, palladium-silica gel, palladium-barium sulfate and the like, a platinum catalyst, e.g., platinum oxide, platinum carbon, platinum black and the like, a rhodium catalyst, e.g., rhodium carbon, rhodium alumina and the like, a ruthenium catalyst, e.g., ruthenium oxide, ruthenium carbon and the like, Raney nickel, or the like. An amount of the catalyst to be used is about 0.0001 to about 2 moles, preferably about 0.001 to about 1 mole per 1 mole of compound (V). In addition, this catalytic reducing reaction is generally carried out under normal pressure, while it may also be carried out under pressure if necessary. Such pressure is usually about 1 to about 150 atm, preferably about 1 to about 100 atm.

This reaction is generally carried out in a solvent, and a solvent which dose not interfere with the reaction is appropriately selected. As such solvent, there can be used alcohols such as methanol, ethanol, propanol, isopropanol, butanol, tert-butanol and the like, ethers such as dioxane, tetrahydrofuran, diethyl ether, tert-butyl methyl ether, diisopropyl ether, ethylene glycol-dimethyl ether and the like, esters such as ethyl formate, ethyl acetate, n-butyl acetate and the like, halogenated hydrocarbons such as dichloromethane, chloroform, carbon tetrachloride, trichlene, 1,2-dichloroethane and the like, hydrocarbons such as n-hexane, benzene, toluene and the like, amides such as formamide, N,N-dimethylformamide, N,N-dimethylacetamide and the like, organic acids such as formic acid, acetic acid, trifluoroacetic acid and the like, dimethyl sulfoxide, sulfolane, hexamethylphosphoramide and the like. They can be used alone or as a mixed solvent thereof.

Alternatively, this reaction may be carried out in the presence of an acid if necessary and, as such acid, mineral acids such as hydrochloric acid, hydrobromic acid, sulfuric acid, phosphoric acid, perchloric acid and the like, sulfonic acids such as methanesulfonic acid, ethanesulfonic acid, benzenesulfonic acid, toluenesulfonic acid, camphorsulfonic acid and the like, and organic acids such as formic acid, acetic acid, propionic acid, trifluoroacetic acid and the like are used. When Raney nickel is used, amines such as ammonia are present in many cases. An amount of these acids to be used is about 0.01 to about 20 moles, preferably about 0.1 to about 10 moles per 1 mole of compound (V).

The reaction temperature is about $-78°$ C. to about $150°$ C., preferably about $-30°$ C. to about $100°$ C.

The reaction time varies depending on a kind of compound (V), a kind of the solvent and the reaction temperature, and is usually about 10 minutes to 72 hours, preferably about 15 minutes to about 48 hours.

In this reaction, when compound (V) or a salt thereof is subjected to the reduction to prepare carbonyl compound (VII), the iminium salt obtained by using reductant in the presence of acid is hydrolyzed with water. In this reduction, for example, a reaction using formic acid and Raney nickel may be used. An amount of the catalyst to be used is about 0.01 to about 20 moles, preferably 0.1 to about 10 mole per 1 mole of compound (V).

This reaction is generally carried out in a solvent, and a solvent which dose not interfere with the reaction is appropriately selected. As such solvent, there can be used alcohols such as methanol, ethanol, propanol, isopropanol, butanol, tert-butanol and the like, ethers such as dioxane, tetrahydrofuran, diethyl ether, tert-butyl methyl ether, diisopropyl ether, ethylene glycol-dimethyl ether and the like, esters such as ethyl formate, ethyl acetate, n-butyl acetate and the like, halogenated hydrocarbons such as dichloromethane, chloroform, carbon tetrachloride, trichlene, 1,2-dichloroethane and the like, hydrocarbons such as n-hexane, benzene, toluene and the like, amides such as formamide, N,N-dimethylformamide, N,N-dimethylacetamide and the like, organic acids such as trifluoroacetic acid and the like, dimethyl sulfoxide, sulfolane, hexamethylphosphoramide and the like. They can be used alone or as a mixed solvent thereof.

Alternatively, this reaction may be carried out in the presence of an acid if necessary and, as such acid, mineral acids such as hydrochloric acid, hydrobromic acid, sulfuric acid, phosphoric acid, perchloric acid and the like, sulfonic acids such as methanesulfonic acid, ethanesulfonic acid, benzenesulfonic acid, toluensulfonic acid, camphorsulfonic acid and the like, and organic acids such as formic acid, acetic acid, propionic acid, trifluoroacetic acid and the like are used. An amount of these acids to be used is about 0.01 to about 20 moles, preferably 0.1 to about 10 moles per 1 mole of compound (V).

The reaction temperature is about $-30°$ C. to about $150°$ C., preferably about $0°$ C. to about $120°$ C.

The reaction time varies depending on a kind of compound (V), a kind of the solvent and the reaction temperature, and is usually about 10 minutes to 72 hours, preferably about 15 minutes to about 48 hours.

Method E

Compound (X) represented by the formula (X):

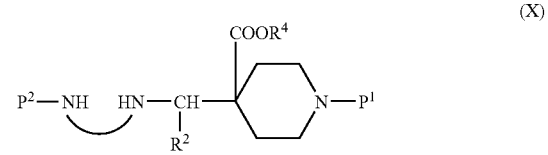

wherein the symbols are as defined above, or a salt thereof, can be prepared by subjecting compound (VI) represented by the formula (VI):

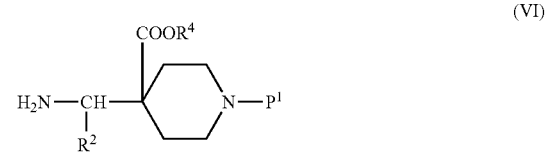

wherein the symbols are as defined above, or a salt thereof, and compound (VIII) represented by the formula (VIII):

wherein $P^2$ denotes a protecting group for the amino group, or a salt thereof, to a reductive aminating reaction, or subjecting compound (VII) represented by the formula (VII):

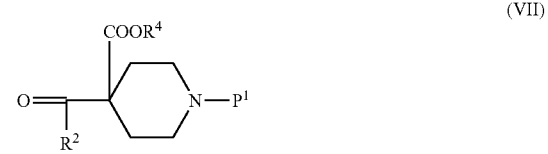

wherein the symbols are as defined above, or a salt thereof, and compound (IX) represented by formula (IX):

wherein $P^2$ denotes a protecting group for the amino group, or a salt thereof, to a reductive aminating reaction.

In the above-mentioned formulas (VIII), (IX) and (X), as the protecting group for the amino group represented by $P^2$, there can be used, for example, formyl group, a $C_{1-6}$ alkyl-carbonyl group (e.g. acetyl, ethylcarbonyl, etc.), a $C_{1-6}$ alkyl-sulfonyl group, tert-butyloxycarbonyl group, benzyloxycarbonyl group, allyloxycarbonyl group, fluorenylmethyloxycarbonyl group, an arylcarbonyl group (e.g. phenylcarbonyl, naphthylcarbonyl, etc.), an arylsulfonyl group (e.g. phenylsulfonyl, naphthylsulfonyl, etc.), a $C_{1-6}$ alkyloxy-carbonyl group (e.g. methoxycarbonyl, ethoxycarbonyl, etc.), a $C_{7-10}$ aralkyl-carbonyl group (e.g. benzylcarbonyl, etc.), methyl group, an aralkyl group (e.g. benzyl, diphenylmethyl, trityl group, etc.), and the like are used. These groups may be substituted with 1 to 3 halogen atom (e.g. fluorine, chlorine, bromine, etc.), nitro group(s) and the like.

As a reducing agent used in this reductive aminating reaction, metal hydride complex compounds such as lithium aluminium hydride, trimethoxylithium aluminium hydride, tri-tert-butoxylithium-aluminium hydride, sodium aluminium hydride, sodium triethoxyaluminium hydride, sodium borohydride, sodium trimethoxyborohydride, sodium cyanoborohydride, sodium triacetoxyborohydride, lithium borohydride, lithium cyanoborohydride, lithium triethylborohydride and the like, and triethylsilane are preferably used. Alternatively, a catalytic reducing method using a catalyst may also be used. The reaction is carried out under a hydrogen atmosphere using as a catalyst such as a palladium catalyst, e.g., palladium black, palladium carbon, palladium-silica gel, palladium-barium sulfate and the like, a platinum catalyst, e.g., platinum oxide, platinum carbon, platinum black and the like, a rhodium catalyst, e.g., rhodium carbon, rhodium alumina and the like, a ruthenium catalyst, e.g., ruthenium oxide, ruthenium carbon and the like, Raney nickel and the like. An amount of the catalyst is about 0.0001 to about 2 moles, preferably about 0.001 to about 1 mole per 1 mole of compound (VI) or compound (VII). In addition, this catalytic reducing reaction is generally carried out at normal pressure, while it may also be carried out under pressure if necessary. Such pressure is usually about 1 to about 150 atm, preferably about 1 to about 100 atm.

This reaction is generally carried out in a solvent, and a solvent which dose not interfere with the reaction is appropriately selected. As such solvent, there can be used alcohols such as methanol, ethanol, propanol, isopropanol, butanol, tert-butanol and the like, ethers such as dioxane, tetrahydrofuran, diethyl ether, tert-butyl methyl ether, diisopropyl ether, ethylene glycol-dimethyl ether and the like, esters such as ethyl formate, ethyl acetate, n-butyl acetate and the like, halogenated hydrocarbons such as dichloromethane, chloroform, carbon tetrachloride, trichlene, 1,2-dichloroethane and the like, hydrocarbons such as n-hexane, benzene, toluene and the like, amides such as formamide, N,N-dimethylformamide, N,N-dimethylacetamide and the like, organic acids such as formic acid, acetic acid, trifluoroacetic acid and the like, dimethyl sulfoxide, sulfolane, hexamethylphosphoramide and the like. They are used alone or as a mixed solvent thereof.

Alternatively, this reaction may be carried out in the presence of an acid if necessary and, as such acid, mineral acids such as hydrochloric acid, hydrobromic acid, sulfuric acid, phosphoric acid, perchloric acid and the like, sulfonic acids such as methanesulfonic acid, ethanesulfonic acid, benzenesulfonic acid, toluenesulfonic acid, camphorsulfonic acid and the like, and organic acids such as formic acid, acetic acid, propionic acid, trifluoroacetic acid and the like are used. An amount of these acids to be used is about 0.01 to about 20 moles, preferably about 0.1 to about 10 moles per 1 mole of compound (VI) or compound (VII).

The reaction temperature is about −30° C. to about 150° C., preferably about −10° C. to about 120° C.

The reaction time varies depending on a kind of compounds (VI) to (IX), a kind of the solvent and the reaction temperature, and is usually about 10 minutes to about 72 hours, preferably about 15 minutes to about 48 hours.

Method F

Compound (XII) of the formula (XII):

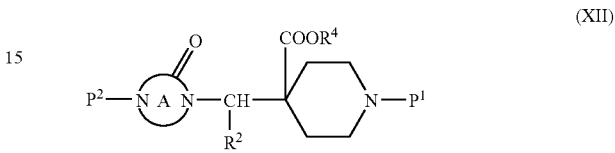

wherein the symbols are as defined above, or a salt thereof can be prepared by subjecting compound (X) represented by the formula (X):

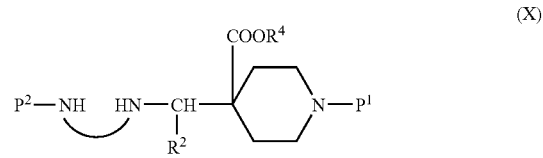

wherein the symbols are as defined above, or a salt thereof, and compound (XI) represented by the formula (XI):

wherein $L^3$ and $L^4$ denote a leaving group, or a salt thereof, to amidating reaction, followed by subjecting to cyclizing reaction.

In the above formula (XI), the leaving group represented by $L^3$ denotes, for example, a halogen atom, a group represented by the formula $R^8—SO_2—O—$ (wherein $R^8$ denotes a lower alkyl group optionally substituted with a halogen atom or a phenyl group optionally having a substituent (e.g. the same group as a lower alkyl group optionally substituted with a halogen atom or a phenyl group optionally having a substituent represented by $R^7$)), or the like. In addition, a part represented by $COL^4$ in compound (XI) represents a free acid or a salt thereof (inorganic salt, organic salt etc.) or a reactive derivative thereof (e.g. acid halide, ester, acid azide, acid anhydride, mixed acid anhydride, active amide, active ester, active thioester etc.).

Examples of a salt of compound (X) include acid addition salts with the above-mentioned acids which form an acid addition salt with compound (I).

As an inorganic salt used in compound (XI), alkali metal salts (e.g. sodium salt, potassium salt, etc.), alkaline earth metal salts (e.g. calcium salt, etc.) and the like are used and, as an organic salt, for example, trimethylamine salt, triethyamine salt, tert-butyldimethylamine salt, dibenzylmethylamine salt, benzyldimethylamine salt, N,N-dimethylaniline salt, pyridine salt, quinoline salt and the like are used. In addition, examples of acid halide include acid chloride, acid bromide and the like;, examples of the ester include lower alkyl esters such as those with methyl, ethyl and the like, examples of the mixed acid anhydride include mono $C_{1-4}$ alkylcarbonic acid mixed acid anhydride (e.g. mixed acid anhydride of free acid (XI) with monomethylcarbonic acid, monoethylcarbonic acid, monoisopropylcarbonic acid, monoisobutylcarbonic acid, mono tert-butylcarbonic acid, monobenzylcarbonic acid, mono(p-nitrobenzyl)carbonic acid, monoallylcarbonic acid, etc.), $C_{1-6}$ aliphatic carbonic acid mixed acid anhydride (e.g. mixed acid anhydride of free acid (XI) with acetic acid, cyanoacetic acid, propionic acid, butyric acid, isobutyric acid, valeric acid, isovaleric acid, pivalic acid, trifluoroacetic acid, trichloroacetic acid, acetoacetic acid, etc.), $C_{7-11}$ aromatic carboxylic acid mixed acid anhydride (e.g. mixed acid anhydride of free acid (XI) with benzoic acid, p-toluic acid, p-chlorobenzoic acid, etc.), organic sulfonic acid mixed acid anhydride (mixed acid anhydride with methanesulfonic acid, ethenesulfonic acid, benzenesulfonic acid, p-toluenesulfonic acid, etc.), and the like; and examples of the active amide include an amide with a nitrogen-containing heterocyclic compound (e.g. acid amide of free acid (XI) with pyrazole, imidazole, benzotriazole or the like, and these nitrogen-containing heterocyclic compounds may be substituted with $C_{1-6}$ alkyl (e.g. methyl, ethyl, propyl, isopropyl, butyl, isobutyl, sec-butyl, tert-butyl, etc.), $C_{1-6}$ alkoxy (e.g. methoxy, ethoxy, propoxy, isopropoxy, butoxy, tert-butoxy, etc.), halogen atom (e.g. fluorine, chlorine, bromine, etc.), oxo, thioxo, $C_{1-6}$ alkylthio (e.g. methylthio, ethylthio, propylthio, butylthio, etc.) or the like), and the like.

Examples of the active ester include, in addition to an organic phosphoric acid ester (e.g. diethoxy phosphoric acid ester, diphenoxyphosphoric acid ester, etc.), p-nitrophenyl ester, 2,4-dinitrophenyl ester, cyanomethyl ester, pentachlorophenyl ester, N-hydroxysuccineimide ester, N-hydroxyphthalimide ester, 1-hydroxybenzotriazole ester, 6-chloro-1-hydroxybenzotriazole ester, 1-hydroxy-1H-2-pyridone ester and the like. Examples of the active thioester include esters with aromatic heterocyclic thiol compounds [these heterocyclic rings may be substituted with $C_{1-6}$ alkyl (e.g. methyl, ethyl, propyl, isopropyl, butyl, isobutyl, sec-butyl, tert-butyl, etc.), $C_{1-6}$ alkoxy (e.g. methoxy, ethoxy, propoxy, isopropoxy, butoxy, tert-butoxy, etc.), halogen atom (e.g. fluorine, chlorine, bromine, etc.), $C_{1-6}$ alkylthio (e.g. methylthio, ethylthio, propylthio, butylthio, etc.) or the like][e.g. 2-pyridylthiol ester, 2-benzothiazolylthiol ester], and the like.

This reaction is generally carried out in a solvent, if necessary, in the presence of a base or a condensing agent (e.g. carbodiimides (DCC, WSC, DIC, etc.), or a phosphoric acid derivative (e.g. diethyl cyanophosphate, DPPA, BOP-Cl, etc.), etc.). As such solvent and base, solvents and bases described in the above-mentioned Method A are used as such.

In this reaction, about 1 to about 5 moles, preferably about 1 to about 2 moles of a base is used per 1 mole of compound (X).

The reaction temperature is about −50° C. to about 150° C., preferably about −20° C. to about 100° C.

The reaction time varies depending on a kind of compound (X) or (XI), a kind of the solvent and base, the reaction temperature and the like, and is usually about 1 minute to about 100 hours, preferably about 15 minutes to about 48 hours.

The intramolecular cyclizing reaction to be carried out after the amidating reaction is generally carried out in a solvent in the presence of a base and, as such solvent and base, solvents and bases described in the above-mentioned Method A are used as such.

In the reaction, about 1 to about 5 moles, preferably about 1 to about 2 moles of a base is used per 1 mole of an amide compound.

The reaction temperature is about −50° C. to about 100° C., preferably about −20° C. to about 50° C.

The reaction time varies depending on a kind of the amide compound, a kind of the solvent and the base, the reaction temperature and the like, and is usually about 1 minute to about 100 hours, preferably about 15 minutes to about 48 hours.

Method G

An ester group of compound (XII) represented by the formula (XII):

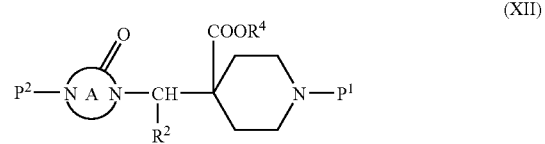

(XII)

wherein the symbols are as defined above, or a salt thereof, can be hydrolyzed to prepare compound (XIII) represented by the formula (XIII):

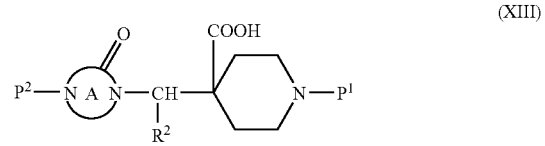

(XIII)

wherein the symbols are as defined above. or a salt thereof.

This method is an ester hydrolyzing reaction, and is carried out by appropriately using hydrolysis with an acid or an alkali, hydrogenolysis, or a method using a metal catalyst such as palladium depending on $R^4$ in compound (XII).

As the alkali used in this ester hydrolyzing reaction, alkali metal hydroxides such as lithium hydroxide, sodium hydroxide, potassium hydroxide, barium hydroxide, calcium hydroxide and the like are preferably used. In addition, as the acid used in this ester hydrolyzing reaction, for example, mineral acids such as hydrochloric acid, hydrobromic acid, sulfuric acid, phosphoric acid, nitric acid, perchloric acid and the like, sulfonic acids such as methanesulfonic acid, ethanesulfonic acid, benzenesulfonic acid, toluenesulfonic acid, camphorsulfonic acid and the like, organic acids such as formic acid, acetic acid, propionic acid, trifluoroacetic acid and the like are preferably used. Alternatively, a catalytic reducing method using a catalyst under a hydrogen atmosphere may also be used. The reaction is carried out under a hydrogen atmosphere using a catalyst such as a palladium catalyst, e.g., palladium black, palladium carbon, palladium-silica gel, palladium-barium sulfate and the like, a platinum catalyst, e.g., platinum oxide, platinum carbon, platinum black and the like, a rhodium catalyst, e.g., rhodium carbon, rhodium alumina and the like, a ruthenium catalyst, e.g., ruthenium oxide, ruthenium carbon and the like, Raney nickel or the like. An amount of the catalyst to be used is about 0.0001 to about 2 moles, preferably about 0.001 to about 1 mole per 1 mole of compound (XII). In addition, this catalytic reducing reaction is generally carried out at normal pressure, while it may also be carried out under pressure if necessary. Such pressure is usually about 1 to 150 atm, preferably about 1 to about 100 atm. In addition, in the case of an allyl ester, it can be converted into carboxylic acid or a salt thereof using a palladium catalyst.

This reaction is generally carried out in a solvent, and a solvent which dose not interfere with the reaction is appropriately selected. As such solvent, there can be used, for example, water, alcohols such as methanol, ethanol, propanol, isopropanol, butanol, tert-butanol and the like, ethers such as dioxane, tetrahydrofran, diethyl ether, tert-butyl methyl ether, diisopropyl ether, ethylene glycol-dimethyl ether and the like, halogenated hydrocarbons such as chloroform, carbon tetrachloride, trichlene, 1,2-dichloroethane and the like, hydrocarbons such as n-hexane, benzene, toluene and the like, amides such as formamide, N,N-dimethylformamide, N,N-dimethylacetamide and the like, dimethyl sulfoxide, sulfolane, hexamethylphosphoramide and the like. They are used alone or as a mixed solvent thereof.

The reaction temperature is about −30° C. to about 150° C., preferably about −10° C. to about 120° C.

The reaction time varies depending on a kind of compound (XII), a kind of the solvent and the reaction temperature, and is usually about 10 minutes to about 72 hours, preferably about 15 minutes to about 48 hours.

Method H

Compound (XIV) represented by the formula (XIV):

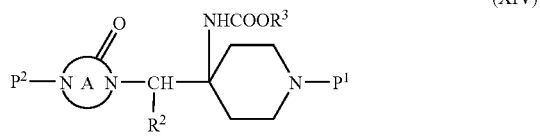

(XIV)

wherein the symbols are as defined above, or a salt thereof, can be prepared by converting a carboxylic acid compound (XIII) represented by the formula (XIII):

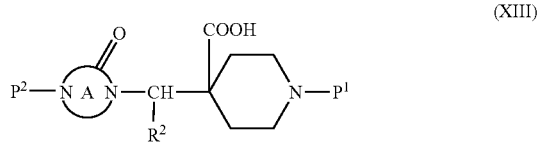

(XIII)

wherein the symbols are as defined above, or a salt thereof, into an acid azide, followed by a thermal rearrangement reaction to obtain an isocyanate, which is reacted with alcohols.

As an inorganic salt used in compound (XIII), alkali metal salts (e.g. sodium salt, potassium salt, etc.), alkaline earth metal salts (e.g. calcium salt, etc.) and the like are used. As an organic salt, for example, trimethylamine salt, triethylamine salt, tert-butyldimethylamine salt, dibenzylmethylamine salt, benzyldimethylamine salt, N,N-dimethyaniline salt, pyridine salt, quinoline salt and the like are used.

Compound (XIII) can be directly converted into an acid azide from a free acid or a salt thereof by reacting with DPPA in the presence of a base. Alternatively, compound (XIII) can be indirectly converted into an acid azide from a free acid or a salt by converting into a reactive derivative of the carboxylic acid, and reacting the derivative with an azidizing reagent such as sodium azide in the presence of a base. Examples of such reactive derivative of the carboxylic acid include acid halide (e.g. acid chloride, acid bromide, etc.), mixed acid anhydride [mono $C_{1-4}$ alkylcarbonic acid mixed acid anhydride (e.g. mixed acid anhydride of free acid (XIII) with monomethylcarbonic acid, monoethylcarbonic acid, monoisopropylcarbonic acid, monoisobutylcarbonic acid, mono tert-butylcarbonic acid, monobenzylcarbonic acid, mono (p-nitrobenzyl)carbonic acid, monoallylcarbonic acid etc.), $C_{1-6}$ aliphatic carboxylic acid mixed acid anhydride (e.g. mixed acid anhydride of free acid (XIII) with acetic acid, cyanoacetic acid, propionic acid, butyric acid, isobutyric acid, valeric acid, isovaleric acid, pivalic acid, trifluoroacetic acid, trichloroacetic acid, acetoacetic acid, etc.), $C_{7-11}$ aromatic carboxylic acid mixed acid anhydride (e.g. mixed acid anhydride of free acid (XIII) with benzoic acid, p-toluic acid, p-chlorobenzoic acid, etc.), organic sulfonic acid mixed acid anhydride (e.g. mixed acid anhydride with methanesulfonic acid, ethanesulfonic acid, benzenesulfonic acid, p-toluenesulfonic acid, etc.), etc], active amide [amide with a nitrogen-containing heterocyclic compound (e.g. acid amide of free acid (XIII) with pyrazole, imidazole, benzotriazole, etc.), these nitrogen-containing heterocyclic compounds may be substituted with $C_{1-6}$ alkyl (e.g. methyl, ethyl, propyl, isopropyl, butyl, isobutyl, sec-butyl, tert-butyl, etc.), $C_{1-6}$ alkoxy (e.g. methoxy, ethoxy, propoxy, isopropoxy, butoxy, tert-butoxy, etc.), halogen atom (e.g. fluorine, chlorine, bromine, etc.), oxo, thioxo, $C_{1-6}$ alkylthio (e.g. methylthio, ethylthio, propylthio, butylthio, etc.), etc. ), etc.], active ester [e.g. in addition to organic phosphoric acid ester (e.g. diethoxyphosphoric acid ester, diphenoxyphosphoric acid ester, etc.), p-nitrophenyl ester, 2,4-dinitrophenyl ester, cyanomethyl ester, pentachlorophenyl ester, N-hydroxysuccinimide ester, N-hydroxyphthalimide ester, 1-hydroxybenzotriazole ester, 6-chloro-1-hydroxybenzotriazole ester, 1-hydroxy-1H-2-pyridone ester, etc.], active thioester [ester with aromatic heterocyclic thiol compound [these heterocyclic rings may be substituted with $C_{1-6}$ alkyl (e.g. methyl, ethyl, propyl, isopropyl, butyl, isobutyl, sec-butyl, tert-butyl, etc.), $C_{1-6}$ alkoxy (e.g. methoxy, ethoxy, propoxy, isopropoxy, butoxy, tert-butoxy, etc.), halogen atom (e.g. fluorine, chlorine, bromine, etc.), $C_{1-6}$ alkylthio (e.g. methylthio, ethylthio, propylthio, butylthio, etc.), etc.][e.g. 2-pyridylthiol ester, 2-benzothiazolylthiol ester], etc.].

This acid azidizing reaction is generally carried out in a solvent and, if necessary, in the presence of a base or a condensing agent (e.g. carbodiimides (DCC, WSC, DIC etc.), a phosphoric acid derivative (e.g. diethyl cyanophosphate, DPPA, BOP-Cl, etc.), etc.). As such solvent and base, solvents and bases described in the above-mentioned Method A are used as such.

In the reaction, about 1 to about 5 moles, preferably about 1 to about 2 moles of an azidizing reagent is used per 1 mole of Compound (XIII).

The reaction temperature is about −50° C. to about 150° C., preferably about −20° C. to about 100° C.

The reaction time varies depending on a kind of Compound (XIII), a kind of the solvent and the base, the reaction temperature and the like, and is usually about 1 minute to about 100 hours, preferably about 15 minutes to about 48 hours.

The rearrangement reaction into the isocyanate to be carried out after the acid azidizing reaction is generally carried out in a solvent and, as such solvent, solvents and bases described in the above-mentioned Method A are used as they such. In addition, by adding a corresponding alcohol as a solvent or a reagent during this rearrangement reaction into the isocyanate, carbamate compound (XIV) can be prepared without isolating the isocyanate.

This carbamating reaction is carried out in the presence of a base in many cases, and about 1 to 5 moles, preferably about 1 to about 2 moles of a base is used per 1 mole of the isocyanate compound.

The reaction of rearranging the acid azide into the isocyanate generally requires heat, and the reaction temperature is about 50° C. to about 150° C., preferably about 70° C. to about 100° C. In addition, in the reaction from the isocyanate to the carbamate, the reaction temperature is about −10° C. to about 150° C., preferably about 0° C. to about 100° C.

These reaction times vary depending on a kind of the acid azide and the isocyanate compound, a kind of the solvent and the base, and the reaction temperature and the like, and are usually about 1 minute to about 100 hours, preferably about 15 minutes to about 48 hours.

Method I

Compound (XV) represented by the formula (XV):

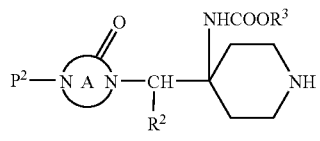

(XV)

wherein the symbols are as defined above, or a salt thereof, or compound (XVI) represented by the formula (XVI):

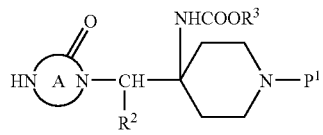

(XVI)

wherein the symbols are as defined above, or a salt thereof, can be prepared by selectively deprotecting a protecting group for the amino group in compound (XIV) represented by the formula (XIV):

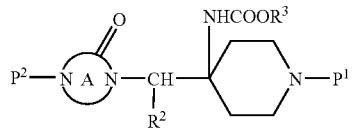

(XIV)

wherein the symbols are as defined above, or a salt thereof.

As a method for selectively removing a protecting group for the amino group, a known per se method or a similar method can be used and, for example, a method using an acid (hydrochloric acid, hydrobromic acid, trifluoroacetic acid, hydrogen fluoride, etc.), a base (amine, hydrazine, sodium hydroxide, etc.), reduction (hydrogenative degradation and catalytic reduction using a catalyst, zinc in the presence of an acid, etc.), ultraviolet-ray, palladium acetate, trimethylsilyl iodide, 1-chloroethyl chlorocarbonate/methanol and the like are used.

Compound (II) represented by the formula (II):

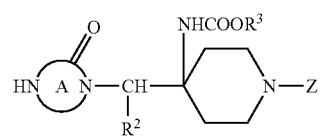

(II)

wherein the symbols are as defined above, or a salt thereof, can be prepared by reacting compound (XV) represented by the formula (XV):

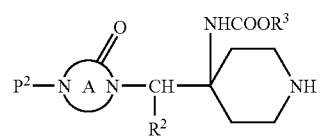

(XV)

wherein the symbols are as defined above above, or a salt thereof, with $L^1$-Z by the method shown in Method B, and subsequently deprotecting the protecting group $P^2$ by the method shown in Method I.

Further, compound(III) represented by the formula (III):

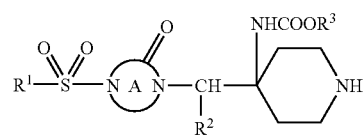

(III)

wherein the symbols are as defined above, or a salt thereof, can be prepared by reacting compound (XVI) represented by the formula (XVI):

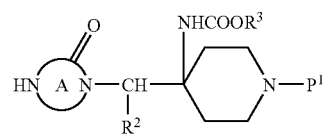

(XVI)

wherein the symbols are as defined above, or a salt thereof, with $R^1SO_2$-Q by the method shown in Method A, and subsequently deprotecting the protecting group $P^1$ by the method shown in Method I.

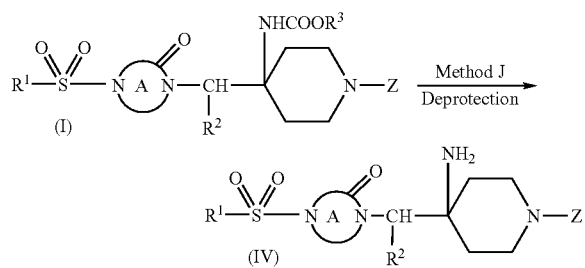

Method J
Compound (IV) represented by the formula (IV):

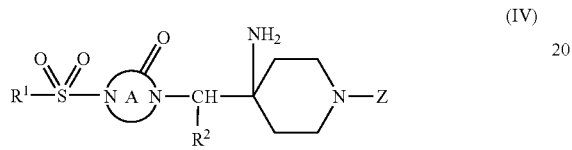

wherein the symbols are as defined above, or a salt thereof, can be prepared by deprotecting the carbamate-type protective group of compound (I) represented by the formula (I):

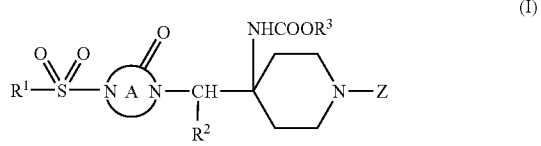

wherein the symbols are as defined above, or a salt thereof, by a known per se method and, specifically, the method of Method I corresponds thereto.

Starting compounds (V), (VIII), (IX) and (XI) used in the above-mentioned preparing Methods D to F can be prepared by a known per se method or a similar method.

When a compound is obtained in the free form by each reaction of the present invention, it may be converted into a salt according to a conventional method and, when obtained as a salt, it may be converted into a free compound or another salt according to a conventional method.

The thus-obtained compound (I) can be isolated and purified from a reaction mixture by a known per se means, for example, means such as extraction, concentration, neutralization, filtration, recrystallization, column chromatography, thin layer chromatography and the like.

A salt of compound (I) can be prepared by according to a known per se means, for example, by adding an inorganic acid or an organic acid to compound (I).

When there are stereo isomers in compound (I), these individual isomers and a mixture thereof are all included naturally in the scope of the present invention, and these isomers can be optionally prepared individually, if necessary.

In addition, compound (I) or a salt thereof may be a hydrate, and both hydrate and non-hydrate are all included in the scope of the present invention.

Since compound (I) according to the present invention or a salt thereof has a low toxicity and is safe and it inhibits an FXa and has an anticoagulative effect, it is useful in preventing and/or treating diseases, for example, cardiac infarction, cerebral thrombosis, deep vein thrombosis, pulmonary thromboembolism, thromboembolism during or after surgery, economy-class syndromes, inflammation, cancers, etc., as well as those listed below in animals especially in mammals (for example, human, monkey, cat, pig, horse, cattle, mouse, rat, guinea pig, dog, rabbit, etc.), and is preferred especially when being used in preventing and/or treating cardiogenic embolus such as atrial fibrillation, etc., cerebral infarction due to embolus derived from arteriosclerotic lesion at carotid, etc., deep vein thrombosis, pulmonary thromboembolism, and the like.

Brain:
cerebral embolus, cerebral infarction due to atrial fibrillation, acute ischemic cerebral apoplexy, acute cerebral thrombosis, cerebral vascular contraction after subarachnoidal hemorrhage, Alzheimer's disease, transient ischemic attack (TIA), mixed dementia, cerebral vascular/multiple infarction dementia, Heart:
acute coronary disease, acute cardiac infarction, cardiac infarction sequela, improvement of prognosis of cardiac infarction and/or prevention of secondary sideration of cardiac infarction, unstable angina, angina, vascular reocculusion and stenosis after coronary intervention such as stent indwelling or implementation of PTCA (percutaneous coronary angioplasty) and atherectomy, Periphery:
deep vein thrombosis, prevention of sideration and secondary sideration of deep vein thrombosis, chronic arterial occulusion, peripheral vascular disease, adult respiratory distress syndrome, chronic renal disease (e.g. diabetic nephropathy, chronic glomerulonephritis, IgA nephropathy, etc.), diabetic circulation disorder, pain, neural disorder, Others:
platelet reduction due to dialysis, platelet reduction at severe operation, atherosclerosis, cancer metastasis, systemic inflammatory response syndrome (SIRS) or disseminated intravascular coagulation syndrome (DIS), congestive chronic heart failure, rejection reaction at transplantation, organ protection or function improvement at transplantation, various organ failures generated by shock or progression of DIC (e.g. pulmonary failure, hepatic failure, renal failure, heart failure etc.), prevention of coagulation of perfusing blood at blood extracorporeal circulation.

Compound (I) of the present invention or a salt thereof can orally or parenterally be administered as it is or in combination with a pharmaceutically acceptable carrier.

A formulation containing compound (I) or a salt thereof can be given orally in a dosage form such as tablets (including sugar-coated tablets and film-coated tablets), pills, granules, powders, capsules (including soft capsules, microcapsules), syrups, emulsions and suspensions, while it can be given parenterally in a dosage form such as injection, infusion and dripping formulations as well as suppositories. Further, a sustained release preparation prepared by combining with a suitable base (e.g., a polymer of butyric acids, a polymer of glycolic acids, a copolymer of butyric acid-glycolic acid, a mixture of a polymer of butyric acids and a polymer of glycolic acids, a polyglycerol fatty acid ester, etc.) is also advantageous.

While the amount of compound (I) or a salt thereof in a formulation of the present invention may vary depending on the form of the formulation, it is usually 2 to 85% by weight, preferably 5 to 70% by weight based on the entire amount of the formulation.

A method for formulating compound (I) or a salt thereof into a dosage form described above, a known method which is generally employed in the art can be applied. Also for producing a dosage form described above, appropriate amounts of appropriate additives employed usually in the pharmaceutical field such as excipients, binders, disintegrants, lubricants, sweeteners, surfactants, suspending agents, emulsifiers and the like can be incorporated.

For example, compound (I) or a salt can be formulated into a tablet by incorporating an excipient, a binder, a disintegrant, a lubricant and the like, while it can be formulated into a pill or a granule by incorporating an excipient, a binder, a disintegrant and the like. It can be formulated also into a powder or a capsule by incorporating an excipient, into a syrup by incorporating a sweetener, into an emulsion or a suspension by incorporating a suspending agent, a surfactant, an emulsifier, and the like.

An excipient may, for example, be lactose, sugar, glucose, starch, sucrose, microcrystalline cellulose, licorice powder, mannitol, sodium hydrogen carbonate, calcium phosphate, calcium sulfate, and the like.

A binder may, for example, be 5 to 10% by weight starch glue, 10 to 20% by weight gum arabic or gelatin solution, 1 to 5% by weight tragacanth gum solution, carboxymethyl cellulose solution, sodium alginate solution glycerin, and the like.

A disintegrant may, for example, be a starch, calcium carbonate, and the like.

A lubricant may, for example, be magnesium stearate, stearic acid, calcium stearate, purified talc, and the like.

A sweetener may, for example, be glucose, fructose, inverted sugar, sorbitol, xylitol, glycerin, syrups simplex, and the like.

A surfactant may, for example, be sodium lauryl sulfate, polysorbate 80, sorbitan monofatty ester, polyoxyl stearate 40, and the like.

A suspending agent may, for example, be gum arabic, sodium alginate, sodium carboxymethyl cellulose, methyl cellulose, bentonite, and the like.

An emulsified may, for example, be gum arabic, tragacanth gum, gelatin, polysorbate 80, and the like.

Also for formulating compound (I) or a salt thereof into a dosage form described above, appropriate amounts of appropriate additives employed usually in the pharmaceutical field such as colorants, preservatives, flavors, seasonings, corrigents, stabilizers, thickening agents, and the like can be incorporated, if necessary.

A formulation according to the present invention containing compound (I) or a salt thereof is stable and has low toxicity, and can be used safely. Its daily dose may varies depending on the condition and the body weight of a patient, the type of the compound and the administration route, and is usually about 1 to 1000 mg as an active ingredient (compound (I) or a salt thereof) per day in an adult weighing about 60 kg when given orally to a patient having a thrombosis, preferably about 3 to 300 mg, more preferably about 10 to 200 mg, which can be given at once, or divided into two or 3 dosages.

When compound (I) of the present invention or a salt thereof is given parenterally, it is given usually in a liquid formulation (for example, injection formulation). In such case, a single dosage may vary depending on the target organ, the condition and the administration mode, and is usually about 0.01 mg to about 100 mg per kg body weight when given in the form of an injectable preparation, preferably about 0.01 to about 50 mg, more preferably about 0.01 to about 20 mg, which is given conveniently via intravenous injection. In addition to the intravenous injectable preparation, a subcutaneous injectable preparation, an intradermal injectable preparation, an intramuscular injectable preparation and a dripping injectable preparation may also included in the injection formulation, and an iontophoresis percutaneous formulation is included in a sustained release formulation. Any of such injection formulations can be prepared by a method known per se, i.e., by dissolving, suspending or emulsifying compound (I) of the present invention or a salt thereof in an aseptic aqueous or oily liquid. An aqueous liquid for injection may for example be a physiological saline and an isotonic solution containing glucose or other auxiliary agents (for example, D-sorbitol, D-mannitol, sodium chloride and the like), which may be used in combination with a suitable solubilizing aid such as an alcohol (for example, ethanol), a polyalcohol (for example, propylene glycol, polyethylene glycol), a nonionic surfactant (for example, polysorbate 80, HCO-50), and the like. An oily liquid may, for example, be a sesame oil, a soybean oil, etc., which may be used in combination with a solubilizing aid such as benzyl benzoate, benzyl alcohol, etc. Those which may also be incorporated are a buffering agent (for example, phosphate buffer and sodium acetate buffer), an analgesic (for example, benzalkonium chloride, procaine hydrochloride, etc.), a stabilizer (for example, human serum albumin, polyethylene glycol, etc.), a preservative (for example, benzyl alcohol, phenol, etc.), and the like. The injection formulation thus prepared is contained usually in an ampule.

The formulation of the present invention may appropriately be used in combination with a thrombolytic agent (for example, TPA, urokinase. etc.), an Alzheimer treating agent (for example, Avan, Calan, etc.), a cholesterol treating agent (for example, HMG-CoA reductase inhibitor such as simvastatin, pravastatin, etc.), a TG reducing agent (for example, clofibrate, etc.), an AII antagonist (for example, candesartan, cilexetil, losartan, etc.), an antiplatelet agent (for example, clopidogrel, abciximab, aspirin, etc.), a Ca antagonist (for example, calslot, amlodipine, etc.), an ACE inhibitor (for example, enalapril, captopril, etc.), a β blocker (for example, metoprolol, carvedilol, etc.), an antiarrhythmic agent (for example, procaine amide, etc.), and the like, or these medicinal components can appropriately formulated in a preparation.

The present invention is further detailed in the following Reference Examples, Examples, Formulation Examples and Experiments, which serve only as examples and are not intended to restrict the present invention and can be modified without departing the scope of the present invention.

Elution of a column chromatography in Reference Examples and Examples was conducted with observing by TLC (thin layer chromatography). In the observation of TLC, a TLC plate employed was a 60F254 manufactured by Merck, and the plate was developed with a solvent which was employed as an eluent in a column chromatography, while an UV detector was used for detection. Silica gel employed was kieselgel 60 (70 to 230 mesh) manufactured by Merck. NMR spectra were recorded on a Gemini 200 spectrometer using tetramethylsilane as an internal or external standard and the chemical shift data were represented in δ values (ppm). IR spectra were determined on a Shimadzu FTZR-8200 spectrometer. The figure in a bracket indicated in conjunction with a mixed solvent is a volume ratio of the constituent solvents. The percent indicated in conjunction with a solution is the amount in gram contained in 100 ml of the solution. The following abbreviations are employed in Reference Examples and Examples.

s: singlet
d: doublet
t: triplet
q: quartet
quint: quintet
ABq: AB type quartet
dd: double doublet
m: multiplet
br: broad
brs: broad singlet
J: coupling constant
WSC: water-soluble carbodiimide
THF: tetrahydrofuran
DMF: dimethylformamide
DMSO: dimethylsulfoxide
Fmoc: 9-fluorenylmethoxycarbonyl
HOBt: 1-hydroxybenzotriazole

REFERENCE EXAMPLE 1

4-Benzyloxycarbonyl-1-[1,4-bis(tert-butoxycarbonyl)-4-piperidylmethyl]-2-piperazinone An aqueous solution (400 ml) of sodium carbonate (31.8 g) and carbobenzoxy chloride (51.2 g) were added to a solution of 2,2-diethoxyethylamine (42.0 g) in ethyl acetate (300 ml) under ice-cooling, and the mixture was stirred for 6 hours. After separating the mixture into layers, the organic layer was washed successively with 0.5N hydrochloric acid, an aqueous sodium bicarbonate solution and an aqueous saturated sodium chloride solution, dried and concentrated to give pale orange oily benzyl 2,2-diethoxyethylcarbamate (78.6 g).
$^1$H-NMR (CDCl$_3$) δ: 1.20 (6H, t, J=7.0 Hz), 3.33 (2H, t, J=5.7 Hz), 3.40–3.80 (4H, m), 4.50 (1H, t, J=5.3 Hz), 4.90 (1H, br), 5.11 (2H, s), 7.30–7.45 (5H, m).

To a solution of benzyl 2,2-diethoxyethylcarbamate (45.4 g) in acetone (260 ml) was added 1N Hydrochloric acid (130 ml), and the mixture was stirred at 60° C. for 40 minutes. An aqueous saturated sodium bicarbonate solution was added to the reaction solution, followed by extraction with ethyl acetate. The organic layer was washed with an aqueous saturated sodium chloride solution, dried and concentrated. The resulting oil (37.7 g) was dissolved in THF (600 ml), tert-butyl 1-(tert-butoxycarbonyl)-4-aminomethylisonipecotinate (37.7 g), acetic acid (6.87 ml) and sodium triacetoxyborohydride (36.0 g) were added thereto, and the mixture was stirred at room temperature for 3 days. The reaction mixture was concentrated under reduced pressure, and the residue was purified by silica gel column chromatography (hexane:ethyl acetate=2:1→0:1) to obtain pale yellow oily tert-butyl 1-(tert-butoxycarbonyl)-4-[N-[2-[N-(benzyloxycarbonyl)amino]ethyl]aminomethyl]-isonipecotinate.
$^1$H-NMR (CDCl$_3$) δ: 1.20–1.60 (2H, m), 1.44 (9H, s), 1.45 (9H, s), 1.95–2.10 (2H, m), 2.64 (2H, s), 2.71 (2H, t, J=5.7 Hz), 2.85–3.05 (2H, m), 3.24 (2H, q, J=4.3 Hz), 3.75–3.95 (2H, m), 5.09 (2H, s), 5.05–5.25 (1H, m), 7.30–7.40 (5H, m).

tert-Butyl 1-(tert-butoxycarbonyl)-4-[N-[2-[N-(benzyloxycarbonyl)amino]ethyl]aminomethyl]isonipecotinate (40.4 g) was dissolved in ethyl acetate (300 ml) and THF (100 ml), triethylamine (17.2 ml) was added, and then a solution of chloroacetyl chloride (7.85 ml) in ethyl acetate (50 ml) was added dropwise thereto at 0° C. After stirring at 0° C. for 30 minutes, water was added thereto, and the mixture was extracted with ethyl acetate. The organic layer was washed with 5% aqueous citric acid, an aqueous saturated sodium bicarbonate solution and an aqueous saturated sodium chloride solution, dried and concentrated. The resulting residue (46.6 g) was dissolved in DMF (450 ml), sodium hydride (3.60 g) was added under ice-cooling, and the mixture was stirred at room temperature for 3 days. After the reaction solution was concentrated under reduced pressure, ethyl acetate was added thereto, the solution was washed with water and an aqueous saturated sodium chloride solution, dried, and concentrated. The residue was subjected to silica gel column chromatography (hexane: ethyl acetate=2:1→0:1) to obtain the title compound (35.3 g) as an orange syrup.
$^1$H-NMR (CDCl$_3$) δ: 1.30–1.60 (2H, m), 1.44 (9H, s), 1.47 (9H, s), 1.90–2.10 (2H, m), 2.70–3.00 (2H, m), 3.20–4.10 (8H, m), 4.15 (2H, s), 5.15 (2H, s), 7.30–7.40 (5H, m).

REFERENCE EXAMPLE 2

1-(tert-Butoxycarbonyl)-4-[4-(6-chloro-2-naphthalenesulfonyl)-2-oxo-1-piperazinylmethyl]isonipecotinic acid

REFERENCE EXAMPLE 2-1

1-[1,4-Bis(tert-butoxycarbonyl)-4-piperidylmethyl]-4-(6-chloronaphthalene-2-sulfonyl)-2-piperazinone 4-Benzyloxycarbonyl-1-[1,4-bis(tert-butoxycarbonyl)-4-piperidylmethyl]-2-piperazinone (35 g) was dissolved in ethanol (400 ml), 10% palladium carbon (5.0 g) was added, and the mixture was vigorously stirred for 1 hour under a hydrogen stream. After the catalyst was removed, the solvent was distilled off under reduced pressure. The resulting residue was dissolved in ethyl acetate (300 ml), an aqueous solution (200 ml) of sodium carbonate (10.5 g), and a solution of 6-chloronaphthalene-2-sulfonyl chloride (18.9 g) in ethyl acetate 100 ml) were added at 0° C. After stirring at 0° C. for 2 hours, the organic layer was separated, washed with an aqueous saturated sodium chloride solution, dried, and concentrated. The residue was subjected to silica gel column chromatography (ethyl acetate:methanol=1:1) to obtain the amorphous title compound (33.5 g).
$^1$H-NMR (CDCl$_3$) δ: 1.25–1.50 (2H, m), 1.42 (9H, s), 1.44 (9H, s), 1.80–2.00 (2H, m), 2.68–2.90 (2H, m), 3.26–3.70 (6H, m), 3.77 (2H, s), 3.70–4.00 (2H, m), 7.61 (1H, dd, J=8.9, 1.9 Hz), 7.78 (1H, dd, J=8.6, 1.8 Hz), 7.91–7.98 (3H, m), 8.34 (1H, d, J=1.4 Hz).

REFERENCE EXAMPLE 2-2

1-(tert-Butoxycarbonyl)-4-[4-(6-chloro-2-naphthalenesulfonyl)-2-oxo-1-piperazinylmethyl]isonipecotinic acid Trifluoroacetic acid (100 ml) was added to a solution of 1-[1,4-bis(tert-butoxycarbonyl)-4-piperidylmethyl]-4-(6-chloronaphthalene-2-sulfonyl)-2-piperazinone (36.5 g) in toluene (100 ml), and the mixture was stirred at room temperature for 3 hours. The reaction mixture was concentrated, THF (200 ml), 1N sodium hydroxide (500 ml), and di-tert-butyl dicarbonate (17.6 g) were added to the resulting residue, and the mixture was stirred at room temperature for 4 hours. Acetic acid (30 ml) was added to the reaction mixture to adjust to weak acidic, and the mixture was extracted with ethyl acetate. The organic layer was washed with an aqueous saturated sodium chloride solution, dried, and concentrated. The precipitated crystals were washed with ether to obtain the title compound (23.7 g) as colorless crystals.

$^1$H-NMR (CDCl$_3$) δ: 1.20–1.50 (2H, m), 1.44 (9H, s), 1.90–2.08 (2H, m), 2.65–2.95 (2H, m), 3.30–3.70 (6H, m), 3.75–4.10 (2H, m), 3.82 (2H, s), 7.58 (1H, dd, J=8.8, 2.0 Hz), 7.80 (1H, dd, J=8.6, 1.6 Hz), 7.86–8.00 (3H, m), 8.39 (1H, s).

REFERENCE EXAMPLE 3

1-(tert-Butoxycarbonyl)-4-[2-oxo-4-(4-vinylbenzenesulfonyl)-1-piperazinylmethyl]isonicopetinic acid According to the same manner as that of Reference Example 2 except that 4-vinylbenzenesulfonyl chloride was used in place of 6-chloronaphthalene-2-sulfonyl chloride, the colorless amorphous title compound was obtained.

$^1$H-NMR (CDCl$_3$) δ: 1.20–1.50 (2H, m), 1.44 (9H, s), 1.95–2.10 (2H, m), 2.70–3.00 (2H, m), 3.20–3.80 (6H, m), 3.76 (2H, s), 3.80–4.10 (2H, m), 5.47 (1H, d, J=10.8 Hz), 5.91 (1H, d, J=17.6 Hz), 6.76 (1H, dd, J=17.6, 10.8 Hz), 7.58 (2H, d, J=8.5 Hz), 7.76 (2H, d, J=8.5 Hz).

REFERENCE EXAMPLE 4

1-(tert-Butoxycarbonyl)-4-[4-(7-chloro-2H-benzopyran-3-sulfonyl)-2-oxo-1-piperazinylmethyl]isonipecotinic acid

REFERENCE EXAMPLE 4-1

1-[1,4-Bis(tert-butoxycarbonyl)-4-piperidylmethyl]-4-(7-chloro-2H-benzopyran-3-sulfonyl)-2-piperazinone 4-Benzyloxycarbonyl-1-[1,4-bis(tert-butoxycarbonyl)-4-piperidylmethyl]-2-piperazinone (21.7 g) was dissolved in ethanol (200 ml), 10% palladium carbon (3.5 g) was added, and the mixture was vigorously stirred for 1 hour under a hydrogen stream. After the catalyst was removed, the solvent was distilled off under reduced pressure. The resulting residue (16.1 g) was dissolved in dichloromethane (320 ml). After N-ethyldiisopropylamine (8.36 ml) was added, a solution of 7-chloro-4H-4-oxobenzopyran-3-sulfonyl chloride (12.3 g) in dichloromethane (160 ml) was added in portions under ice-cooling, and the mixture was stirred at 0° C. for 2 hours. The reaction mixture was washed with an aqueous sodium bicarbonate solution and an aqueous saturated sodium chloride solution, dried and concentrated to obtain the residue, which was purified by silica gel column chromatography (ethyl acetate). Sodium borohydrate (1.41 g) was added to a solution of the resulting crystalline powder (16.0 g) in methanol/THF (1:1, 400 ml) under ice-cooling, and the mixture was stirred at 0° C. for 1 hour. Acetic acid (2.13 ml) was added to the reaction mixture, and the mixture was concentrated. To the residue was added water, the mixture was extracted with ethyl acetate-THF, washed successively with an aqueous saturated sodium bicarbonate solution and an aqueous saturated sodium chloride solution, and dried. The solvent was distilled off to obtain the residue, which was dissolved in THF (180 ml), triethylamine (10.4 ml), followed by a solution of methanesulfonyl chloride (2.88 ml) in THF (20 ml) were added at 0° C., and the mixture was stirred at room temperature overnight. During that process, triethylamine (6.9 ml) and methanesulfonyl chloride (0.96 ml) were further added. Ethyl acetate was added to the reaction solution, and the mixture was washed successively with water, 10% aqueous citric acid, an aqueous saturated sodium bicarbonate solution and an aqueous saturated sodium chloride solution, dried, and concentrated. The resulting residue was purified by silica gel column chromatography (hexane:ethyl acetate=2:1→1:2) to obtain the colorless amorphous title compound (14.2 g).

$^1$H-NMR (CDCl$_3$) δ: 1.30–1.60 (2H, m), 1.44 (9H, s), 1.47 (9H, s), 1.90–2.10 (2H, m), 2.70–3.00 (2H, m), 3.30–3.80 (6H, m), 3.80–4.05 (2H, m), 3.89 (2H, s), 4.88 (2H, d, J=1.2 Hz), 6.92 (1H, d, J=1.9 Hz), 6.99 (1H, dd, J=8.1, 1.9 Hz), 7.13 (1H, d, J=8.1 Hz), 7.27 (1H, s).

REFERENCE EXAMPLE 4-2

1-(tert-Butoxycarbonyl)-4-[4-(7-chloro-2H-benzopyran-3-sulfonyl)-2-oxo-1-piperazinylmethyl]isonipecotinic acid According to the same manner as that of Reference Example 2-2 except that 1-[1,4-bis(tert-butoxycarbonyl)-4-piperidylmethyl]-4-(7-chloro-2H-benzopyran-3-sulfonyl)-2-piperazinone was used, the colorless crystalline title compound was obtained.

$^1$H-NMR (CDCl$_3$) δ: 1.20–1.50 (2H, m), 1.45 (9H, s), 2.00–2.20 (2H, m), 2.70–3.00 (2H, m), 3.40–3.75 (2H, m), 3.52 (4H, s), 3.85–4.10 (2H, m), 3.93 (2H, s), 4.88 (2H, s), 6.91 (1H, d, J=1.6 Hz), 6.98 (1H, dd, J=8.1, 1.6 Hz), 7.15 (1H, d, J=8.1 Hz), 7.30 (1H, s).

REFERENCE EXAMPLE 5

1-[4-Amino-1-(4-pyridyl)-4-piperidylmethyl]-4-(6-chloronaphthalene-2-sulfonyl)-2-piperazinone dihydrochloride

REFERENCE EXAMPLE 5-1

1-[4-Benzyloxycarbonylamino-1-(tert-butoxycarbonyl)-4-piperidylmethyl]-4-(6-chloronaphthalene-2-sulfonyl)-2-piperazinone Triethylamine (1.67 ml) and diphenylphosphoryl azide (2.59 ml) were added to a solution of 1-(tert-butoxycarbonyl)-4-[4-(6-chloro-2-naphthalenesulfonyl)-2-oxo-1-piperazinylmethyl]isonipecotinic acid (5.66 g) in toluene (100 ml), and the mixture was stirred at room temperature for 1 hour, and at 100° C. for 30 minutes. Benzyl alcohol (1.57 ml) was added to the reaction mixture, and the mixture was further stirred at 100° C. overnight. The reaction mixture was concentrated, and the resulting residue was purified by silica gel column chromatography (hexane:ethyl acetate=1:1) to obtain the amorphous title compound (7.42 g).

$^1$H-NMR (CDCl$_3$) δ: 1.42 (9H, s), 1.35–2.00 (4H, m), 2.77–2.95 (2H, m), 3.05–3.35 (4H, m), 3.55–3.90 (6H, m), 4.47 (1H, s), 5.02 (2H, s), 7.30–7.45 (5H, m), 7.60 (1H, dd, J=8.8, 1.8 Hz), 7.75 (1H, dd, J=8.8, 1.8 Hz), 7.88–7.98 (3H, m), 8.32 (1H, s).

REFERENCE EXAMPLE 5-2

1-[4-Benzyloxycarbonylamino-1-(4-pyridyl)-4-piperidylmethyl]-4-(6-chloronaphthalene-2-sulfonyl)-2-piperazinone A 4N hydrochloric acid solution in ethyl acetate (50 ml) and ethanol (10 ml) was added to 1-[4-benzyloxycarbonylamino-1-(tert-butoxycarbonyl)-4-piperidylmethyl]-4-(6-chloronaphthalene-2-sulfonyl)-2-piperazinone (7.42 g), and the mixture was stirred at room temperature for 1 hour. The reaction mixture was concentrated under reduced pressure, 4-chloropyridine hydrochloride (1.80 g), triethylamine(6.97 ml) and ethanol (100 ml) were added to the residue, and the mixture was heated at 150° C. for 5 hours in a sealed tube. After cooling, the reaction mixture was diluted with ethyl acetate, and washed with water. The ethyl acetate layer was dried with magnesium sulfate, and concentrated under reduced pressure. The residue was purified by basic silica gel chromatography (ethyl acetate-ethyl acetate/methanol=8/1) to obtain the title compound (3.58 g, 55%) as powders.
$^1$H-NMR (CDCl$_3$) δ: 1.55–1.80 (2H, m), 1.80–2.05 (2H, m), 2.85–3.05 (2H, m), 3.15–3.33 (4H, m), 3.45–3.62 (2H, m), 3.66 (2H, s), 3.77 (2H, s), 4.60 (1H, s), 5.04 (2H, s), 6.60 (2H, d, J=6.3 Hz), 7.30–7.45 (5H, m), 7.61 (1H, dd, J=8.9, 1.9 Hz), 7.76 (1H, dd, J=8.7, 1.7 Hz), 7.88–7.98 (3H, m), 8.25 (2H, d, J=6.3 Hz), 8.34 (1H, s).

REFERENCE EXAMPLE 5-3

1-[4-Amino-1-(4-pyridyl)-4-piperidylmethyl]-4-(6-chloronaphthalene-2-sulfonyl)-2-piperazinone dihydrochloride Iodotrimethylsilane (2.51 ml) was added to a solution of 1-[4-benzyloxycarbonylamino-1-(4-pyridyl)-4-piperidylmethyl]-4-(6-chloronaphthalene-2-sulfonyl)-2-piperazinone (4.58 g) in dichloromethane (50 ml), and the mixture was stirred at room temperature for 4 hours. Methanol (10 ml) and 4N hydrochloric acid solution in ethyl acetate (8 ml) were added thereto. Methanol was added to obtain a solution, followed by concentration under reduced pressure. Dilute hydrochloric acid was added to the residue, and the mixture was washed with ether. The aqueous layer was made basic with 6N sodium hydroxide, followed by extraction with ethyl acetate. The organic layer was washed successively with an aqueous sodium bicarbonate solution and an aqueous saturated sodium chloride solution, dried, and concentrated. Dilute hydrochloric solution was added to the residue, which was purified by CHP20 column chromatography (water:acetonitrile:1N hydrochloric acid=100:0:1→80:20:1) to obtain the colorless amorphous title compound (3.66 g).
$^1$H-NMR (DMSO-d$_6$) δ: 1.86 (4H, br), 3.38 (2H, m), 3.46–3.64 (4H, m), 3.68 (2H, s), 3.70–4.00 (4H, m), 7.19 (2H, d, J=7.4 Hz), 7.76 (1H, dd, J=8.8, 2.2 Hz), 7.92 (1H, dd, J=8.6, 1.8 Hz), 8.18–8.55 (8H, m), 8.63 (1H, s).

REFERENCE EXAMPLE 6

4-[[4-(Benzyloxycarbonyl)-2-oxo-1-piperazinyl] methyl]-1-(tert-butoxycarbonyl)-4-piperidinecarboxylic acid Trifluoroacetic acid (100 ml) was added to a solution of 4-benzyloxycarbonyl-1-[1,4-bis(tert-butoxycarbonyl)-4-piperidylmethyl]-2-piperazinone (38.8 g) obtained in Reference Example 1 in toluene (100 ml), the mixture was stirred at room temperature for 1 hour, and concentrated under reduced pressure. Then, di-tert-butyl dicarbonate (17.6 ml) was added to a mixture of the residue, sodium carbonate (38.7 g), water (300 ml) and ethyl acetate (300 ml) at room temperature while stirring, and the mixture was stirred at room temperature for 1 hour. The reaction mixture was separated into layers, the aqueous layer was adjusted to pH 3 with 1N hydrochloric acid, and extracted with ethyl acetate. The ethyl acetate layer was dried with magnesium sulfate, and concentrated under reduced pressure, and the residue was purified by silica gel chromatography (ethyl acetate:methanol=10/1) to obtain the title compound (29 g) as yellow powders.
$^1$H-NMR (CDCl$_3$+D$_2$O): δ 1.30–1.58 (2H, m), 1.44 (9H, s), 2.00–2.20 (2H, m), 2.74–2.98 (2H, m), 3.36–3.74 (6H, m), (5H, m 0.86–4.06 (2H, m), 4.16 (2H, s), 5.15 (2H, s), 7.30–7.40 (5H, m).

REFERENCE EXAMPLE 7

Benzyl 4-[[1-(tert-butoxycarbonyl)-4-[(ethoxycarbonyl)amino]-4-piperidinyl]methyl]-3-oxo-1-piperazinecarboxylate Diphenylphosphoryl azide (15.8 ml) was added to a mixture of 4-[[4-(benzyloxycarbonyl)-2-oxo-1-piperazinyl] methyl]-1-(tert-butoxycarbonyl)-4-piperidinecarboxylic acid (29 g) obtained in Reference Example 6, triethylamine (10.2 ml) and toluene (290 ml) at 0° C. under stirring, and the mixture was stirred at room temperature for 1 hour, and at 100° C. for 2 hours. Ethanol (290 ml) was added, and the mixture was heated under reflux for 12 hours, and concentrated under reduced pressure. The residue was purified by silica gel chromatography (hexane/ethyl acetate=1/3-ethyl acetate/methanol=10/1) to obtain the title compound (26 g, 82%) as pale yellow powders.
$^1$H-NMR (CDCl$_3$): δ 1.23 (3H, t, J=7.0 Hz), 1.44 (9H, s), 1.50–1.73 (2H, m), 1.82–2.05 (2H, m), 2.90–3.10 (2H, m), 3.40–3.53 (2H, m), 3.60–3.92 (6H, m), 4.08 (2H, q, J=7.0 Hz), 4.16 (2H, s), 4.59 (1H, s), 5.16 (2H, s), 7.30–7.42 (5H, m).

REFERENCE EXAMPLE 8

Benzyl 4-[[4-[(ethoxycarbonyl)amino]-4-piperidinyl]methyl]-3-oxo-1-piperazinecarboxylate trifluoroacetate Trifluoroacetic acid (78 ml) was added to a solution of benzyl 4-[[1-(tert-butoxycarbonyl)-4-[(ethoxycarbonyl) amino]-4-piperidinyl]methyl]-3-oxo-1-piperazinecarboxylate (26 g) obtained in Reference Example 7 in toluene (78 ml) at room temperature while stirring, and the mixture was stirred at room temperature for 1 hour. The reaction mixture was concentrated under reduced pressure, and the residue was crystallized from ethyl acetate/diethyl ether=5/1) to obtain the title compound (16 g, 60%) as colorless crystals.
$^1$H-NMR (DMSO-d$_6$+D$_2$O): δ 1.17 (3H, t, J=7.0 Hz), 1.52–1.78 (2H, m), 2.04–2.24 (2H, m), 2.76–2.98 (2H, m), 3.04–3.24 (2H, m), 3.32–3.48 (2H, m), 3.50–3.68 (4H, m), 3.90–4.10 (4H, m), 5.11 (2H, s), 7.30–7.50 (5H, m).

REFERENCE EXAMPLE 9

Benzyl 4-[[4-[(ethoxycarbonyl)amino]-1-(4-pyridinyl)-4-piperidinyl]methyl]-3-oxo-1-piperidinecarboxylate A mixture of benzyl 4-[[4-[(ethoxycarbonyl)amino]-4-piperidinyl]methyl]-3-oxo-1-piperazinecarboxylate trifluoroacetate (15.9 g) obtained in Reference Example 8, 4-chloropyridine hydrochloride (5.39 g), triethylamine (41.7 ml) and ethanol (159 ml) was heated at 150° C. for 5 hours in a sealed tube. After cooling, the reaction mixture was diluted with ethyl acetate, and washed with water. The ethyl acetate layer was dried with magnesium sulfate, and concentrated under reduced pressure. The residue was purified by basic silica gel chromatography (ethyl acetate-ethyl acetate/methanol=8/1) to obtain the title compound (9.3 g, 63%) as yellow powders.

IR (KBr) 2930, 1713, 1599, 1260, 1238 $cm^{-1}$. $^1$H-NMR (CDCl$_3$): δ 1.24 (3H, t, J=7.2 Hz), 1.70–1.90 (2H, m), 2.02–2.18 (2H, m), 2.98–3.16 (2H, m), 3.42–3.74 (6H, m), 3.79 (2H, s), 4.09 (2H, q, J=7.2 Hz), 4.17 (2H, s), 4.67 (1H, s), 5.16 (2H, s), 6.65 (2H, d, J=6.4 Hz), 7.30–7.55 (5H, m), 8.26 (2H, d, J=6.4 Hz).

REFERENCE EXAMPLE 10

4-Benzyloxycarbonyl-1-{[4-ethoxycarbonylamino-1-(2-methyl-4-pyridyl)-4-piperidinyl]methyl}-2-piperazinone 4-Chloro-2-methylpyridine hydrochloride (941 mg), triethylamine (1.93 g) and ethanol (50 ml) were added to 4-benzyloxycarbonyl-1-[(4-ethoxycarbonylamino-4-piperidinyl)methyl]-2-piperazinone (2.0 g), and the mixture was reacted at 150° C. for 10 hours in a sealed tube. The reaction mixture was concentrated, a 10% aqueous sodium carbonate solution was added to the residue, and the mixture was extracted with dichloromethane, dried, and concentrated. The resulting residue was purified by column chromatography (dichloromethane:10% aqueous ammonia-containing methanol=20:1) to obtain the colorless amorphous title compound (1.31 g).

$^1$H-NMR (CDCl$_3$) δ: 1.23 (3H, t, J=7.0 Hz), 1.79 (2H, m), 2.07 (2H, m), 2.44 (3H, s), 3.06 (2H, m), 3.40–3.75 (6H, m), 3.78 (2H, s), 4.08 (2H, q, J=7.0 Hz), 4.17 (2H, s), 4.59 (1H, s), 5.16 (2H, s), 6.45–6.55 (2H, m), 7.37 (5H, s), 8.16 (1H, d, J=6.0 Hz).

REFERENCE EXAMPLE 11

1-{[4-Ethoxycarbonylamino-1-(2-methyl-4-pyridyl)-4-piperidinyl]methyl}-2-piperazinone hydrochloride A 4N hydrochloric acid solution in ethyl acetate (0.7 ml) and 10% palladium carbon (500 mg) were added to a solution of 4-benzyloxycarbonyl-1-{[4-ethoxycarbonylamino-1-(2-methyl-4-pyridyl)-4-piperidinyl]methyl}-2-piperazinone (1.3 g) in ethanol (50 ml), and the mixture was stirred at room temperature for 15 hours under a nitrogen atmosphere. After the catalyst was removed, the solvent was distilled off to obtain the colorless amorphous title compound (1.15 g).

$^1$H-NMR (CD$_3$OD) δ: 1.25 (3H, t, J=7.0 Hz), 1.73 (2H, m), 2.33 (2H, m), 2.51 (3H, s), 3.25–3.45 (4H, m), 3.67 (2H, m), 3.73 (2H, s), 3.77 (2H, s), 3.95–4.15 (4H, m), 7.00–7.10 (2H, m), 7.98 (1H, d, J=8.0 Hz).

REFERENCE EXAMPLE 12

1-{[1-(Tert-butoxycarbonyl)-4-ethoxycarbonylamino-4-piperidinyl]methyl}-2-piperazinone 10% Palladium carbon (600 mg) was added to a solution of 4-benzyloxycarbonyl-1-{[1-(tert-butoxycarbonyl)-4-ethoxycarbonylamino-4-piperidinyl]methyl}-2-piperazinone (1.79 g) in ethanol (50 ml), and the mixture was stirred at room temperature for 15 hours under a nitrogen atmosphere. After the catalyst was filtered, the solvent was distilled off to obtain the colorless amorphous title compound (1.46 g).

$^1$H-NMR (CDCl$_3$) δ: 1.24 (3H, t, J=7.0 Hz), 1.44 (9H, s), 1.54 (2H, m), 2.15 (2H, m), 3.00 (2H, m), 3.40–4.20 (12H, m), 5.60 (1H, brs), 9.93 (1H, s).

REFERENCE EXAMPLE 13

1-{[1-(Tert-butoxycarbonyl-4-ethoxycarbonylamino-4-piperidinyl]methyl}-4-(4-vinylbenzenesulfonyl)-2-piperazinone Triethylamine (735 mg) was added to a solution of 1-{[1-(tert-butoxycarbonyl)-4-ethoxycarbonylamino-4-piperidinyl]methyl}-2-piperazinone (1.4 g) in dichloromethane (80 ml), and 4-vinylbenzenesulfonyl chloride (885 mg) was added at 0° C., and the mixture was stirred at room temperature for 1 hour. An aqueous sodium carbonate solution was added to the reaction solution, and the mixture was extracted with dichloromethane, dried, concentrated, and purified by silica gel column chromatography (hexane:ethyl acetate=1:2) to obtain the colorless amorphous title compound (1.50 g).

$^1$H-NMR (CDCl$_3$) δ: 1.23 (3H, t, J=7.0 Hz), 1.43 (9H, s), 1.56 (2H, m), 1.84 (2H, m), 2.95 (2H, m), 3.30 (2H, m), 3.51 (2H, m), 3.60–3.90 (6H, m), 4.06 (2H, q, J=7.0 Hz), 4.49 (1H, brs), 5.48 (1H, d, J=11.0Hz), 5.92 (1H, d, J=17.6 Hz), 6.77 (1H, dd, J=11.0, 17.6 Hz), 7.58 (2H, d, J=8.4 Hz), 7.75 (2H, d, J=8.4 Hz).

REFERENCE EXAMPLE 14

1-{[4-Eethoxycarbonylamino-4-piperidinyl]methyl}-4-(4-vinylbenzenesulfonyl)-2-piperazinone hydrochloride A 4N hydrochloric acid solution in ethyl acetate (20 ml) was added to 1-{[1-(tert-butoxycarbonyl)-4-ethoxycarbonylamino-4-piperidinyl]methyl}-4-(4-vinylbenzenesulfonyl)-2-piperazinone (2.0 g), and the mixture was stirred at room temperature for 30 minutes. The solvent was distilled off to obtain the colorless amorphous title compound (1.45 g).

EXAMPLE 1

4-(6-Chloronaphthalene-2-sulfonyl)-1-[4-ethoxycarbonylamino-1-(4-pyridyl)-4-piperidylmethyl]-2-piperazinone

EXAMPLE 1-1

1-[1-(Tert-butoxycarbonyl)-4-ethoxycarbonylamino-4-piperidylmethyl]-4-(6-chloronaphthalene-2-sulfonyl)-2-piperazinone Triethylamine (0.836 ml) and diphenylphosphoryl azide (1.29 ml) were added to a solution of 1-(tert-butoxycarbonyl)-4-[4-(6-chloro-2-naphthalenesulfonyl)-2-oxo-1-piperazinylmethyl]isonicopetinic acid (2.83 g) in toluene(50 ml), and the mixture was stirred at 100° C. for 30 minutes. Ethanol (30 ml) was added to the reaction mixture, and the mixture was further stirred at 70° C. overnight. The reaction solution was concentrated under reduced pressure, ethyl acetate was added thereto, and the mixture was washed successively with an aqueous saturated sodium bicarbonate solution and an aqueous saturated sodium chloride solution, dried and concentrated to obtain the amorphous title compound (3.90 g).

$^1$H-NMR (CDCl$_3$) δ: 1.22 (3H, t, J=7.1 Hz), 1.43 (9H, s), 1.40–2.00 (4H, m), 2.80–3.00 (2H, m), 3.30–3.42 (2H, m), 3.48–3.60 (2H, m), 3.67 (2H, s), 3.80 (2H, s), 3.65–3.90 (2H, m), 4.04 (2H, q, J=7.1 Hz), 4.42 (1H, brs), 7.61 (1H, dd, J=8.9, 1.9 Hz), 7.80 (1H, dd, J=8.6, 1.6 Hz), 7.92–8.00 (3H, m), 8.36 (1H, s).

EXAMPLE 1-2

4-(6-Chloronaphthalene-2-sulfonyl)-1-[4-ethoxycarbonylamino-1-(4-pyridyl)-4-piperidylmethyl]-2-piperazinone A 4N hydrochloric acid solution in ethyl acetate (30 ml) and ethanol (6 ml) were added to 1-[1-(tert-butoxycarbonyl)-4-ethoxycarbonylamino-4-piperidyl]-4-(6-chloronaphthalene-2-sulfonyl)-2-piperazinone (5.21 g), and the mixture was stirred at room temperature for 1 hour. The reaction mixture was concentrated, the precipitated crystals were filtered off, washed with ethyl acetate-ethanol, and dried to obtain 1-[4-ethoxycarbonylamino-4-piperidylmethyl]-4-(6-chloronaphthalene-2-sulfonyl)-2-piperazinone hydrochloride (3.71 g). A solution of 1-[4-ethoxycarbonylamino-4-piperidylmethyl]-4-(6-chloronaphthalene-2-sulfonyl)-2-piperazinone hydrochloride (3.40 g), 4-chloropyridine hydrochloride (1.12 g) and triethylamine (3.48 ml) in ethanol (100 ml) was reacted at 150° C. for 9 hours in a sealed tube. The reaction mixture was concentrated under reduced pressure, ethyl acetate was added thereto, and the mixture was washed with a 5% aqueous sodium carbonate solution and water, and concentrated. The resulting residue was purified by silica gel column chromatography (ethyl acetate: 10% aqueous ammonia-containing methanol=95:5→80:20), and the precipitated crystals were washed with ethanol-ether to obtain the colorless crystalline title compound (1.52 g).

$^1$H-NMR (CDCl$_3$) δ: 1.22 (3H, t, J=7.1 Hz), 1.60–2.05 (4H, m), 2.86–3.05 (2H, m), 3.33–3.42 (2H, m), 3.46–3.65 (4H, m), 3.71 (2H, s), 3.81 (2H, s), 4.05 (2H, q, J=7.1 Hz), 4.55 (1H, brs), 6.62 (2H, d, J=6.5 Hz), 7.62 (1H, dd, J=8.9, 1.9 Hz), 7.81 (1H, dd, J=8.6, 1.8 Hz), 7.90–8.00 (3H, m), 8.26 (2H, d, J=6.5 Hz), 8.36 (1H, s).

EXAMPLE 2

4-(6-Chloronaphthalene-2-sulfonyl)-1-[4-ethoxycarbonylamino-1-(4-pyridyl)-4-piperidylmethyl]-2-piperazinone hydrochloride Ethanol (20 ml) and a 4N hydrochloric acid solution in ethyl acetate (2 ml) were added to 4-(6-chloronaphthalene-2-sulfonyl)-1-[4-ethoxycarbonylamino-1-(4-pyridyl)-4-piperidylmethyl]-2-piperazinone (1.3 g) obtained in Example 1, to dissolve the material. Subsequently, ethyl acetate (200 ml) and ether (200 ml) were added, the resulting precipitates were filtered off, and washed with ether to obtain the colorless amorphous title compound (1.26 g).

$^1$H-NMR (DMSO-d$_6$) δ: 1.15 (3H, t, J=7.0 Hz), 1.47 (2H, m), 2.11 (2H, m), 3.05–3.55 (8H, m), 3.63 (2H, s), 3.90–4.05 (4H, m), 7.15 (2H, d, J=6.6 Hz), 7.17 (1H, brs), 7.74 (1H, dd, J=2.2, 8.8 Hz), 7.88 (1H, dd, J=1.8, 8.8 Hz), 8.15–8.33 (5H, m), 8.59 (1H, s).

EXAMPLE 3

4-(6-Chloronaphthalene-2-sulfonyl)-1-[4-methoxycarbonylamino-1-(4-pyridyl)-4-piperidylmethyl]-2-piperazinone According to the same manner as that of Example 1, 1-(tert-butoxycarbonyl)-4-[4-(6-chloro-2-naphthalenesulfonyl)-2-oxo-1-piperazinylmethyl]isonipecotinic acid and methanol were used to obtain the colorless crystalline title compound.

$^1$H-NMR (CDCl$_3$) δ: 1.60–2.10 (4H, m), 2.87–3.06 (2H, m), 3.33–3.42 (2H, m), 3.50–3.60 (4H, m), 3.63 (3H, s), 3.71 (2H, s), 3.82 (2H, s), 4.64 (1H, brs), 6.61 (2H, d, J=6.5 Hz), 7.62 (1H, dd, J=8.9, 1.9 Hz), 7.80 (1H, dd, J=8.6, 1.8 Hz), 7.92–8.00 (3H, m), 8.25 (2H, d, J=6.5 Hz), 8.36 (1H, s).

EXAMPLE 4

4-(6-Chloromaphtalene-2-sulfonyl)-1-[4-propoxycarbonylamino-1-(4-pyridyl)-4-piperidylmethyl]-2-piperadinon

EXAMPLE 4-1

O-Propoxycarbonyl-4-nitrophenol

A solution of propyl chloroformate (613 mg) in THF (3 ml) was added to a solution of 4-nitrophenol (693 mg) and triethylamine (0.836 ml) in THF (10 ml) at 0° C. After stirred at room temperature for 30 minutes, water was added, and the mixture was extracted with ethyl acetate. The organic layer was washed with a 10% aqueous sodium carbonate solution, an aqueous saturated sodium bicarbonate solution and an aqueous saturated sodium chloride solution, dried, and concentrated to obtain the title compound (1.11 g) as a pale yellow solid.

$^1$H-NMR (CDCl$_3$) δ: 1.03 (3H, t, J=7.4 Hz), 1.70–1.90 (2H, m), 4.26 (2H, t, J=6.7 Hz), 7.39 (2H, d, J=9.3 Hz), 8.29 (2H, d, J=9.3 Hz).

EXAMPLE 4-2

4-(6-Chloronaphthalene-2-sulfonyl)-1-[4-propoxycarbonylamino-1-(4-pyridyl)-4-piperidylmethyl]-2-piperazinone A solution of 1-[4-amino-1-(4-pyridyl)-4-piperidylmethyl]-4-(6-chloronaphthalene-2-sulfonyl)-2-piperazinone dihydrochloride (235 mg), O-propoxycarbonyl-4-nitrophenol (270 mg) and N-ethyldiisopropylamine (0.348 ml) in DMF (5 ml) was stirred at 80° C. overnight. To the reaction solution was added ethyl acetate, the mixture was washed successively with a 10% aqueous sodium carbonate solution, an aqueous saturated sodium bicarbonate solution and an aqueous saturated sodium chloride solution, dried, and concentrated. The residue was purified by silica gel column chromatography (ethyl acetate:10% aqueous ammonia-containing methanol=90:10→80:20), and crystallized from a mixed solution of acetone and ethyl acetate to obtain the pale brown crystalline title compound (114 mg).

$^1$H-NMR (CDCl$_3$) δ: 0.92 (3H, t, J=7.5 Hz), 1.50–2.05 (6H, m), 2.88–3.05 (2H, m), 3.32–3.42 (2H, m), 3.48–3.64 (4H, m), 3.71 (2H, s), 3.81 (2H, s), 3.96 (2H, q, J=6.8 Hz), 4.54 (1H, brs), 6.61 (2H, d, J=6.6 Hz), 7.62 (1H, dd, J=9.0, 2.0 Hz), 7.80 (1H, dd, J=8.4, 1.8 Hz), 7.90–8.00 (3H, m), 8.25 (2H, d, J=6.8 Hz), 8.35 (1H, s).

EXAMPLE 5

4-(7-Chloro-2H-benzopyran-3-sulfonyl)-1-[4-methoxycarbonylamino-1-(4-pyridyl)-4-piperidylmethyl]-2-piperazinone According to the same manner as that of Example 1, 1-(tert-butoxycarbonyl)-4-[4-(7-chloro-2H-benzopyran-3-sulfonyl)-2-oxo-1-piperazinylmethyl]isonipecotinic acid and methanol were used to obtain the colorless crystalline title compound $^1$H-NMR (CDCl$_3$) δ: 1.68–1.88 (2H, m), 2.00–2.20 (2H, m), 2.94–3.13 (2H, m), 3.50–3.68 (6H, m), 3.63 (3H, s), 3.79 (2H, s), 3.93 (2H, s), 4.80 (1H, brs), 4.89 (2H, s), 6.64 (2H, d, J=6.6 Hz), 6.94 (1H, d, J=1.9 Hz), 7.02 (1H, dd, J=8.0, 1.9 Hz), 7.15 (1H, d, J=8.0 Hz), 7.29 (1H, s), 8.27 (2H, d, J=6.6 Hz).

EXAMPLE 6

4-(7-Chloro-2H-benzopyran-3-sulfonyl)-1-[4-ethoxycarbonylamino-1-(4-pyridyl)-4-piperidylmethyl]-2-piperazinone According to the same manner as that of Example 1, 1-(tert-butoxycarbonyl)-4-[4-(7-chloro-2H-benzopyran-3-sulfonyl)-2-oxo-1-piperazinylmethyl]isonipecotinic acid and ethanol were used to obtain the colorless crystalline title compound.

$^1$H-NMR (CDCl$_3$) δ: 1.21 (3H, t, J=7.2 Hz), 1.70–1.88 (2H, m), 2.00–2.20 (2H, m), 2.95–3.13 (2H, m), 3.50–3.70 (6H, m), 3.80 (2H, s), 3.94 (2H, s), 4.06 (2H, q, J=7.2 Hz), 4.79 (1H, brs), 4.89 (2H, s), 6.64 (2H, d, J=6.6 Hz), 6.94 (1H, d, J=1.9 Hz), 7.02 (1H, dd, J=8.1, 1.9 Hz), 7.15 (1H, d, J=8.1 Hz), 7.30 (1H, s), 8.27 (2H, d, J=6.6 Hz).

EXAMPLE 7

4-(7-Chloro-2H-benzopyran-3-sulfonyl)-1-[4-propoxycarbonylamine-1-(4-pyridyl)-4-piperidylmethyl]-2-piperazinone According to the same manner as that of Example 1, 1-(tert-butoxycarbonyl)-4-[4-(7-chloro-2H-benzopyran-3-sulfonyl)-2-oxo-1-piperazinylmethyl]isonicopetinic acid and propanol were used to obtain the colorless amorphous title compound.

$^1$H-NMR (CDCl$_3$) δ: 0.91 (3H, t, J=7.5 Hz), 1.50–1.90 (4H, m), 2.00–2.20 (2H, m), 2.95–3.15 (2H, m), 3.50–3.70 (6H, m), 3.80 (2H, s), 3.94 (2H, s), 3.97 (2H, q, J=7.0 Hz), 4.74 (1H, brs), 4.89 (2H, s), 6.64 (2H, d, J=6.4 Hz), 6.94 (1H, d, J=1.8 Hz), 7.02 (1H, dd, J=8.0, 1.9 Hz), 7.15 (1H, d, J=8.0 Hz), 7.30 (1H, s), 8.27 (2H, d, J=6.4 Hz).

EXAMPLE 8

1-[4-Methoxycarbonylamino-1-(4-pyridyl)-4-piperidylmethyl]-4-vinylbenzensulfonyl-2-piperazinone According to the same manner as that of Example 1, 1-(tert-butoxycarbonyl)-4-[2-oxo-4-(4-vinylbenzenesulfonyl)-1-piperazinylmethyl]isonicopetinic acid and methanol were used to obtain the colorless crystalline title compound.

$^1$H-NMR (CDCl$_3$) δ: 1.65–1.85 (2H, m), 1.95–2.12 (2H, m), 2.94–3.13 (2H, m), 3.25–3.35 (2H, m), 3.48–3.65 (4H, m), 3.64 (3H, s), 3.72 (2H, s), 3.75 (2H, s), 4.66 (1H, brs), 5.49 (1H, d, J=11.0 Hz), 5.91 (1H, d, J=17.5 Hz), 6.63 (2H, d, J=6.4 Hz), 6.77 (1H, dd, J=17.5, 11.0 Hz), 7.58 (2H, d, J=8.4 Hz), 7.76 (2H, d, J=8.4 Hz), 8.26 (2H, d, J=6.4 Hz).

EXAMPLE 9

1-[4-Ethoxycarbonylamino-1-(4-pyridyl)-4-piperidylmethyl]-4-vinylbenzensulfonyl-2-piperazinone According to the same manner as that of Example 1, 1-(tert-butoxycarbonyl)-4-[2-oxo-4-(4-vinylbenzenesulfonyl)-1-piperazinylmethyl]isonipecotinic acid and ethanol were used to obtain the colorless crystalline title compound.

$^1$H-NMR (CDCl$_3$) δ: 1.24 (3H, t, J=7.1 Hz), 1.65–1.85 (2H, m), 1.95–2.10 (2H, m), 2.95–3.12 (2H, m), 3.27–3.36 (2H, m), 3.50–3.68 (4H, m), 3.73 (2H, s), 3.75 (2H, s), 4.07 (2H, q, J=7.1 Hz), 4.61 (1H, brs), 5.49 (1H, d, J=10.9 Hz), 5.92 (1H, d, J=17.6 Hz), 6.64 (2H, d, J=6.6 Hz), 6.77 (1H, dd, J=17.6, 10.9 Hz), 7.59 (2H, d, J=8.4 Hz), 7.76 (2H, d, J=8.4 Hz), 8.26 (2H, d, J=6.6 Hz).

EXAMPLE 10

1-[4-Propoxycarbonylamino-1-(4-pyridyl)-4-piperidylmethyl]-4-vinylbenzensulfonyl-2-piperazinone According to the same manner as that of Example 1, 1-(tert-butoxycarbonyl)-4-[2-oxo-4-(4-vinylbenzenesulfonyl)-1-piperazinylmethyl]isonipecotinic acid and propanol were used to obtain the pale yellow amorphous title compound.

$^1$H-NMR (CDCl$_3$) δ: 0.94 (3H, t, J=7.4 Hz), 1.55–1.90 (4H, m), 2.00–2.20 (2H, m), 3.10–3.37 (4H, m), 3.50–3.80 (8H, m), 3.98 (2H, q, J=6.8 Hz), 4.74 (1H, brs), 5.49 (1H, d, J=10.9 Hz), 5.92 (1H, d, J=17.7 Hz), 6.68–6.86 (3H, m), 7.59 (2H, d, J=8.4 Hz), 7.75 (2H, d, J=8.4 Hz), 8.19 (2H, d, J=6.6 Hz).

EXAMPLE 11

4-(6-Chloronaphthalene-2-sulfonyl)-1-[4-(2-methoxyethoxycarbonylamino)-1-(4-pyridyl)-4-piperidylmethyl]-2-piperazinone

EXAMPLE 11-1

2-Methoxyethyl-4-nitrophenyl carbonate

A solution of 4-nitrophenyl chloroformate (1.01 g) in THF (3 ml) was added to a solution of 2-methoxyethanol (381 mg) and triethylamine (0.836 ml) in THF (10 ml) at 0° C. After stirred at 0° C. for 5 hours, water was added, and the mixture was extracted with ethyl acetate. The organic layer was washed with a 10% aqueous sodium carbonate solution, an aqueous saturated sodium bicarbonate solution and an aqueous saturated sodium chloride solution, dried, and concentrated to obtain the title compound (1.11 g) as a pale yellow solid.

¹H-NMR (CDCl₃) δ: 3.45 (3H, s), 3.68–3.75 (2H, m), 3.42–3.48 (2H, m), 7.40 (2H, d, J=9.3 Hz), 8.29 (2H, d, J=9.3 Hz).

EXAMPLE 11-2

4-(6-Chloronaphthalene-2-sulphonyl)-1-[4-(2-methoxyethoxycarbonylamino)-1-(4-pyridyl)-4-piperidylmethyl]-2-piperazinone A solution of 1-[4-amino-1-(4-pyridyl)-4-piperidylmethyl]-4-(6-chloronaphthalene-2-sulfonyl)-2-piperazinone (206 mg), 2-methoxyethyl-4-nitrophenyl carbonate (386 mg) and N-ethyldiisopropylamine (0.278 ml) in DMF (5 ml) was stirred at 60° C. overnight. The reaction mixture was concentrated under reduced pressure, ethyl acetate was added, the mixture was washed successively with a 10% aqueous sodium carbonate solution, an aqueous saturated sodium bicarbonate solution and an aqueous saturated sodium chloride solution, dried, and concentrated. The residue was purified by silica gel column chromatography (ethyl acetate:10% aqueous ammonia-methanol=90:10→80:20), and crystallized from a mixed solution of acetone and ethyl acetate to obtain the colorless crystalline title compound (145 mg).

¹H-NMR (CDCl₃) δ: 1.60–2.00 (4H, m), 2.85–3.05 (2H, m), 3.34–3.45 (2H, m), 3.40 (3H, s), 3.46–3.62 (6H, m), 3.70 (2H, s), 3.82 (2H, s), 4.15–4.24 (2H, m), 4.63 (1H, brs), 6.61 (2H, d, J=6.4 Hz), 7.62 (1H, dd, J=8.8, 2.0 Hz), 7.81 (1H, dd, J=8.6, 1.6 Hz), 7.92–8.00 (3H, m), 8.26 (2H, d, J=6.4 Hz), 8.37 (1H, s).

EXAMPLE 12

4-(6-Chloronaphthalene-2-sulfonyl)-1-[4-(2-fluoroethoxycarbonylamino)-1-(4-pyridyl)-4-piperidylmethyl]-2-piperazinone According to the same manner as that of Example 11, 2-fluoroethanol was used in place of 2-methoxyethanol, to obtain the pale brown crystalline title compound.

¹H-NMR (CDCl₃) δ: 1.60–1.80 (2H, m), 1.90–2.05 (2H, m), 2.87–3.05 (2H, m), 3.32–3.43 (2H, m), 3.45–3.62 (4H, m), 3.70 (2H, s), 3.82 (2H, s), 4.17–4.38 (2H, m), 4.41–4.73 (3H,m), 6.62 (2H, d, J=6.6 Hz), 7.62 (1H, dd, J=8.9, 1.9 Hz), 7.81 (1H, dd, J=8.8, 1.8 Hz), 7.90–8.00 (3H, m), 8.26 (2H, d, J=6.6 Hz), 8.36 (1H, s).

EXAMPLE 13

Ethyl 2-[4-[4-(6-chloro-2-naphthalensulfonyl)-2-oxo-1-piperazinylmethyl]-1-(4-pyridyl)-4-piperidylaminocarbonyloxy]acetate According to the same manner as that of Example 11, ethyl glycolate was used in place of 2-methoxyethanol, to obtain the colorless crystalline title compound.

¹H-NMR (CDCl₃) δ: 1.29 (3H, t, J=7.2 Hz), 1.60–2.00 (4H, m), 2.85–3.05 (2H, m), 3.37–3.73 (6H, m), 3.69 (2H, s), 3.84 (2H, s), 4.21 (2H, q, J=7.2 Hz), 4.52 (2H, s), 4.91 (1H, brs), 6.61 (2H, d, J=6.6 Hz), 7.62 (1H, dd, J=9.0, 1.8 Hz), 7.80 (1H, dd, J=8.8, 1.8 Hz), 7.90–8.00 (3H, m), 8.25 (2H, d, J=6.6 Hz), 8.37 (1H, s).

EXAMPLE 14

4-(6-Chloronaphthalene-2-sulfonyl)-1-[4-isopropoxycarbonylamino-1-(4-pyridyl)-4-piperidylmethyl]-2-piperazinone According to the same manner as that of Example 11, isopropanol was used in place of 2-methoxyethanol, to obtain the colorless crystalline title compound.

¹H-NMR (CDCl₃) δ: 1.21 (6H, d, J=6.4 Hz), 1.60–2.05 (4H, m), 2.85–3.05 (2H, m), 3.32–3.44 (2H, m), 3.48–3.53 (4H, m), 3.71 (2H, s), 3.82 (2H, s), 4.42 (1H, brs), 4.75–4.92 (1H, m), 6.61 (2H, d, J=5.7 Hz), 7.62 (1H, d, J=9.0 Hz), 7.80 (1H, dd, J=8.8, 1.8 Hz), 7.90–8.00 (3H, m), 8.26 (2H, d, J=5.7 Hz), 8.36 (1H, s).

EXAMPLE 15

2-[4-[4-(6-Chloro-2-naphthalensulfonyl)-2-oxo-1-piperazinylmethyl]-1-(4-pyridyl)-4-peperidylaminocarbonyloxy]acetic acid A mixture of ethyl 2-[4-[4-(6-chloro-2-naphthalenesulfonyl)-2-oxo-1-piperazinylmethyl]-1-(4-pyridyl)-4-piperidylaminocarbonyloxy]acetate (130 mg) obtained in Example 13, 1N sodium hydroxide (0.4 ml), methanol (10 ml) and dichloromethane (5 ml) was stirred at room temperature overnight. After neutralized with 1N hydrochloric acid, the reaction mixture was concentrated under reduced pressure, and the resulting residue was purified by CHP20 column chromatography (water:acetonitrile=10:0→6:4). 1N hydrochloric acid (0.3 ml) was added to the desired fraction, and the fraction was concentrated under reduced pressure to obtain the colorless amorphous title compound (78 mg).

¹H-NMR (DMSO-d₆) δ: 1.35–1.62 (2H, m), 2.00–2.18 (2H, m), 3.10–3.70 (8H, m), 3.64 (2H, s), 3.90–4.08 (2H, m), 4.48 (2H, s), 7.17 (2H, d, J=7.2 Hz), 7.55 (1H, brs), 7.75 (1H, dd, J=8.8, 2.0 Hz), 7.89 (1H, dd, J=8.6, 1.6 Hz), 8.14–8.35 (5H, m), 8.60 (1H, s).

EXAMPLE 16

4-(7-Chloro-2H-benzopyran-3-sulfonyl)-1-[1-(4-pyridyl)-4-[2-(1-pyrrolidinyl)ethoxycarbonylamino]-4-piperidinylmethyl]-2-piperazinone dihydrochloride A 4N hydrochloric acid solution in ethyl acetate (10 ml) and ethanol (2 ml) were added to 1-[1-(tert-butoxycarbonyl)-4-[2-(1-pyrrolidinyl)ethoxycarbonylamino]-4-piperidylmethyl]-4-(7-chloro-2H-benzopyran-3-sulfonyl)-piperazinone (460 mg) obtained in the same method as that in Example 7-1 using 1-(tert-butoxycarbonyl)-4-[4-(7-chloro-2H-benzopyran-3-sulfonyl)-2-oxo-1-piperazinylmethyl] isonipecotinic acid and 2-hydroxypyrrolidine, and the mixture was stirred at room temperature for 1 hour. The reaction solution was concentrated under reduced pressure, 4-chloropyridine hydrochloride (112 mg), N-ethyldiisopropylamine (0.587 ml), tetrabutylammonium bromide (22 mg), and 2-methoxyethanol (10 ml) were added to the resulting residue, to react at 120° C. for 2 days. Ethyl acetate was added to the reaction solution, and the mixture was washed with 5% aqueous sodium carbonate and an aqueous saturated sodium chloride solution, dried, and concentrated. The resulting residue was purified by basic silica gel column chromatography (ethyl acetate:ethanol=10:0→9:1). 1N Hydrochloric acid was added to the desired fraction, and the fraction was purified again by CHP20 column chromatography (water:acetonitrile:1N hydrochloric acid=100:0: 0.5→70:30:0.5) to obtain the pale yellow amorphous title compound (167 mg).

$^1$H-NMR (DMSO-$d_6$) δ 1.45–1.75 (2H, m), 1.75–2.10 (4H, m), 2.10–2.30 (2H, m), 2.90–3.70 (14H, m), 3.80 (2H, s), 3.97–4.14 (2H, m), 4.22–4.34 (2H, m), 5.01 (2H, s), 7.08 (1H, d, J=1.8 Hz), 7.12 (1H, dd, J=8.1, 1.8 Hz), 7.20 (2H, d, J=7.4 Hz), 7.43 (1H, brs), 7.49 (1H, d, J=8.1 Hz), 7.50 (1H, s), 8.16–8.27 (2H, m).

EXAMPLE 17

Ethyl 4-[[4-[(6-bromo-2-naphthyl)sulfonyl]-2-oxo-1-piperazinyl]methyl]-1-(4-pyridinyl)-4-piperidinylcarbamate A mixture of benzyl 4-[[4-[(ethoxycarbonyl)amino]-1-(4-pyridinyl)-4-piperidinyl]methyl]-3-oxo-1-piperidinecarboxylate (3.27 g) obtained in Reference Example 9, 4N hydrochloric acid/ethyl acetate (1.65 ml), 10% Pd—C (0.33 g) and methanol (65 ml) was stirred for 1 hour under the hydrogen atmosphere. The catalyst was removed by filtration, and the filtrate was concentrated under reduced pressure. Then, to a stirring mixture of the resulting oil, sodium carbonate (3.50 g), methylene chloride (30 ml) and water (30 ml) was added 6-bromonaphthalenesulfonyl chloride (2.42 g) at room temperature, and the mixture was stirred at room temperature for 2 hours. The reaction mixture was separated into layers, the organic layer was washed with 1N sodium hydroxide and water, dried with magnesium sulfate, and concentrated under reduced pressure. The residue was purified by silica gel chromatography (methylene chloride/methanol=10/1-methylene chloride/methanol/25% aqueous ammonia=100/10/1) to obtain the pink crystalline title compound (2.4 g, 56%).

$^1$H-NMR (CDCl$_3$): δ 1.22 (3H, t, J =7.0 Hz), 1.57–1.83 (2H, m), 1.85–2.06 (2H, m), 2.85–3.07 (2H, m), 3.33–3.43 (2H, m), 3.45–3.65 (4H, m), 3.70 (2H, s), 3.81 (2H, s), 4.05 (2H, q, J =7.0 Hz), 4.56 (1H, s), 6.61 (2H, d, J =6.4 Hz), 7.70–7.98 (4H, m), 8.13 (1H, d, J =1.4 Hz), 8.25 (2H, d, J=6.4 Hz), 8.35 (1H, s).

EXAMPLE 18

Ethyl 4-[[4-[(6-bromo-2-naphthyl)sulfonyl]-2-oxo-1-piperazinyl]methyl]-1-(4-pyridyl)-4-piperidinylcarbamate hydrochloride Ethyl 4-[[4-[(6-bromo-2-naphthyl)sulfonyl]-2-oxo-1-piperazinyl]methyl]-1-(4-pyridinyl)-4-piperidinylcarbamate (2.0 g) obtained in Example 17 was suspended in ethanol (20 ml), and 4N hydrochloric acid/ethyl acetate (1.2 ml) was added thereto at room temperature, followed by concentration under reduced pressure. The residue was dissolved in ethanol (8 ml), and ethyl acetate (50 ml) and diethyl ether (50 ml) were added. The resulting powders were collected to obtain the title compound (1.82 g) as colorless powders.

$^1$H-NMR (DMSO-$d_6$+D$_2$O): δ 1.16 (3H, t, J=7.0 Hz), 1.35–1.58 (2H, m), 2.00–2.20 (2H, m), 3.05–4.10 (14H, m), 7.08–7.22 (5H, m), 7.80–7.94 (2H, m), 8.12–8.26 (4H, m), 8.43 (1H, d, J=1.4 Hz), 8.58 (1H, s).

EXAMPLE 19

Ethyl 4-[[4-[(7-bromo-2H-chromen-3-yl)sulfonyl]-2-oxo-1-piperazinyl]methyl]-1-(4-pyridinyl)-4-piperidinylcarbamate According to the same manner as that of Example 17, 7-bromo-3-benzopyranylsulfonyl chloride was used in place of 6-bromonaphthalene-2-sulfonyl chloride, to obtain the colorless crystalline title compound.

$^1$H-NMR (CDCl$_3$): δ 1.21 (3H, t, J=7.0 Hz), 1.67–1.90 (2H, m), 2.00–2.18 (2H, m), 2.93–3.15 (2H, m), 3.47–3.70 (6H, m), 3.79 (2H, s), 3.94 (2H, s), 4.06 (2H, q, J=7.0 Hz), 4.79 (1H, s), 4.88 (2H, s), 6.64 (2H, d, J=6.6 Hz), 7.02–7.12 (2H, m), 7.18 (1H, dd, J=2.0, 8.2 Hz), 7.28 (1H, s), 8.26 (2H, d, J=6.6 Hz).

EXAMPLE 20

Ethyl 4-[[4-[(7-bromo-2H-chromen-3-yl)sulfonyl]-2-oso-1-piperazinyl]methyl]-1-(4-pyridinyl)-4-piperidinylcarbamate hydrochloride According to the same manner as that of Example 18, the title compound as colorless powders was obtained from a free compound.

$^1$H-NMR (DMSO-$d_6$+D$_2$O): δ 1.17 (3H, t, J=7.0 Hz), 1.40–1.68 (2H, m), 2.05–2.30 (2H, m), 3.10–4.20 (14H, m), 4.98 (2H, s), 7.04–7.54 (6H, m), 8.20 (2H, d, J=7.0 Hz).

EXAMPLE 21

4-(6-Chloronaphthalene-2-sulfonyl)-1-{[4-ethoxycarbonylamino-1-(2-methyl-4-pyridyl)-4-piperidinyl]methyl}-2-piperazinone Triethylamine (253 mg) was added to a solution of 1-{[4-ethoxycarbonylamino-1-(2-methyl-4-pyridyl)-4-piperidinyl]methyl}-2-piperazinone hydrochloride (258 mg) in dichloromethane (15 ml), 6-chloronaphthalene-2-sulfonyl chloride (196 mg) was added thereto at 0° C., and the mixture was stirred at room temperature for 1 hour. To the reaction solution was added an aqueous sodium carbonate solution, the mixture was extracted with dichloromethane, dried, concentrated, and purified by column chromatography (dichloromethane:10% aqueous ammonia-containing methanol=20:1) to obtain the colorless amorphous title compound (255 mg).

$^1$H-NMR (CDCl$_3$) δ: 1.22 (3H, t, J=7.0 Hz), 1.70 (2H, m), 1.96 (2H, m), 2.45 (3H, s), 2.96 (2H, m), 3.37 (2H, m), 3.45–3.60 (4H, m), 3.70 (2H, s), 3.81 (2H, s), 4.05 (2H, q, J=7.0 Hz), 4.48 (1H, s), 6.40–6.55 (2H, m), 7.62 (1H, dd, J=1.8, 8.8 Hz), 7.80 (1H, dd, J=1.8, 8.8 Hz), 7.90–8.00 (3H, m), 8.16 (1H, d, J=6.2 Hz), 8.36 (1H, s). IR (KBr): 1715, 1651, 1601, 1539, 1495, 1348, 1262, 1167, 1078 cm$^{-1}$.

EXAMPLE 22

4-(6-Chloronaphthalene-2-sulfonyl)-1-{[4-ethoxycarbonylamino-1-(2-methyl-4-pyridyl)-4-piperidinyl]methyl}-2-piperazinone hydrochloride 4-(6-Chloronaphthalene-2-sulfonyl)-1-{[4-ethoxycarbonylamino-1-(2-methyl-4-pyridyl)-4-piperidinyl]methyl}-2-piperazinone (215 mg) was suspended in ethyl acetate (10 ml), a 4N hydrochloric acid solution in ethyl acetate (0.3 ml)

was added, and the resulting crystals were filtered off to obtain the title compound (180 mg) as colorless powders.

$^1$H-NMR (DMSO-d$_6$) δ: 1.16 (3H, t, J=7.0 Hz), 1.45 (2H, m), 2.11 (2H, m), 2.43 (3H, s), 3.08–3.60 (8H, m), 3.63 (2H, s), 3.90–4.05 (4H, m), 7.00–7.10 (2H, m), 7.17 (1H, s), 7.75 (1H, dd, J=2.2, 8.8 Hz), 7.89 (1H, dd, J=2.0, 8.8 Hz), 8.09 (1H, m), 8.20 (1H, d, J=8.8 Hz), 8.25–8.35 (2H, m), 8.60 (1H, s). IR KBr): 3052, 1713, 1644, 1630, 1537, 1346, 1252, 1163 cm$^{-1}$.

EXAMPLE 23

4-(7-Bromo-2H-benzopyran-3-sulfonyl)-1-{[4-ethoxycarbonylamino-1-(2-methyl-4-pyridyl)-4-piperidinyl]methyl}-2-piperazinone hydrochloride Triethylamine (253 mg) was added to a solution of 1-{[4-ethoxycarbonylamino-1-(2-methyl-4-pyridyl)-4-piperidinyl]methyl}-2-piperazinone hydrochloride (258 mg) in dichloromethane (15 ml), 7-bromo-2H-benzopyran-3-sulfonyl chloride (233 mg) was added at 0° C., and the mixture was stirred at room temperature for 1 hour. To the reaction solution was added an aqueous sodium carbonate solution, the mixture was extracted with dichloromethane, dried, concentrated, and purified by column chromatography (dichloromethane:10% aqueous ammonia-containing methanol=20:1) to obtain colorless amorphous 4-(7-bromo-2H-benzopyran-3-sulfonyl)-1-{[4-ethoxycarbonylamino-1-(2-methyl-4-pyridyl)-4-piperidinyl]methyl}-2-piperazinone (169 mg).

$^1$H-NMR (CDCl$_3$) δ: 1.20 (3H, t, J=7.0 Hz), 1.77 (2H, m), 2.08 (2H, m), 2.45 (3H, s), 3.04 (2H, m), 3.45–3.70 (6H, m), 3.79 (2H, s), 3.94 (2H, s), 4.05 (2H, q, J=7.0 Hz), 4.75 (1H, s), 4.88 (2H, d, J=1.0 Hz), 6.40–6.60 (2H, m), 7.08 (1H, d, J=8.0 Hz), 7.11 (1H, d, J=1.8 Hz), 7.18 (1H, dd, J=1.8, 8.0 Hz), 7.28 (1H, d, J=1.0 Hz), 8.16 (1H, d, J=5.8 Hz).

The present product was suspended in ethyl acetate (10 ml), a 4N hydrochloric acid solution in ethyl acetate (0.3 ml) was added, and the resulting crystals were filtered off to obtain the title compound (137 mg) as colorless powders.

$^1$H-NMR (DMSO-d$_6$) δ: 1.17 (3H, t, J=7.0 Hz), 1.51 (2H, m), 2.16 (2H, m), 2.44 (3H, s), 3.10–3.65 (8H, m), 3.77 (2H, s), 3.90–4.10 (4H, m), 4.98 (2H, s), 7.00–7.13 (2H, m), 7.18–7.28 (3H, m), 7.41 (1H, d, J=8.0 Hz), 7.48 (1H, s), 8.10 (1H, t, J=6.0 Hz). IR (KBr): 3054, 1713, 1644, 1537, 1254, 1159 cm$^{-1}$.

EXAMPLE 24

1-{[4-Ethoxycarbonylamino-1-(2-methyl-4-pyridyl)-4-piperidinyl]methyl}-4-(4-vinylbenzenesulfonyl)-2-piperazinone Triethylamine (260 mg) was added to a solution of 1-{[4-ethoxycarbonylamino-1-(2-methyl-4-pyridyl)-4-piperidinyl]methyl}-2-piperazinone hydrochloride (263 mg) in dichloromethane (20 ml), 4-vinylbenzenesulfonyl chloride (194 mg) was added at 0° C., and the mixture was stirred at room temperature for 1 hour. To the reaction solution was added an aqueous sodium carbonate solution, the material was extracted with dichloromethane, dried, concentrated, purified by column chromatography (dichloromethane:10% aqueous ammonia-containing methanol=20:1), and crystallized from diisopropyl ether to obtain the colorless crystalline title compound (157 mg).

$^1$H-NMR (CDCl$_3$) δ: 1.24 (3H, t, J=7.0 Hz), 1.73 (2H, m), 2.00 (2H, m), 2.45 (3H, s), 3.02 (2H, m), 3.30 (2H, m), 3.50–3.70 (4H, m), 3.72 (2H, s), 3.75 (2H, s), 4.06 (2H, q, J=7.0 Hz), 4.51 (1H, s), 5.49 (2H, d, J=11.0 Hz), 5.92 (1H, d, J=17.6 Hz), 6.45–6.55 (2H, m), 6.77 (1H, dd, J=11.0, 17.6 Hz), 7.58 (2H, d, J=8.4 Hz), 7.76 (2H, d, J=8.4 Hz), 8.16 (1H, d, J=5.8 Hz). IR (KBr): 1713, 1644, 1599, 1352, 1262, 1167 cm$^{-1}$.

EXAMPLE 25

1-{[4-Ethoxycarbonylamino-1-(2-methyl-4-pyridyl)-4-piperidinyl]methyl}-4-(4-vinylbenzenesulfonyl)-2-piperazinone hydrochloride 1-{[4-Ethoxycarbonylamino-1-(2-methyl-4-pyridyl)-4-piperidinyl]methyl}-4-(4-vinylbenzenesulfonyl)-2-piperazinone (86 mg) was suspended in ethyl acetate (10 ml), a 4N hydrochloric acid solution in ethyl acetate (0.3 ml) was added, and the resulting crystals were filtered off to obtain the title compound (38 mg) as colorless powders.

$^1$H-NMR (DMSO-d$_6$) δ: 1.17 (3H, t, J=7.0 Hz), 1.47 (2H, m), 2.13 (2H, m), 2.44 (3H, s), 3.10–3.60 (10H, m), 3.90–4.07 (4H, m), 5.50 (2H, d, J=11.0 Hz), 6.07 (1H, d, J=17.6 Hz), 6.87 (1H, dd, J=11.0, 17.6 Hz), 7.00–7.10 (2H, m), 7.19 (1H, s), 7.78 (4H, s), 8.10 (1H, d, J=7.2 Hz). IR (KBr): 3050, 1713, 1644, 1537, 1348, 1254, 1167 cm$^{-1}$.

EXAMPLE 26

1-{[4-Ethoxycarbonylamino-1-(2-hydroxymethyl-4-pyridyl)-4-piperidinyl]methyl}-4-(4-vinylbenzensulfonyl)-2-piperazinone 4-Chloro-2-(hydroxymethyl)pyridine (118 mg), triethylamine (500 mg) and ethanol (15 ml) were added to 1-{1-{[4-ethoxycarbonylamino-4-piperidinyl]methyl}-4-(4-vinylbenzenesulfonyl)-2-piperazinone hydrochloride (200 mg), to react at 150° C. for 15 hours in a sealed tube. The reaction solution was concentrated, a 10% aqueous sodium carbonate solution was added to the residue, the mixture was extracted with dichloromethane, dried, and concentrated. The resulting residue was dried, concentrated, purified by column chromatography (dichloromethane:10% aqueous ammonia-containing methanol=20:1), and crystallized from ether to obtain the title compound (40 mg) as pale yellow crystals.

$^1$H-NMR (CDCl$_3$) δ: 1.24 (3H, t, J=7.0 Hz), 1.73 (2H, m), 2.02 (2H, m), 3.05 (2H, m), 3.30 (2H, m), 3.45–3.70 (4H, m), 3.72 (2H, s), 3.75 (2H, s), 4.07 (2H, q, J=7.0 Hz), 4.57 (1H, brs), 4.63 (2H, s), 5.49 (1H, d, J=11.0 Hz), 5.92 (1H, d, J=17.6 Hz), 6.50–6.60 (2H, m), 6.77 (1H, dd, J=11.0, 17.6 Hz), 7.58 (2H, d, J=8.4 Hz), 7.75 (2H, d, J=8.4 Hz), 8.20 (1H, d, J=5.8 Hz).

EXAMPLE 27

1-{[1-(2-Amino-4-pyridyl)-4-ethoxycarbonylamino-4-piperidinyl]methyl}-4-(4-vinylbenzensulfonyl)-2-piperazinone 2-Amino-4-chloropyridine (132 mg), triethylamine (700 mg) and ethanol (15 ml) were added to 1-{[4-ethoxycarbonylamino-4-piperidinyl]methyl}-4-(4-vinylbenzensulfonyl)-2-piperazinone hydrochloride (250 mg), to react at 155° C. for 20 hours in a sealed tube. The reaction solution was concentrated, a 10% aqueous sodium carbonate solution was added to the residue, the material was extracted with dichloromethane, dried, and concentrated. The resulting residue was dried, concentrated, purified by column chromatography (dichloromethane:10% aqueous ammonia-containing methanol=20:1), and crystallized from dichloromethane-hexane to obtain the title compound (58 mg) as pale yellow crystals.

$^1$H-NMR (CDCl$_3$) δ: 1.24 (3H, t, J=7.0 Hz), 1.71 (2H, m), 1.95 (2H, m), 2.98 (2H, m), 3.30 (2H, m), 3.40–3.60 (4H, m), 3.71 (2H, s), 3.79 (2H, s), 4.06 (2H, q, J=7.0 Hz), 4.35 (2H, brs), 4.60 (1H, brs), 5.49 (1H, d, J=11.0 Hz), 5.83 (1H, s), 5.92 (1H, d, J=17.6 Hz), 6.16 (1H, d, J=6.4 Hz), 6.77 (1H, dd, J=11.0, 17.6 Hz), 7.58 (2H, d, J=8.4 Hz), 7.70–7.80 (3H, m).

EXAMPLE 28

1-{[1-(2-Dimethylamino-4-pyridyl)-4-ethoxycarbonylamino-4-piperidinyl]methyl}-4-(4-viylbenzensulfonyl)-2-piperazinone 4-Chloro-2-(dimethylamino)pyridine hydrochloride (198 mg), triethylamine (700 mg) and ethanol (15 ml) were added to 1-{[4-ethoxycarbonylamino-4-piperidinyl]methyl}-4-(4-vinylbenzenesulfonyl)-2-piperazinone hydrochloride (250 mg), to react at 155° C. for 20 hours in a sealed tube. The reaction solution was concentrated, a 10% aqueous sodium carbonate solution was added to the residue, the material was extracted with dichloromethane, dried, and concentrated. The resulting residue was dried, concentrated, purified by column chromatography (dichloromethane:10% aqueous ammonia-containing methanol=20:1), and crystallized from ether to obtain the title compound (58 mg) as pale yellow crystals.

$^1$H-NMR (CDCl$_3$) δ: 1.23 (3H, t, J=7.0 Hz), 1.73 (2H, m), 1.99 (2H, m), 2.99 (2H, m), 3.05 (6H, s), 3.30 (2H, m), 3.45–3.70 (4H, m), 3.72 (2H, s), 3.75 (2H, s), 4.05 (2H, q, J=7.0 Hz), 4.52 (1H, brs), 5.48 (1H, d, J=11.0 Hz), 5.77 (1H, s), 5.92 (1H, d, J=17.6 Hz), 6.10 (1H, d, J=5.8 Hz), 6.76 (1H, dd, J=11.0, 17.6 Hz), 7.58 (2H, d, J=8.2 Hz), 7.75 (2H, d, J=8.2 Hz), 7.90 (1H, d, J=5.8 Hz).

EXAMPLE 29

1-(1-Acetoimidoyl-4-ethoxycarbonylamino-4-piperidylmethyl)-4-(6-chloronaphthalene-2-sulfonyl)-2-piperazinone hydrochloride A 4N hydrochloric acid solution in ethyl acetate (30 ml) and ethanol (6 ml) were added to 1-[1-(tert-butoxycarbonyl)-4-ethoxycarbonylamino-4-piperidylmethyl]-4-(6-chloronaphthalene-2-sulfonyl)-2-piperazinone (5.21 g), and the mixture was stirred at room temperature for 1 hour. The reaction solution was concentrated, the precipitated crystals were filtered, washed with ethyl acetate-ethanol, and dried to obtain 1-[4-ethoxycarbonylamino-4-piperidinylmethyl]-4-(6-chloronaphthalene-2-sulfonyl)-2-piperazinone hydrochloride (3.71 g). Ethyl acetimidate hydrochloride(148 mg) and triethylamine (0.337 ml) were added to a solution of 1-[4-ethoxycarbonylamino-4-piperidinylmethyl]-4-(6-chloronaphthalene-2-sulfonyl)-2-piperazinone hydrochloride (218 mg) in methanol (10 ml) under ice-cooling, and the mixture was stirred at room temperature overnight. After distillation of the solvent, purification by CHP20 column chromatography (water:acetonitrile:1N hydrochloric acid=100:0:0→60:40:0.5) afforded the colorless amorphous title compound (190 mg).

$^1$H-NMR (DMSO-d$_6$) δ: 1.15 (3H, t, J=7.0 Hz), 1.40–1.67 (2H, m), 2.00–2.18 (2H, m), 2.22 (3H, s), 2.95–4.00 (12H, m), 3.97 (2H, q, J=7.0 Hz), 7.16 (1H, brs), 7.75 (1H, dd, J=8.7, 2.1 Hz), 7.90 (1H, dd, J=8.7, 1.7 Hz), 8.21 (1H, d, J=8.8 Hz), 8.26–8.35 (2H, m), 8.61 (1H, s), 8.65 (1H, brs), 9.25(1H, brs).

EXAMPLE 30

4-(4-Bromobenzenesulfonyl)-1-{[4-ethoxycarbonylamino-1-(4-pyridyl)-4-piperidinyl]methyl}-2-piperazinone A mixture of benzyl 4-[[4-[(ethoxycarbonyl)amino]-1-(4-pyridinyl)-4-piperidinyl]methyl]-3-oxo-1-piperidincarboxylate (450 mg) obtained in Reference Example 9, 4N hydrochloric acid/ethyl acetate (0.25 ml), 10% Pd—C (100 mg) and methanol (20 ml) was stirred for 1 hour under the hydrogen atmosphere. The catalyst was removed by filtration, and the filtrate was concentrated under reduced pressure. Then, methylene chloride (20 ml) and triethylamine (400 mg) were added to the resulting residue to dissolve the material, 4-bromobenzenesulfonyl chloride (255 mg) was added at 0° C. and the mixture was stirred at room temperature for 2 hours. The reaction solution was washed with 1N sodium hydroxide and water, dried with magnesium sulfate, and concentrated under reduced pressure. The residue was purified by silica gel column chromatography (dichloromethane:10% aqueous ammonia-containing methanol=20:1) to obtain the title compound (364 mg) as colorless crystals.

$^1$H-NMR (CDCl$_3$) δ:1.24 (3H, t, J=7.0 Hz), 1.75 (2H, m), 2.05 (2H, m), 3.05 (2H, m), 3.30 (2H, m), 3.50–3.70 (4H, m), 3.74 (4H, s), 4.07 (2H, q, J=7.0 Hz), 4.64 (1H, br s), 6.64 (2H, d, J=6.6 Hz), 7.70–7.98 (4H, m), 7.65 (2H, d, J=8.6 Hz), 7.74 (2H, d, J=8.6 Hz), 8.26 (2H, d, J=6.6 Hz). IR (KBr): 1715, 1659, 1597, 1512, 1352, 1260, 1171 cm$^{-1}$.

EXAMPLE 31

4-(4-Bromobenzenesulfonyl)-1-{[4-ethoxycarbonylamino-1-(2-methyl-4-pyridyl)-4-piperidinyl]methyl}-2-piperazinone Triethylamine (400 mg) was added to a solution of 1-{[4-ethoxycarbonylamino-1-(2-methyl-4-pyridyl)-4-piperidinyl]methyl}-2-piperazinone hydrochloride (440 mg) obtained in Reference Example 11 in dichloromethane (15 ml), 4-bromobenzenesulfonyl chloride (255 mg) was added at 0° C., and the mixture was stirred at room temperature for 1 hour. An aqueous sodium carbonate solution was added to the reaction solution, the material was extracted with dichloromethane, dried, concentrated, and purified by silica gel column chromatography (dichloromethane:10% aqueous ammonia-containing methanol=20:1) to obtain the title compound (403 mg) as colorless crystals.

$^1$H-NMR (CDCl$_3$) δ: 1.24 (3H, t, J=7.0 Hz), 1.75 (2H, m), 2.04 (2H, m), 2.46 (3H, s), 3.06 (2H, m), 3.30 (2H, m), 3.50–3.70 (4H, m), 3.74 (4H, s), 4.07 (2H, q, J=7.0 Hz), 4.57 (1H, s), 6.45–6.55 (2H, m), 7.66 (2H, d, J=9.0 Hz), 7.74 (1H, dd, J=9.0 Hz), 8.17 (1H, d, J=6.6 Hz). IR (KBr): 1715, 1651, 1601, 1537, 1352, 1260, 1171 cm$^{-1}$.

FORMULATION EXAMPLE 1

An FXa inhibitor (e.g., deep vein thrombosis treating agent, cardiogenic cerebral infarction treating agent, and the like) containing a compound represented by the formula (I)

according to the present invention or a salt thereof as an active ingredient can be produced for example by the following formulations.

| 1. Capsule | |
|---|---|
| (1) Compound obtained in Example 2 | 40 mg |
| (2) Lactose | 70 mg |
| (3) Microcrystalline cellulose | 9 mg |
| (4) Magnesium stearate | 1 mg |
| 1 Capsule | 120 mg |

Components (1), (2) and (3) and a half of (4) are mixed and granulated. Then the remainder of Component (4) was added and the entire mass is filled into gelatin capsules.

| 2. Tablet | |
|---|---|
| (1) Compound obtained in Example 2 | 40 mg |
| (2) Lactose | 58 mg |
| (3) Corn starch | 18 mg |
| (4) Microcrystalline cellulose | 3.5 mg |
| (5) Magnesium stearate | 0.5 mg |
| 1 Table | 120 mg |

Components (1), (2) and (3) and a ⅔ of (4) and a half of Component (5) are mixed and granulated. Then the remainders of Components (4) and (5) are added to the granule, and then compressed into tablets.

FORMULATION EXAMPLE 2

50 mg of the compound obtained in Example 2 was dissolved in 50 ml of JP distilled water for injection, and JP distilled water for injection was further added to make 100 ml. This solution was filtered aseptically, and 1 ml aliquots of this solution were dispensed aseptically into injection vials, which were lyophilized and closed tightly.

Experiment 1

(1) Human Activated Coagulation Factor X (FXa) Inhibiting Activity

Method: A cuvette was charged with 225 µl of 0.05 M tris buffer (pH 8.3) containing 0.145 M sodium chloride and 2 mM calcium chloride, 5 µl of a sample (test compound dissolved in dimethyl sulfoxide) and 10 µl of human FXa (0.3 unit/ml), which were reacted at 37° C. for 10 minutes and then combined with 10 µl of a substrate (3 mM, S-2765) and further reacted at 37° C. for 10 minutes. Then the reaction was terminated by adding 25 µl of 50% aqueous acetic acid, and the change in the absorbance at 405 nm was determined using a spectrophotometer to calculate the concentration at which the FXa effect was inhibited by 50% ($IC_{50}$).

(2) In vitro Clotting Time Measurement
  (2-1) Prothrombin Time (PT) Measurement:
  A PT-test WAKO (WAKO PURE CHEMICAL) was employed together with an automatic coagulometer (STA compact DIAGNOSTICA STAGO). 97 µl of Human normal plasma (fresh human plasma, FFP, SEKISUI KAGAKU KOGYO) was combined with 3 µl of a test substance and pre-incubated at 37° C. for 4 minutes. 50 µl of the plasma described above was combined with 100 µl of rabbit brain-derived tissue thromboplastin solution and the time for the clotting was measured. The test substance was used after dissolving in dimethyl sulfoxide (DMSO). A concentration required for 2-fold prolongation of the clotting time was calculated based on the clotting time observed when DMSO was added instead of the test substance.

(2-2) Intrinsic Clotting Time (APTT) Measurement:
  A STA-APTT-LT (DIAGNOSTICA STAGO) was employed with together with an automatic coagulometer (STA compact DIAGNOSTICA STAGO). 97 µl of human normal plasma (fresh human plasma, FFP, SEKISUI KAGAKU KOGYO) was combined with 3 µl of a test substance. 50 µl of the plasma was combined with 50 µl of an active partial thromboplastin solution and preincubated at 37° C. for 4 minutes. 50 µl of 20 mmol/L $CaCl_2$ was added and the time for the clotting was determined. The test substance was used after dissolving in DMSO. A concentration required for 2-fold prolongation of the clotting time was calculated based on the clotting time observed when DMSO was added instead of the test substance.

(2-3) Thrombin Clotting Time (TT) Measurement:
  An automatic coagulometer (Biomatic B10, Sarstedt) was employed for a measurement. Human plasma-derived thrombin (Sigma) was dissolved in distilled water at 2.3 NIH unit/ml. 97 µl of human normal plasma (fresh human plasma, FFP, SEKISUI KAGAKU KOGYO) was combined with 3 µl of a test substance and pre-incubated at 37° C. for 3 minutes. 100 µl of the plasma described above was combined with 200 µl of a thrombin solution, and the time for the clotting was measured. The test substance was used after dissolving in DMSO. A concentration required for 2-fold prolongation of the clotting time was calculated based on the clotting time observed when DMSO was added instead of the test substance.

(3) Ex vivo Clotting Time Measurement (Mice)
  (3-1) Intravenous Administration:
  Male ICR mice (25 to 35 g, Slc) were employed. An animal received a test substance by a single administration of 5 ml/kg to a tail vein under anesthesia with pentobarbital (50 mg/kg, i.p.). 5 Minutes after the administration, 0.8 ml of the blood was taken from an abdominal aorta with a 1/10 volume of 3.8% sodium citrate (CYTORAL, YAMANOUCHI), and centrifuged at 3000 rpm for 15 minutes to obtain a plasma. 50 µl of the plasma described above was combined with 100 µl of rabbit brain-derived tissue thromboplastin solution and the time for the clotting was measured. The clotting time was measured using a PT-test WAKO (WAKO PURE CHEMICAL) together with an automatic coagulometer (STA compact DIAGNOSTICA STAGO). The test substance was used after dissolving in physiological saline, and the physiological saline was given instead of the test substance in a control group. The activity of the substance is indicated as a ratio (%) of the clotting time in a treatment group based on the clotting time in the control group.

(3-2) Oral Administration:
  Male ICR mice (25 to 35 g, Slc) were employed. 5 ml/kg of a test substance was given by a forcible oral administration to an animal after fasting for 12 hours or longer. 1 hour after administration, a blood was taken from an abdominal aorta under anesthesia with pentobarbital (50 mg/kg, i.p.). The test substance was used after suspending in 0.5% methyl cellulose, and 0.5% methyl cellulose was given instead of the test substance in a control group. Otherwise, the procedure similar to that for the intravenous administration described above was employed.

(4) In vivo Antithrombotic Effect Measurement (4-1) Rat Arteriovenous Shunt Method:

A method by Umetsu et al (Thromb. Haemostas., 39, 74–73, (1978)) was employed. Male SD rats (weighing 250 to 350 g) were used under anesthesia with pentobarbital (50 mg/kg, i.p.) to form an extracorporeal circulation of a polyethylene tube attached with a silk thread between the left jugular vein and the right jugular vein. In order to prevent a blood coagulation, the tube had previously been filled with a physiological saline containing heparin (50 U/ml). The blood was allowed to circulate for 15 minutes, the thrombus depositing on the silk thread during which period was weighed wet. A test substance was given orally or intravenously. When given orally, the test substance was suspended in 0.5% methyl cellulose, and given (5 ml/kg) 2 hours before initiation of the experiment to an animal while fasting. In a control group, 0.5% methyl cellulose was given instead of the test substance. When given intravenously, 1 ml/kg was given to a tail vein 5 minutes before initiating the blood circulation. The test substance was used after dissolving in physiological saline, and the physiological saline was given instead of the test substance in a control group. The activity of a test substance is indicated as a ratio (%) of the wet weight of the thrombus in a treatment group based on the wet weight in the control group.

(4-2) Rat Abdominal Vena Cava Partial Stasis Model

Male Sprague-Dawley rats (250–400 g, NIPPON CLAIR) were employed. An abdominal vena cava thrombus model was established by a modified Finkle's method (Thromb, Haemostas., 79, 431–438, 1998). An abdominal vena cava was exposed carefully under anesthesia with pentobarbital (50 mg/kg, i.p.), and the abdominal vena cava was tied at the renal vein bifurcation and at 1 cm downstream thereof, between which all branches were ligated. A balloon catheter (Fogarty, 2F, Baxter) was inserted from the left femoral vein, and the region between the two ties was injured three times by means of the balloon inflated with 200 to 300 ml of air. The balloon catheter was removed, the thread tied at the renal vein bifurcation was bound together with a 26G needle, and then the needle was removed, whereby establishing a partial stasis. After 30 minutes, another thread was bound, and the thrombus formed between the two threads was isolated carefully, and its wet weight was measured using a hooded analytical balance (BP110S, Sartorius). On the other hand, 2 ml of the blood was taken from an abdominal aorta with a 1/10 volume of 3.8% sodium citrate (CYTORAL, YAMANOUCHI), and centrifuged at 3000 rpm for 10 minutes to obtain a platelet-poor plasma (PPP). A test substance was given orally or intravenously. When given orally, the test substance was suspended in 0.5% methyl cellulose, and given (5 ml/kg) 2 hours before initiation of the experiment to an animal while fasting. In a control group, 0.5% methyl cellulose was given instead of the test substance. When given intravenously, 1 ml/kg was given to a tail vein 5 minutes before initiating the partial stasis. The test substance was used after dissolving in physiological saline, and the physiological saline was given instead of the test substance in a control group. The activity (% inhibition of thrombus formation) of a test substance is indicated as a ratio (%) of the wet weight of the thrombus in a treatment group based on the wet weight in the control group.

(4-3) Rat Deep Vein Thrombosis (DVT) Model

Male SD rats (weighing 250 to 350 g) were employed. A polyethylene tube was inserted into the left femoral vein under anesthesia with pentobarbital (50 mg/kg, i.p.). In the polyethylene tube, a silk thread (5 cm in length) which had previously been attached to a guide wire was inserted, and a physiological saline containing heparin (50 U/ml) was filled in order to prevent a blood coagulation. After inserting the polyethylene to reach the abdominal vena cava, the silk thread was placed in the abdominal vena cava using the guide wire. After placing for 30 minutes, heparin (200 U/kg) was given intravenously from a tail vein. After exsanguinating by cutting a brachial artery, the abdominal region was opened and the silk thread was taken out and examined for the wet weight of the thrombus depositing on the thread (including the weight of the thread). A test substance was given at 1 ml/kg to a tail vein 5 minutes before placing the silk thread. The test substance was used after dissolving in physiological saline, and the physiological saline was given instead of the test substance in a control group. The wet weight only of the thrombus was calculated as (wet weight of thrombus depositing on silk thread)–(wet weight determined after immersing silk thread in heparinized venous blood (11.6±0.2 mg)).

EXPERIMENTAL RESULTS $IC_{50}$ value of human FXa inhibiting activity and PT 2-fold extending concentration (CT2) are shown in Table 1. From this result, it is evident that the compound of the present invention has an excellent FXa inhibiting activity, and exhibits a strong anti-blood coagulation activity.

TABLE 1

| Example No. | Fxa $IC_{50}$ (μM) | PT CT2 (μM) |
|---|---|---|
| 1 | 0.0046 | 0.27 |

INDUSTRIAL APPLICABILITY

Compound (I) of the present invention or a salt thereof has the excellent FXa inhibiting activity, has a less hemorrhagic side effect, is useful as an anticoagulant capable of being orally absorbed, and thus can advantageously be used for preventing and/or treating various diseases attributable to thrombus or infarction.

The invention claimed is:

1. A compound represented by the formula:

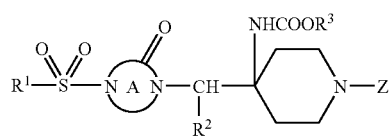

wherein $R^1$ denotes a group represented by the formula:

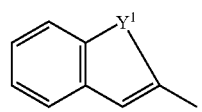

(wherein $Y^1$ denotes O, NH, S, $CH_2CH_2$, CH=CH, N=CH, $OCH_2$, $SCH_2$ or two hydrogen atoms), or a group represented by the formula:

(wherein Y² denotes O, S, N=C or CH=CH), each of which may be substituted, ring A is a ring represented by:

wherein n denotes 1 or 2, and m denotes 2 or 3 and may be further substituted,

R² denotes a hydrogen atom, an optionally substituted $C_{1-4}$ alkyl group, an optionally esterified carboxyl group or a cyano group, R³ denotes a $C_{1-4}$ alkyl group or a $C_{2-4}$ alkenyl group, each of which may be substituted with a substituent selected from a halogen atom, a hydroxy group, an optionally substituted alkoxy group, an optionally substituted amino group and an optionally esterified carboxyl group, and Z denotes (1) an optionally substituted imidoyl group or an optionally substituted nitrogen-containing heterocyclic group, or a salt thereof.

2. The compound according to claim 1, wherein R¹ is an optionally substituted naphthyl group.

3. The compound according to claim 1, wherein R¹ is 6-halogeno-2-naphthyl group.

4. The compound according to claim 1, wherein R¹ is an optionally substituted benzopyranyl group.

5. The compound according to claim 1, wherein R¹ is 7-halogeno-2H-3-benzopyranyl group.

6. The compound according to claim 1, wherein R¹ is an optionally substituted phenyl group.

7. The compound according to claim 1, wherein R¹ is 4-$C_{2-4}$ alkenyl-phenyl group.

8. The compound according to claim 1, wherein ring A is an optionally substituted oxopiperazine ring.

9. The compound according to claim 1, wherein R² is a hydrogen atom.

10. The compound according to claim 1, wherein R³ is a $C_{1-4}$ alkyl group which may be substituted with a substituent selected from a halogen atom, a hydroxy group, an optionally substituted alkoxy group, an optionally substituted amino group and an optionally esterified carboxyl group.

11. The compound according to claim 1, wherein R³ is methyl, ethyl, or propyl.

12. The compound according to claim 1, wherein Z is an optionally substituted imidoyl group.

13. The compound according to claim 1, wherein Z is an optionally substituted $C_{1-4}$ imidoyl group.

14. The compound according to claim 1, wherein Z is an optionally substituted amidino group.

15. The compound according to claim 1, wherein Z is an optionally substituted nitrogen-containing heterocyclic group.

16. The compound according to claim 1, wherein Z is a nitrogen-containing heterocyclic group which may be substituted with a substituent selected from a $C_{1-4}$ alkyl group and an optionally substituted amino group.

17. The compound according to claim 1, wherein Z is an optionally substituted pyrimidyl group.

18. The compound according to claim 1, wherein Z is an optionally substituted pyridyl group.

19. The compound according to claim 1, which is a compound selected form the group consisting of 4-(6-chloronaphthalene-2-sulfonyl)-1-[4-methoxycarbonylamino-1-(4-pyridyl)piperidin-4-ylmethyl]-2-piperazinone, 4-(6-chloronaphthalene-2-sulfonyl)-1-[4-ethoxycarbonylamino-1-(4-pyridyl)piperidin-4-ylmethyl]-2-piperazinone, 4-(7-chloro-2H-benzopyran-3-sulfonyl)-1-[4-methoxycarbonylamino-1-(4-pyridyl)piperidin-4-ylmethyl]-2-piperazinone, 4-(7-chloro-2H-benzopyran-3-sulfonyl)-1-[4-ethoxycarbonylamino-1-(4pyridyl)piperidin-4ylmethyl]-2-piperazinone, 1-[4-methoxycarbonylamino-1-(4-pyridyl)piperidin-4-ylmethyl]-4-(4-vinylbenzenesulfonyl)-2-piperazinone, 1-[4-ethoxycarbonylamino-1-(4-pyridyl)piperidin-4-ylmethyl]-4-(4-vinylbenzenesulfonyl)-2-piperazinone, 1-[4-ethoxycarbonylamino-1-(2-methyl-4-pyridyl)piperidin-4-ylmethyl]-4-(4-vinylbenzenesulfonyl)-2-piperazinone, 1-[4-propoxycarbonylamino-1-(4-pyridyl)piperidin-4-ylmethyl]-4-(4-vinylbenzenesulfonyl)-2-piperazinone, 1-[4-ethoxycarbonylamino-1-(4-pyridyl)piperidin-4ylmethyl]-4-(4-bromobenzensulfonyl)-2piperazinone and 1-[4ethoxycarbonylamino-1-(2-methyl-4-pyridyl)piperidin-4-ylmethyl]-4-(4-bromobenzenesulfonyl)-2-piperazinone or a salt thereof.

20. A prodrug of a compound represented by the formula:

wherein R¹ denotes a group represented by the formula:

(wherein Y¹ denotes O, NH, S, CH₂CH₂, CH=CH, N=CH, OCH₂, SCH₂ or two hydrogen atoms), or a group represented by the formula:

(wherein Y² denotes O, S, N=C or CH=CH), each of which may be substituted, ring A is a ring represented by:

wherein n denotes 1 or 2, and m denotes 2 or 3 and may be further substituted, $R^2$ denotes a hydrogen atom, an optionally substituted $C_{1-4}$ alkyl group, an optionally esterified carboxyl group or a cyano group, $R^3$ denotes a $C_{1-4}$ alkyl group or a $C_{2-4}$ alkenyl group, each of which may be substituted with a substituent selected from a halogen atom, a hydroxy group, an optionally substituted alkoxy group, an optionally substituted amino group and an optionally esterified carboxyl group, and Z denotes an optionally substituted imidoyl group or an optionally substituted nitrogen-containing heterocyclic group, or a salt thereof.

21. A pharmaceutical composition, which comprises an effective amount of a compound represented by the formula:

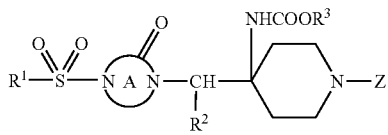

wherein $R^1$ denotes a group represented by the formula:

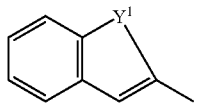

(wherein $Y^1$ denotes O, NH, S, $CH_2CH_2$, CH=CH, N=CH, $OCH_2$, $SCH_2$ or two hydrogen atoms), or a group represented by the formula:

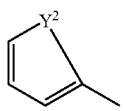

(wherein $Y^2$ denotes O, S, N=C or CH=CH), each of which may be substituted, ring A is a ring represented by:

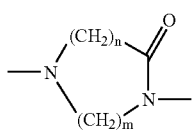

wherein n denotes 1 or 2, and m denotes 2 or 3 and may be further substituted, $R^2$ denotes a hydrogen atom, an optionally substituted $C_{1-4}$ alkyl group, an optionally esterified carboxyl group or a cyano group, $R^3$ denotes a $C_{1-4}$ alkyl group or a $C_{2-4}$ alkenyl group, each of which may be substituted with a substituent selected from a halogen atom, a hydroxy group, an optionally substituted alkoxy group, an optionally substituted amino group and an optionally esterified carboxyl group, and Z denotes an optionally substituted imidoyl group or an optionally substituted nitrogen-containing heterocyclic group, or a salt thereof, or a prodrug thereof and a pharmaceutically acceptable carrier.

22. A process for preparing a compound represented by the formula:

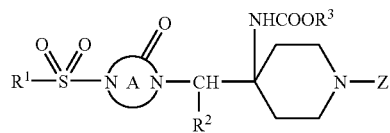

wherein each symbol is as defined hereinafter, or a salt thereof, which comprises (1) reacting a compound represented by the formula:

$R^1SO_2Q$ wherein Q denotes a leaving group, and the other symbol is as defined in claim 1, or a salt thereof, with a compound represented by the formula:

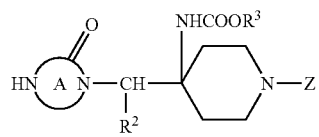

wherein the symbols are as defined in claim 1, or a salt thereof, (2) reacting a compound represented by the formula:

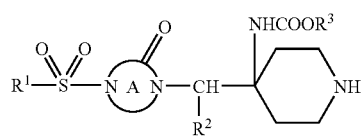

wherein symbols are as defined in claim 1, or a salt thereof, with a compound represented by the formula:

$L^1$-Z wherein $L^1$ denotes a leaving group, and the other symbol is as defined in claim 1, or a salt thereof, or (3) reacting a compound represented by the formula;

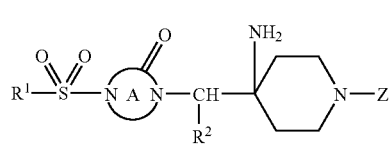

wherein the symbols are as defined in claim 1, or a salt thereof, with a compound represented by the formula:

$L^2$-$COOR^3$ wherein $L^2$ denotes a leaving group, and the other symbol is as defined in claim 1, or a salt thereof.

23. A method for inhibiting blood coagulation in a mammal, which comprises administering an effective amount of the compound according to claim 1 or a salt thereof, or a prodrug thereof to the mammal.

24. A method for inhibiting activated blood coagulation factor X in a mammal, which comprises administering an effective amount of the compound according to claim 1 or a salt thereof, or a prodrug thereof to the mammal.

25. A method for preventing and/or treating cardiac infarction, cerebral thrombosis, deep vein thrombosis, pulmonary thrombotic embolus or thrombotic embolus during or after operation in a mammal, which comprises administering an effective amount of the compound according to claim 1 or a salt thereof, or a prodrug thereof to the mammal.

* * * * *